United States Patent
Green et al.

(10) Patent No.: US 11,938,168 B2
(45) Date of Patent: *Mar. 26, 2024

(54) OPHTHALMIC COMPOSITIONS AND METHODS OF USE THEREFOR

(71) Applicant: Auckland Uniservices Limited, Auckland (NZ)

(72) Inventors: Colin Green, Auckland (NZ); Carol Ann Greene, Auckland (NZ); Trevor Sherwin, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 88 days.

This patent is subject to a terminal disclaimer.

(21) Appl. No.: 17/078,949

(22) Filed: Oct. 23, 2020

(65) Prior Publication Data
US 2022/0047676 A1    Feb. 17, 2022

Related U.S. Application Data

(63) Continuation of application No. 15/555,909, filed as application No. PCT/NZ2016/050033 on Mar. 4, 2016, now Pat. No. 10,842,850.

(30) Foreign Application Priority Data

Mar. 5, 2015    (NZ) ........................................ 705727

(51) Int. Cl.
| | | |
|---|---|---|
| *A61K 38/18* | (2006.01) | |
| *A61K 31/573* | (2006.01) | |
| *A61K 45/06* | (2006.01) | |
| *C07K 14/495* | (2006.01) | |

(52) U.S. Cl.
CPC ........ *A61K 38/1841* (2013.01); *A61K 31/573* (2013.01); *A61K 45/06* (2013.01); *A61K 2300/00* (2013.01); *C07K 14/495* (2013.01)

(58) Field of Classification Search
CPC . A61K 38/1841; A61K 31/573; C07K 14/495
See application file for complete search history.

(56) References Cited

U.S. PATENT DOCUMENTS

| | | | |
|---|---|---|---|
| 3,786,812 A | 1/1974 | Neefe | |
| 5,124,392 A | 6/1992 | Robertson et al. | |
| 5,411,940 A | 5/1995 | Nixon et al. | |
| 5,462,925 A * | 10/1995 | Ogawa | A61P 29/00 530/324 |
| 7,947,264 B2 | 5/2011 | Ferguson et al. | |
| 8,101,582 B2 | 1/2012 | Kabra | |
| 9,149,525 B2 | 10/2015 | Jaffe et al. | |
| 10,842,850 B2 | 11/2020 | Green et al. | |
| 11,154,560 B2 | 10/2021 | Bowman et al. | |
| 11,304,961 B2 | 4/2022 | Kreyenborg et al. | |
| 2008/0286229 A1 | 11/2008 | Huang et al. | |
| 2013/0165419 A1 | 6/2013 | Lindstrom et al. | |
| 2013/0243734 A1 | 9/2013 | Green et al. | |
| 2014/0046242 A1 | 2/2014 | Jaffe et al. | |
| 2014/0271597 A1 | 9/2014 | Osio Sancho | |
| 2014/0322175 A1 | 10/2014 | Hariri | |

FOREIGN PATENT DOCUMENTS

| | | | | |
|---|---|---|---|---|
| CN | 104548210 A | 4/2015 | | |
| KR | 101518370 B1 | 5/2015 | | |
| WO | 96/32131 A1 | 10/1996 | | |
| WO | 2007/099337 A1 | 9/2007 | | |
| WO | 2007/104945 A2 | 9/2007 | | |
| WO | 2007/106381 A2 | 9/2007 | | |
| WO | 2009/071594 A1 | 6/2009 | | |
| WO | WO-2010068281 A2 * | 6/2010 | ........... | A61F 9/0017 |
| WO | 2012/088044 A2 | 6/2012 | | |
| WO | 2016/140581 A1 | 9/2016 | | |

OTHER PUBLICATIONS

Greene et al., ARVO Annual Meeting Abstract, Jun. 2013.*
Karamichos, D. et al., "Comparison of ECM Secretion by Corneal Stem Cells and Corneal Fibroblasts in a 3D Model," Investigative Ophthalmology & Visual Science, vol. 52:5147 (2011).
Karamichos, D. et al., "TGF-[beta]3 Stimulates Stromal Matrix Assembly by Human Corneal Keratocyte-Like Cells," Investigative Ophthalmology & Visual Science, vol. 54 (10):6612 (2013).
Karamichos, D., et al., "Novel in vitro model for keratoconus disease," Journal of Functional Biomaterials, vol. 3 (4):760-775 (2012).
Karamichos, D., et al., "Transforming growth factor ?3 regulates assembly of a non fibrotic matrix in a 3D corneal model," Journal of Tissue Engineering and Regenerative Medicine, vol. 5(8): e228-e238 (2011).
Kato, Y. et al., "Stimulation by glucocorticoid of the synthesis of cartilage-matrix proteoglycans produced by rabbit costal chondrocytes in vitro," Journal of Biological Chemistry, vol. 260(4): 2364-2373 (1985).
Kenney, M.C. et al., "The cascade hypothesis of keratoconus. Contact lens and anterior eye," vol. 26(3):139-146 (2003).
Klintworth, G. K. et al., "Corneal dystrophies and keratoconus," Current Opinion in Ophthalmology, vol. 6(4): 44-56 (1995).
Klintworth, G. K.., "Advances in the molecular genetics of corneal dystrophies," American Journal of Ophthalmology, vol. 128(6): 747-754 (1999).

(Continued)

*Primary Examiner* — Xiaozhen Xie

(74) *Attorney, Agent, or Firm* — Nelson Mullins Riley & Scarborough LLP; Jane E. Remillard, Esq.; Cynthia L. Kanik

(57) ABSTRACT

The present invention encompasses ophthalmic compositions that may be used for various conditions of the eye, and particularly, conditions of the cornea. Also encompassed are methods that utilise these compositions and kits that include these compositions.

16 Claims, 20 Drawing Sheets

Specification includes a Sequence Listing.

(56) References Cited

OTHER PUBLICATIONS

Kolambkar, Y. M., et al., "Chondrogenic differentiation of amniotic fluid-derived stem cells," Journal of Molecular Histology, vol. 38(5):405-413 (2007).

Krachmer, J. H., et al., "Keratoconus and related noninflammatory corneal thinning disorders," Survey of Ophthalmology, vol. 28(4): 293-322 (1984).

Ku, J. Y., et al., "Laser scanning in vivo confocal analysis of keratocyte density in keratoconus," Ophthalmology, vol. 115(5):845-850 (2008).

Kulyk, W. M. et al., "Ethanol exposure stimulates cartilage differentiation by embryonic limb mesenchyme cells," Experimental Cell Research, vol. 223(2): 290-300 (1996).

Lee, K. D., et al., "In vitro hepatic differentiation of human mesenchymal cells," Hepatology, vol. 40(6):1275-1284 (2004).

Legeais, J.-M., et al., "Nineteen years of penetrating keratoplasty in the Hotel-Dieu Hospital in Paris," Cornea, vol. 20(6):603-606 (2001).

Liang C.-Z., et al., "Dual release of dexamethasone and TGF-b3 from polymeric microspheres for stem cell matrix accumulation in a rat disc degeneration model," Acta Biomaterialia, vol. 9(12): 9423-9433 (2013).

Linsenmayer, T. F., et al., "Heterotypic collagen fibrils and stabilizing collagens," Annals of the New York Academy of Sciences, vol. 580(1): 143-160 (1990).

Ludwig, A., "The use of mucoadhesive polymers in ocular drug delivery," Advanced Drug Delivery Reviews, vol. 57(11): 1595-1639 (2005).

Marshall, G. E., et al., "Collagens in ocular tissues," The British Journal of Ophthalmology, vol. 77(8): 515-524 (1993).

Mazzotta, C., et al., "Corneal healing after riboflavin ultraviolet—A collagen cross-linking determined by confocal laser scanning microscopy in vivo: early and late modifications," American Journal of Ophthalmology, vol. 146(4): 527-533 (e521) (2008).

Meek, K. M., et al., "Changes in collagen orientation and distribution in keratoconus corneas," Investigative Ophthalmology & Visual Science, vol. 46(6): 1948-1956 (2005).

Mencucci, R., et al., "Effects of riboflavin/UVA corneal cross?linking on keratocytes and collagen fibres in human cornea," Clinical & Experimental Ophthalmology, vol. 38(1): 49-56(2010).

Mendler, M., et al., "Cartilage contains mixed fibrils of collagen types II, IX, and XI," The Journal of Cell Biology, vol. 108(1): 191-197 (1989).

Menetrey, J., et al., "Growth factors improve muscle healing in vivo," Journal of Bone & Joint Surgery, British Volume, vol. 82(1):131-137 (2000).

Na, K. et al., "Combination material delivery of dexamethasone and growth factor in hydrogel blended with hyaluronic acid constructs for neocartilage formation," Journal of Biomedical Materials Research, Part A, vol. 83A(3):779-786 (2007).

NCBI Blast Results, RID-BX1MYYTS015 and Conserved Domains on gi/20151052 dated Apr. 23, 2019, 14 pages.

Niederer, R. L., et al., "Laser scanning in vivo confocal microscopy reveals reduced innervation and reduction in cell density in all layers of the keratoconic cornea," Investigative Ophthalmology & Visual Science, vol. 49(7): 2964-2970 (2008).

Nirmal, HB. et al., "In-Situ gel: New trends in Controlled and Sustained Drug Delivery System," International Journal of PhamTech Research, vol. 2(2): 1398-1408 (2010).

Nozaki et al., Clin. Immunol., 2006, vol. 119(3):272-279.

Patel, D. et al., "Understanding keratoconus: what have we learned from the New Zealand perspective?," Clinical and Experimental Optometry, vol. 96(2):183-187 (2013).

Patel, H.Y., et al., "The New Zealand National Eye Bank study 1991-2003: a review of the source and management of corneal tissue," Cornea, vol. 24(5):576-582 (2005).

Peran, M., et al., Transdifferentiation: why and how?, Cell Biology International, vol. (35):373-379 (2011).

Pramanik, S., et al., "Extended long-term outcomes of penetrating keratoplasty for keratoconus," Ophthalmology, vol. 113(9): 1633-1638 (2006).

Premaraj, S. et al., "Sustained delivery of bioactive cytokine using a dense collagen gel vehicle collagen gel delivery of bioactive cytokine," Arch Oral Biol., vol. 51(4): 325-333 (2006).

Puetzer, J. et al., "Comparative Review of Growth Factors for Induction of Three-Dimensional In Vitro Chondrogenesis in Human Mesenchymal Stem Cells Isolated from Bone Marrow and Adipose Tissue," Tissue Engineering Part B-Reviews, vol. 16(4):435-444 (2010).

Rabinowitz, Y. S. "Keratoconus," Survey of Ophthalmology, vol. 42(4):297-319 (1998).

Robertson, J. et al., "Adenoviral gene transfer of bioactive TGF?1 to the rodent eye as a novel model for anterior subcapsular cataract," Mol Vis., vol. 13: 457-469 (2007).

Romero-Jiménez, M., et al., "Keratoconus: a review," Contact Lens and Anterior Eye, vol. 33(4): 157-166 (2010).

Rupenthal, I. D., et al., "Comparison of ion-activated in situ gelling systems for ocular drug delivery. Part 2: Precorneal retention and in vivo pharmacodynamic study," International Journal of Pharmaceutics (2011).

Schuldiner, M., et al., "Effects of eight growth factors on the differentiation of cells derived from human embryonic stem cells," Proceedings of the National Academy of Sciences, vol. 97(21):11307-11312. (2000).

Search Report and Written Opinion, SG Application No. 11201708114S, dated Jul. 17, 2018, 9 pages.

Shah, M., et al., "Neutralisation of TGF-beta 1 and TGF-beta 2 or exogenous addition of TGF-beta 3 to cutaneous rat wounds reduces scarring," Journal of Cell Science, vol. 108(3): 985-1002 (1995).

Sherwin, T., et al., "Morphological changes in keratoconus: pathology or pathogenesis," Clinical & Experimental Ophthalmology, vol. 32(2): 211-217 (2004).

Spoerl, E., et al., "Induction of cross-links in corneal tissue," Experimental Eye Research, vol. 66(1): 97-103 (1998).

Takahashi K. et al., "Induction of pluripotent stem cells from mouse embryonic and adult fibroblast cultures by defined factors," Cell, vol. 126 (4): 663-676 (2006).

Tsang, M. L-S, et al., "Characterization of recombinant soluble human transforming growth factor-beta receptor type II (rhTGF-beta sRII)," Cytokine, vol. 7(5): 389-397 (1995).

Wells, S. M., "Mechanical design of elastic biopolymers," Physics in Canada, vol. 59(2):67-74 (2003).

Wernig, M., et al., "In vitro reprogramming of fibroblasts into a pluripotent ES-cell-like state," Nature, vol. 448 (7151):318-324. (2007).

West-Mays et al., Investigative Ophthalmology & Visual Science, 1999, vol. 40(5):887-896.

Wilson, S. E., et al., "Corneal Cells: Chatty in Development Homeostasis, Wound Healing, and Disease," American Journal of Ophthalmology, vol. 136(3):530-536 (2003).

Winter, A., et al., "Cartilage?like gene expression in differentiated human stem cell spheroids: A comparison of bone marrow-derived and adipose tissue-derived stromal cells," Arthritis & Rheumatism, vol. 48(2): 418-429 (2003).

Alipour, H. et al., "Therapeutic applications of collagenase (metalloproteases): A review," Asian Pacific Journal of Tropical Biomedicine, vol. 6 (11):975-981 (2016).

Ashwin, P. T., & McDonnell, P. J., et al., "Collagen cross-linkage: a comprehensive review and directions for future research," British Journal of Ophthalmology, vol. 94(8): 965-970 (2010).

Bettahi, I. et al., "Genome-Wide Transcriptional Analysis of Differentially Expressed Genes in Diabetic, Healing Corneal Epithelial Cells: Hyperglycemia-Suppressed TGFb3 Expression Contributes to the Delay of Epithelial Wound Healing in Diabetic Corneas," Diabetes, vol. 63(2): 715-727 (2014).

Branton, MH et al., "TGF-beta and fibrosis," Microbes Infect., vol. 1(15):1349-1365 (1999).

Carrington, L., et al., "Differential Regulation of Key Stages in Early Corneal Wound Healing by TGF-ß Isoforms and Their Inhibitors," Invest Ophthalmol Vis Sci., vol. 47(5):1886-1894 (2006).

(56) References Cited

OTHER PUBLICATIONS

Cosar, C.B., et al., "Indications for penetrating keratoplasty and associated procedures, 1996-2000," Cornea, vol. 21(2):148-151 (2002).
Cowin, A. J., "Expression of TGF-beta and its receptors in murine fetal and adult dermal wounds," European Journal of Dermatology, vol. 11(5): 424-431 (2001).
Desmouliere, A., et al. "Tissue repair, contraction, and the myofibroblast," Wound Repair and Regeneration, vol. 13(1): 7-12 (2005).
Dias, J. M., et al., "Anterior and posterior corneal stroma elasticity assessed using nanoindentation," Experimental eye research, vol. 115: 41-46 (2013).
Dias, J.M., et al., "Anterior and posterior corneal stroma elasticity after corneal collagen crosslinking treatment," Experimental eye research, vol. 116:58-62 (2013).
Dickinson, M. E., et al., "Probing more than the surface," Materials Today, vol. 12(7): 46-50 (2009).
Diegelmann, R. et al., "Wound Healing: An Overview of Acute, Fibrotic and Delayed Healing," Frontiers in Bioscience, vol. 9:283-289 (2004).
Diekman, B. O. et al., "Chondrogenesis of adult stem cells from adipose tissue and bone marrow: induction by growth factors and cartilage-derived matrix," Tissue engineering Part A, vol. 16(2):523-533 (2009).
Dobbins, K.R., et al., "Trends in the indications for penetrating keratoplasty in the Midwestern United States," Cornea, vol. 19(6):813-816 (2000).
Ebenstein, D. M., et al., "Nanoindentation of biological materials," Nano Today, vol. 1(3): 26-33 (2006).
Edmund, C., "Corneal elasticity and ocular rigidity in normal and keratoconic eyes," Acta ophthalmologica, vol. 66(2):134-140 (1988).
Edwards, M., et al., "Indications for corneal transplantation in New Zealand: 1991-1999," Cornea, vol. 21(2):152-155 (2002).
Extended European Search Report, European Application No. 16759200, dated Sep. 25, 2018, 19 pages.
Farquharson, C., et al., "Ascorbic acid-induced chondrocyte terminal differentiation: the role of the extracellular matrix and 1, 25-dihydroxyvitamin D," European journal of cell biology, vol. 76(2): 110-118 (1998).
Fredrick, D.R., "Myopia," BMJ: British Medical Journal, vol. 324(7347):1195-1199 (2002).
Fukuchi, T., et al., "Lysosomal enzyme activities in conjunctival tissues of patients with keratoconus," Archives of Ophthalmology, vol. 112(10):1368-1374 (1994).
Funderburgh, J. L. et al., "Proteoglycan expression during transforming growth factor-induced keratocyte-myofibroblast transdifferentiation," Journal of Biological Chemistry, vol. 276(47): 44173-44178 (2001).
Funderburgh, J.L. et al., "Keratocyte phenotype mediates proteoglycan structure," Journal of Biological Chemistry, vol. 278(46):45629 (10 pages) (2003).
Funderburgh, J.L., "Corneal Proteoglycans, in Proteoglycans: structure, biology and molecular interactions," R.V. Lozzo, Editor, Marcel Dekker, Chapter 11: 37 pages (2000).
Gabbiani, G. "The myofibroblast in wound healing and fibrocontractive diseases," The Journal of Pathology, vol. 200(4):500-503 (2003).
Ghoniem, A. A., et al., "Improved adipogenic in vitro differentiation: comparison of different adipogenic cell culture media on human fat and bone stroma cells for fat tissue engineering," Anatomy & Cell Biology, vol. 48(2):85-94 (2015).
Gordon, M.K. et al., "Collagens," Cell and Tissue Research, vol. 339(1): 247-257 (2010).
Greene, C. et al., "Exploring cell plasticity: the corneal keratocyte and beyond," Investigative Ophthalmology & Visual Science, vol. 54(13) p. 5250; abstract (2013).
Greene, C. et al., "Keratocytes are induced to produce collagen type II: A new strategy for in vivo corneal matrix regeneration," Experimental Cell Research, Elsevier, vol. 347(1):241-249 (2016).
Greene, C.A., et al., "Cells from the adult corneal stroma can be reprogrammed to a neuron-like cell using exogenous growth factors," Experimental Cell Research, vol. 322(1):122-132 (2013).
Greenstein, S. A., et al., "Natural history of corneal haze after collagen crosslinking for keratoconus and corneal ectasia: Scheimpflug and biomicroscopic analysis," Journal of Cataract & Refractive Surgery, vol. 36(12): 2105-2114 (2010).
Gurdon, J.B. et al., "Nuclear Reprogramming in Cells," Science, vol. 322:1811-1815. (2008).
Håkelien, A.M. et al., "Novel approaches to transdifferentiation," Cloning & Stem Cells, vol. 4(4):379-387 (2002).
Hakelien, A.M. et al., "Novel approaches to transdifferentiation," Cloning & Stem Cells, vol. 4(4):379-387 (2002).
Hao, Y. et al., "Postoperative application of dexamethasone in the cornea suffered from iron body injury", Chinese Journal of Ocular Trauma and Occupational Eye Disease, vol. 32(1):74-75 (2010).
He, K.W. et.al, "Preliminary study of dexamethasone's curative effect of acid burns on rat cornea," Int Eye Sci., vol. 14(3):416-418(2014).
Heng, B. C., et al., "Directing stem cell differentiation into the chondrogenic lineage in vitro," Stem Cells, vol. 22(7):1152-1167 (2004).
Hollingsworth, J. G. et al., "In vivo corneal confocal microscopy in keratoconus," Ophthalmic and Physiological Optics, vol. 25(3): 254-260 (2005).
Ignotz, R. A. et al., "Regulation of fibronectin and type I collagen mRNA levels by transforming growth factor-beta," Journal of Biological Chemistry, vol. 262(14): 6443-6446 (1987).
Ignotz, R. A., et al., "Transforming growth factor-beta stimulates the expression of fibronectin and collagen and their Incorporation into the extracellular matrix," Journal of Biological Chemistry, vol. 261: 4337-4345 (1986).
International Preliminary Report on Patentability, PCT/NZ2016/050033, dated Aug. 4, 2016, 11 pages.
International Search Report and Written Opinion, PCT/NZ2016/050033, dated Aug. 4, 2016, 11 pages.
Jester, J. V., et al., "Characterization of avascular corneal wound healing fibroblasts, New insights into the myofibroblast," The American Journal of Pathology, vol. 127(1): 140-148 (1987).
Jester, J. V., et al., "TGF? induced myofibroblast differentiation of rabbit keratocytes requires synergistic TGF?, PDGF and integrin signalling,. Experimental Eye Research, vol. 75(6): 645-657 (2002).
Jhanji, V., et al., "Management of keratoconus: current scenario," British Journal of Ophthalmology, vol. 95(8): 1044-1050 (2011).
Jinabhai, A., et al., "Pellucid corneal marginal degeneration: a review," Contact Lens & Anterior Eye, vol. 34(2): 56-63 (2010).
Johnstone, B., et al., "In Vitro Chondrogenesis of Bone Marrow-Derived Mesenchymal Progenitor Cells," Experimental Cell Research, vol. 238(1): 265-272 (1998).
Kadler, K. E., et al., "Collagens at a glance," Journal of Cell Science, vol. 120(12):1955-1958 (2007).
Wollensak, G., et al., "Riboflavin/ultraviolet-A-induced collagen crosslinking for the treatment of keratoconus," American Journal of Ophthalmology, vol. 135(5): 620-627 (2003).
Wollensak, J., et al., "Biochemical studies on human corneal proteoglycans—a comparison of normal and keratoconic eyes," Graefe's Archive for Clinical and Experimental Ophthalmology, vol. 228(6): 517-523 (1990).
Worster, A. A., et al., "Effect of transforming growth factor ?1 on chondrogenic differentiation of cultured equine mesenchymal stem cells," American Journal of Veterinary Research, vol. 61(9):1003-1010 (2000).
Written Opinion, SG Application No. 11201708114S, dated Feb. 25, 2019, 7 pages.
Wu, J. et al., "Bioengineering Organized, Multilamellar Human Corneal Stromal Tissue by Growth Factor Supplementation on Highly Aligned Synthetic Substrates," Tissue Engineering Part A, vol. 19 (17-18):2063-2075 (2013).
Yamanaka, S. et al., "Nuclear reprogramming to a pluripotent state by three approaches," Nature, vol. 465 (7299):704-712. (2010).
Yoon Y. M., et al., "Epidermal growth factor negatively regulates chondrogenesis of mesenchymal cells by modulating the protein

(56) References Cited

OTHER PUBLICATIONS kinase C-alpha, Erk-1, and p38 MAPK signaling pathways," Biol Chem., vol. 275(16):12353-12359 (2000).
Zadnik et al., Cornea, 2000, vol. 19(6):804-812 (abstract).
Alpins N, et al., "New method of quantifying corneal topographic astigmatism that corresponds with manifest refractive cylinder," J Cataract Refract Surg., vol. 38:1978-1988 (2012).
Aquavella JV., "New aspects of contact lenses in ophthalmology," Adv Ophthalmol., vol. 32:2-34 (1976).
Calossi, A et al., "Orthokeratology and riboflavin-UVA corneal collagen cross-linking in Keratoconus," Journal of Emmetropia: Journal of Cataract, Refractive and Corneal Surgery, ISSN-e 2171-4703, vol. 1, (3):126-131 (2010).
Daull P, et al., "A preliminary evaluation of dexamethasone palmitate emulsion: a novel intravitreal sustained delivery of corticosteroid for treatment of macular edema," J Ocul Pharmacol Ther., vol. 29: 258-269 (2013).
Du TT, et al., "Conductive keratoplasty," Curr Opin Ophthalmol., vol. 18:334-337 (2007).
Elks J., et al., "The Dictionary of Drugs: Chemical Data: Chemical Data, Structures and Bibliographies," Springer. pp. 367 (2014).
Goto S, et al., "Corneal Topography for Intraocular Lens Selection in Refractive Cataract Surgery," Ophthalmology, vol. 128:e142-e152 (2021).
Goyal, S. et al., "Preoperative Orthokeratology and Corneal Collagen Cross-Linking in Keratoconus: An Exploratory Randomised Clinical Trial," Invest. Ophthalmol. Vis. Sci., vol. 50(13):5482 (2009).

Leibowitz HM, et al., "Evaluation of dexamethasone acetate as a topical ophthalmic formulation," Am J Ophthalmol., vol. 86:418-423 (1978).
Lindstrom RL et al, "Corneal inlays for presbyopia correction," Curr Opin Ophthalmol., vol. 24:281-287 (2013).
Macsai MS, et al., "Refractive enhancement following presbyopia-correcting intraocular lens implantation," Curr Opin Ophthalmol., vol. 19:18-21 (2008).
Parentin F. et al., "Central corneal thickness in children with growth hormone deficiency," Acta Ophthalmol., vol. 88:692-694 (2010).
Piovella M. et al., "Excimer laser photorefractive keratectomy for high myopia: four-year experience with a multiple zone technique," Ophthalmology, vol. 104:1554-1565 (1997).
Rohdewald P, et al., "Pharmacokinetics of dexamethasone and its phosphate ester," Biopharm Drug Dispos., vol. 8:205-212 (1987).
Sorkin N., et al., "Corneal collagen crosslinking: a systematic review," Ophthalmologica, vol. 232(1):10-27 (2014).
Swarbrick HA, "Orthokeratology (corneal refractive therapy): what is it and how does it work?" Eye Contact Lens, vol. 30(4):181-185 (2004).
Thajudeen, B. et al., "Corneal dystrophies simplified," Eye News, vol. 23(5): 3 pages (2017).
Vazirani J, et al., "Keratoconus: current perspectives," Clin Ophthalmol., vol. 7:2019-2030 (2013).
Volatier TLA, et al., "Keratoconus at a Molecular Level: A Review," Anat Rec (Hoboken), vol. 303:1680-1688 (2020).
Website—https://www.myopiaprofile.com/should-i-fit-orthok-to-a-potential-keratoconic/ published Jun. 8, 2020, accessed Jan. 24, 2023—8 pages.
Yamada, Y.et al., "OSEIRT/Ortho-K Indication for the Keratoconus Patients ," Invest. Ophthalmol. Vis. Sci., vol. 46(13):4953 (2005).

* cited by examiner

Fig. 8A
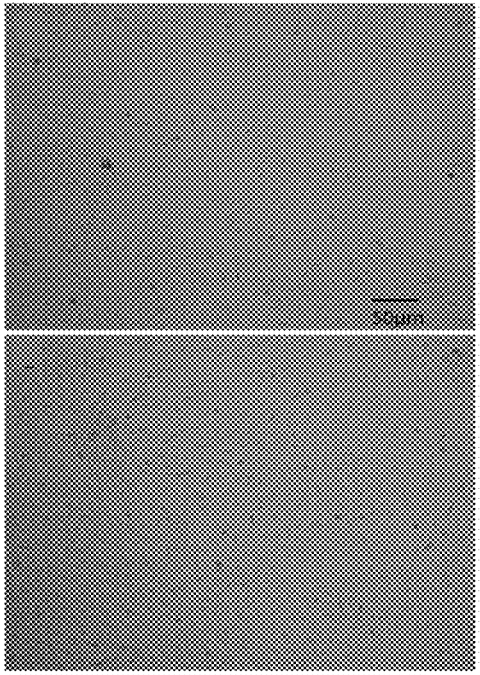
Fig. 8B
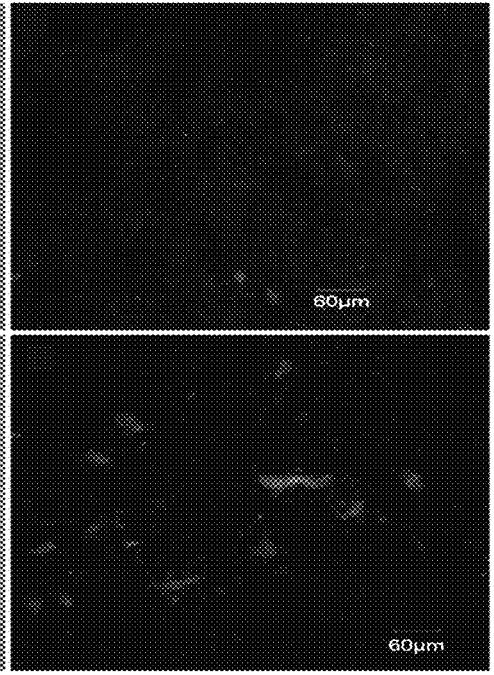
Fig. 8C
Fig. 8D
Fig. 8E
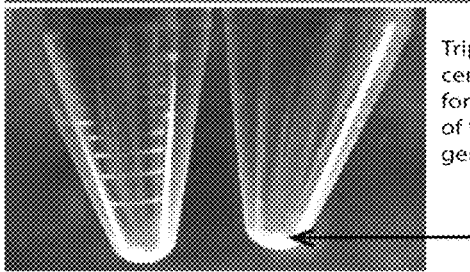
Tripsinised corneal fibroblasts were pelleted by centrifufing at 12,00 rpm for 7 mins. The cells formed a mass that did not adhere to the walls of the tube. The pellet was cultured in chondrogenic diffrentiation medium for 3 weeks.
— cell pellet(approximately 0.8mm in diameter)
Fig. 8F
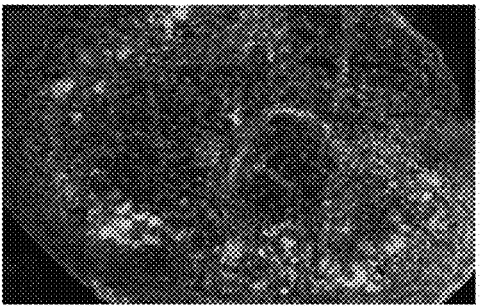
Fig. 8G
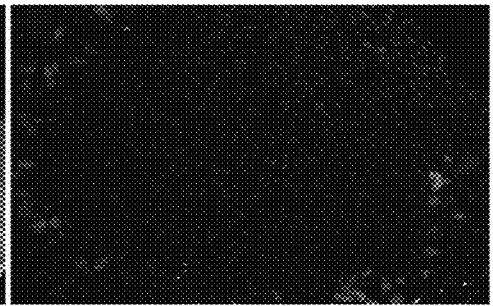

Fig. 9A 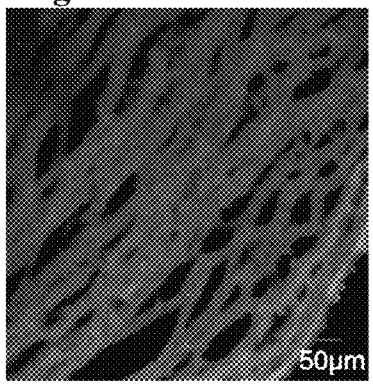 Fig. 9B 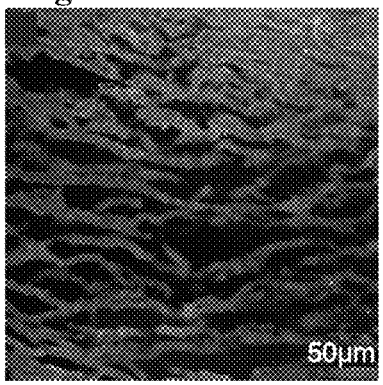 Fig. 9C 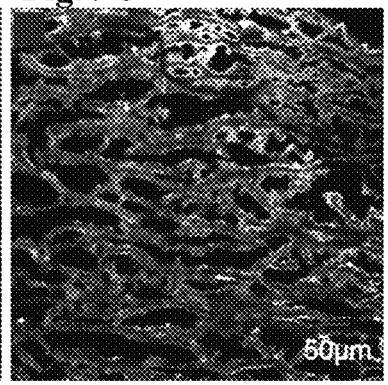
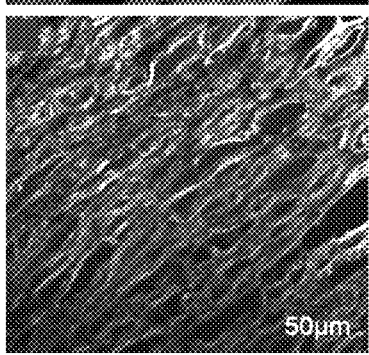 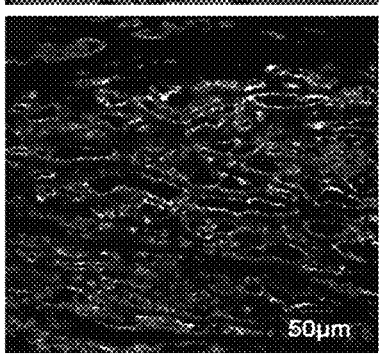 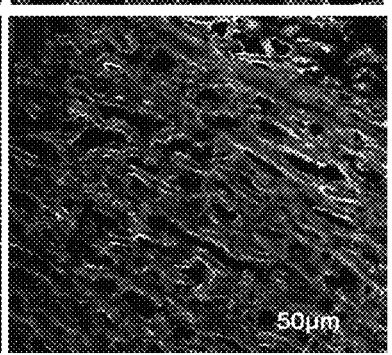
Fig. 9D Fig. 9E Fig. 9F Fig. 10A
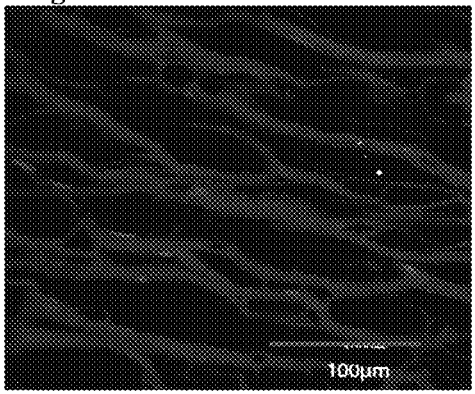
Fig. 10B
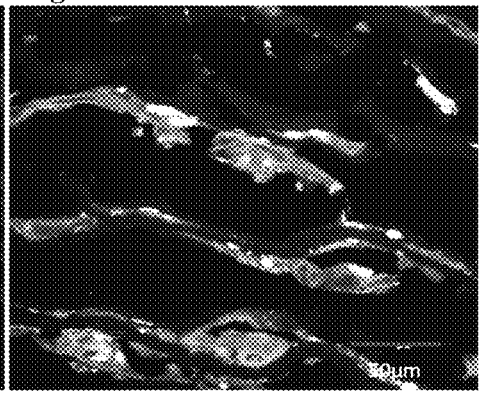
Fig. 10C
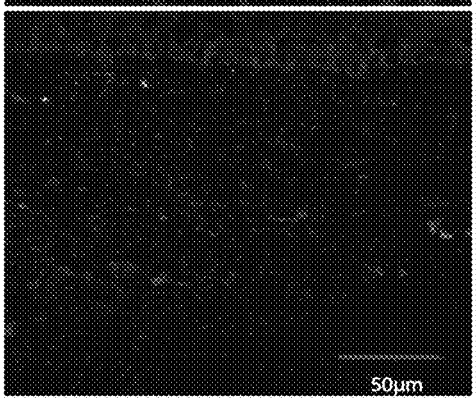
Fig. 10D
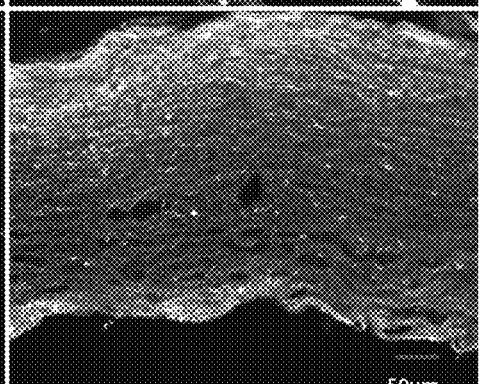
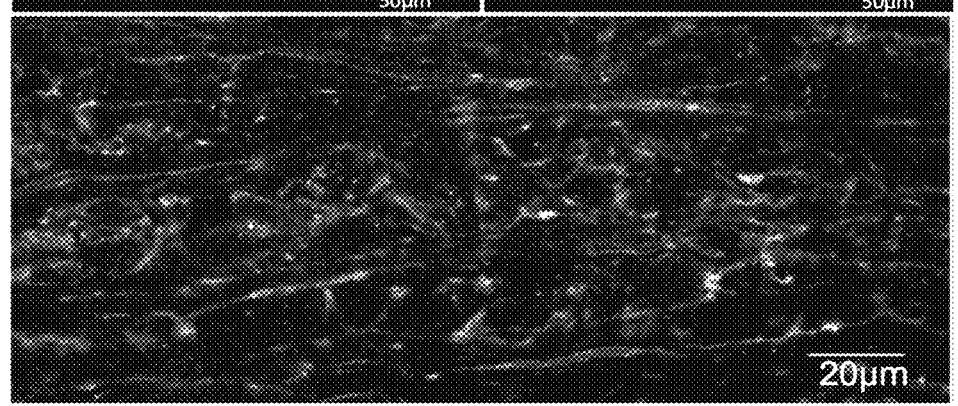
Fig. 10E Fig. 14A
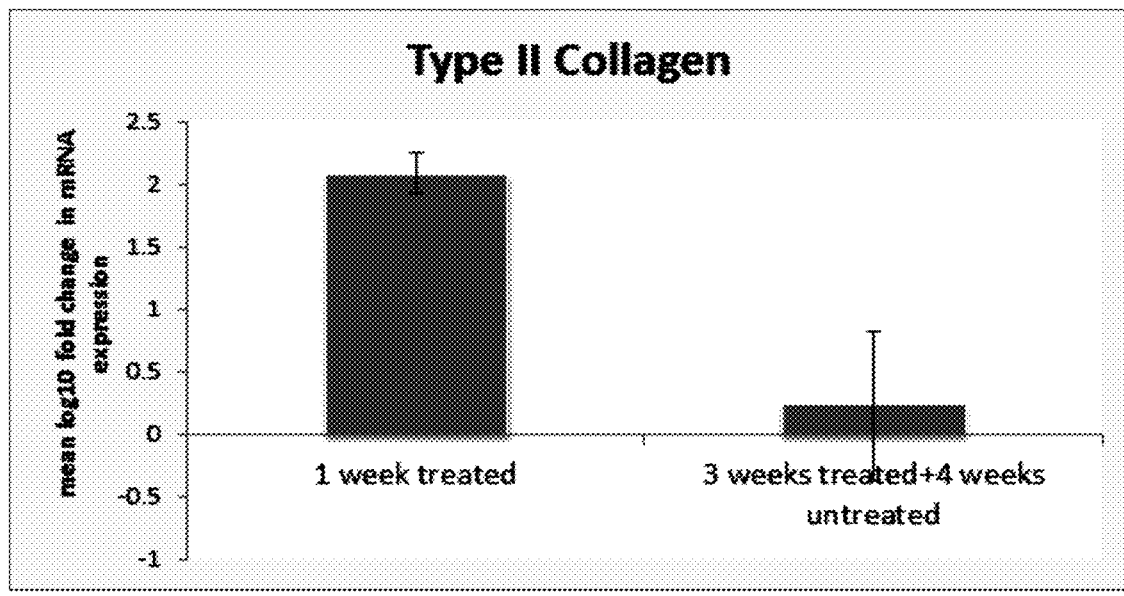
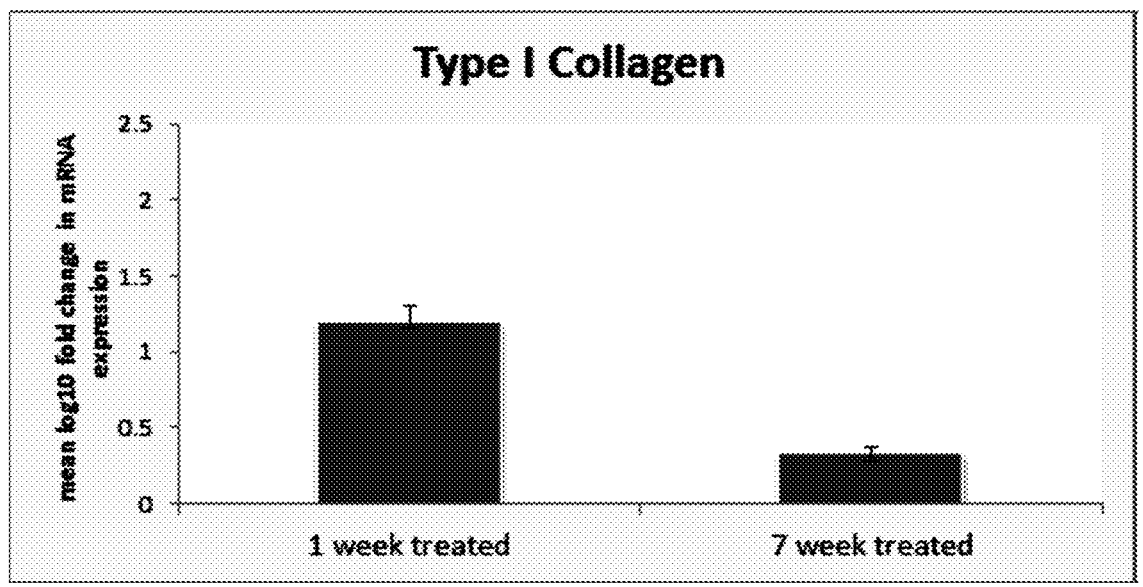
Fig. 14B Fig. 16A  Treated Rat Globe Fig. 16B  Treated Rat Globe Fig. 16C  Untreated Rat Globe Fig. 16D  Untreated Rat Globe Fig. 17
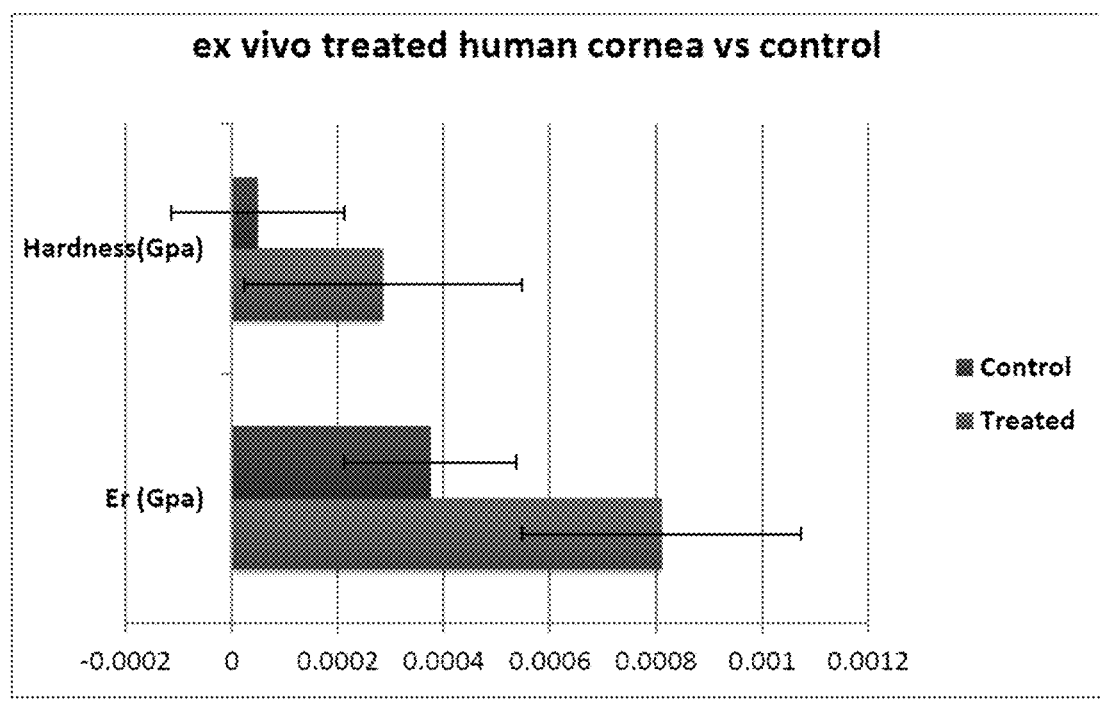
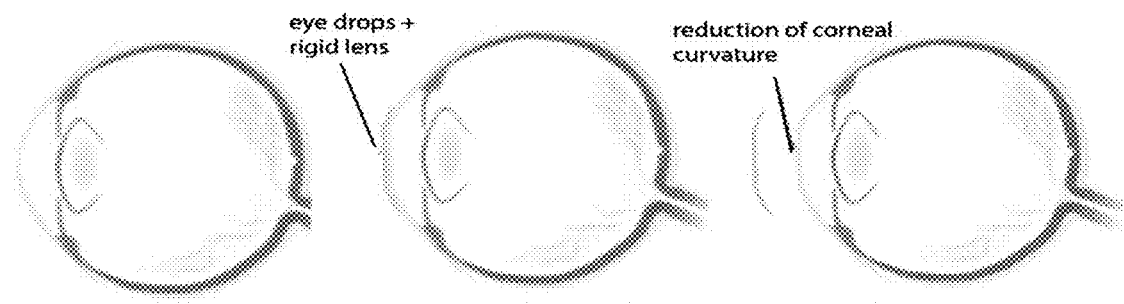
Before Treatment
Fig. 18A
During Treatment
Fig. 18B
After Treatment
Fig. 18C

OPHTHALMIC COMPOSITIONS AND METHODS OF USE THEREFOR

RELATED APPLICATION

This application is a continuation of U.S. patent application Ser. No. 15/555,909, filed Sep. 5, 2017, now U.S. Pat. No. 10,842,850, which is the U.S.C. § 371 filing of International Application No. PCT/NZ2016/050033, filed on Mar. 4, 2016, which claims the benefit of New Zealand Patent Application No. 705727, filed on Mar. 5, 2015. The entire contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Oct. 23, 2020, is named ILJ_002USCN_Sequence_Listing.txt and is 1,464 bytes in size.

FIELD OF THE INVENTION

The present disclosure relates to compositions and methods useful for the treatment and/or prevention of conditions of the eye. In particular, the disclosure relates to compositions and methods that can be used in augmenting and regenerating the cornea, and in correcting refractive errors of the eye.

BACKGROUND OF THE INVENTION

It was previously believed that differentiated cells relinquished their ability to regress to an earlier state. However, this view has been challenged by the induction of pluripotent stem cells (cell reprogramming) and evidence showing that differentiated cells can switch to another phenotype (Takahashi & Yamanaka 2006; Wernig et al. 2007; Yamanaka & Blau 2010; Gurdon & Melton 2008; Peran et al. 2011). In addition, it is now believed that the microenvironment for cells, which includes the surrounding cells, extracellular matrix, and growth and differentiation factors, plays an important role in bringing about the redirection of cellular differentiation (Høkelien and Collas 2002). With this information, researchers have begun to develop therapeutics that utilise cell reprogramming and stem cell technologies.

The cornea of the eye accounts for more than two-thirds of the eye's total refractive power (focusing power). Even small changes in corneal shape can have a dramatic effect on the clarity with which an image is brought to focus on the retina. The stromal layer of the cornea (the clear front surface of the eye) comprises the majority of the corneal tissue and is composed of highly organised lamellae which are made up of tightly packed collagen fibrils, mostly of collagen types I and V (Marshall et al. 1993). The unique structure of the stromal layer as a result of the uniform alignment of the collagen fibrils confers the properties of toughness and transparency on the cornea (Funderburgh 2000).

When stromal cells (the corneal keratocytes) are removed from the cornea and cultured in a monolayer they exhibit the morphological characteristics of fibroblasts and switch from a stellate shaped cell to a multinucleate, fusiform shaped cell (Funderburgh et al. 2001). Another commonly observed phenotype of keratocytes is the myofibroblast form that is seen in the cornea after injury (Jester et al. 1987). Changes in exogenous growth factors and cytokines are thought to bring about these phenotypic changes (Funderburgh et al. 2001).

TGFβ family of growth factors are known to be the most potent inducers of chondrogenic (cartilage) differentiation (Heng, Cao, & Lee 2004; Johnstone et al. 1998; Menetrey et al. 2000). TGFβ1 stimulates the synthesis of collagens and fibronectin by chick embryo fibroblasts (Ignotz and Massague 1986). For keratocytes, TGFβ1 and TGFβ2 are known to cause ECM deposition associated with scarring, possibly due to conversion of keratocytes into the myofibroblast phenotype (Funderburgh, Mann, Funderburgh, Corpuz, & Roth 2001). In contrast, TGFβ3 has been shown to induce corneal fibroblasts to produce ECM depositions made up of collagen type I without fibrosis or scarring (Karamichos, Hutcheon, & Zieske 2011). Certain non-proteinaceous chemical compounds such as dexamethasone (Johnstone, Hering, Caplan, Goldberg, & Yoo 1998), ascorbic acid (Farquharson, Berry, Barbara Mawer, Seawright, & Whitehead 1998), and ethanol (Kulyk & Hoffman 1996) are also known to promote chondrogenic differentiation in vitro.

There are a number of conditions affecting the cornea, including various defects, injuries, diseases, and degenerative conditions. Myopia results from excessive curvature of the cornea so that light entering the eye focuses in front of the retina. It is the most prevalent vision impairment worldwide affecting the vision of 70 to 90% of people in some Asian countries and 30 to 40% in Europe and the United States (Frederick 2002). In most cases, myopia first occurs in school-age children and progresses until about the age of 20. It is also associated with increased prevalence of macular degeneration, retinal detachment, and glaucoma in adulthood (Ebenstein & Pruitt 2006).

Myopia is most commonly corrected by the use of prescription eye glasses or contact lenses. However, these devices do not provide permanent treatment for the condition, and they are unsuitable for use during certain activities. Contact lenses are also associated with ophthalmic infections and more serious conditions, including corneal abrasions and ulcers. In certain circumstances, refractive surgery or orthokeratology is indicated for myopia. Still, these treatments provide only a temporarily correction for mild to moderate myopia; they are not permanent treatments, and they are unsuitable for severe cases.

Keratoconus is an ecstatic corneal dystrophy associated with stromal thinning and disruption of the portion of the cornea known as Bowman's layer. The progressive thinning of the corneal stroma typically occurs over decades and results in the cornea developing a conical shape. This results in an impairment of vision due to irregular astigmatism and myopia. The pathogenesis of keratoconus is still unknown but has been associated with factors such as constant eye rubbing and contact lens wear (Krachmer, Feder, & Belin 1984; Sherwin & Brookes 2004). It can appear as early as puberty and continues to progress until the third or fourth decade of life.

The incidence of keratoconus has been estimated at approximately 1 in 2000 in the general population worldwide (Rabinowitz 1998), with no predilection for either gender. Since the onset of keratoconus is typically in early adulthood with continuation into prime earning and child-rearing years, the loss of quality of life and the economic burden of the treatment of keratoconus represent a significant public health concern. Keratoconus is a major indication for cornea transplantation in the Western world, determined by researchers to constitute 28.8% of corneal transplantation in France (Legeais et al. 2001) and from 11.4% to 15.4% in the United States (Cosar et al. 2002; Dobbins et al. 2000). There is an unusually high prevalence of keratoconus in New Zealand, with a disproportionately high incidence in Pasifika and Maori populations (Patel et al. 2005; Patel & McGhee 2013). In New Zealand, approximately 50% of all corneal transplants performed are for keratoconus (Edwards et al. 2002).

Despite several studies on keratoconus, the underlying biochemical process remains poorly understood. The familial occurrence of keratoconus suggests that one of the aetiological factors is genetic (Ihalainen 1985). The condition has also been linked to certain biochemical and biomechanical factors. For example, it has been determined that the corneal thinning of keratoconus is a result of the loss of extracellular matrix (ECM) components. However, this could be due to their destruction, their defective formation, or a combination of these (Klintworth & Damms 1995; Klintworth 1999; Jhanji et al. 2011). In the corneal stroma, changes associated with keratoconus include a decrease in the number of lamellae and keratocytes (Ku, Niederer, Patel, Sherwin, & McGhee 2008; Sherwin & Brookes 2004), and changes in organisation of the lamellae and distribution of collagen fibrillary mass (Meek et al. 2005).

It is thought that the degradation of the stromal layer might be due to aberrant proteolytic enzyme activity (Fukuchi, Yue, Sugar, & Lam 1994). Keratoconus corneas are known to have decreased levels of enzyme inhibitors and an increased level of degradative enzymes (Kenney & Brown 2003). Biomechanical factors include thinning and decreased rigidity of the cornea due to oxidative damage caused by ultraviolet radiation and mechanical trauma (Kenney & Brown 2003). Biomechanical investigation of keratoconic corneas has revealed a decrease in elasticity and stiffness; however the reasons for this remain unknown (Edmund 1988). It has been suggested that a reduction in collagen cross-links could be a cause (Wollensak & Buddecke 1990). Currently there is no satisfactory animal model for keratoconus and investigations have been largely limited to an ex vivo setting.

Depending on the severity of the condition, attempts to slow progression of keratoconus include the use of special spectacles and contact lens. In severe cases, corneal implants, intrastromal rings, or corneal transplants are necessary (Jhanji, Sharma, & Vajpayee 2011). Penetrating keratoplasty, a procedure in which the entire thickness of the cornea is removed and replaced by donor corneal tissue, is the most commonly used surgical procedure used to treat advanced cases of keratoconus (Rabinowitz 1998). Keratoconus is the leading indication for corneal transplantation surgery worldwide, with about 12-20% of those affected by keratoconus requiring a corneal transplant (Pramanik, Musch, Sutphin, & Farjo 2006).

Early treatment options for keratoconus, such as customised gas permeable lenses known as Rose K lenses, have been focussed on improving visual acuity. Newer treatments aim to slow the progression of the disease. A treatment known as corneal collagen cross-linking (CXL) looks at increasing corneal rigidity and biomechanical stability. In this procedure, the epithelium is debrided, topical riboflavin drops are administered, and the corneas are exposed to ultraviolet-A light at 370 nm for approximately 30 minutes (Ashwin & McDonnell 2010; G. Wollensak, Spoerl, & Seiler 2003). It is believed that the UV-A light activates the riboflavin thereby producing reactive oxygen species that induce the formation of covalent bonds between the collagen molecules in the corneal stroma (Spoerl, Huhle, & Seiler 1998; G. Wollensak et al. 2003). This procedure, however, is not recommended for the treatment of corneas thinner than 400 μm due to the possibility of endothelial cell damage. Although this treatment leads to a stiffer cornea, it does not address the problem of corneal thinning.

Therefore, there is an ongoing need for therapeutic compositions and methods for addressing conditions of the eye, including conditions affecting the cornea. There is a particular need for therapies that are relatively non-invasive and readily administered.

SUMMARY OF THE INVENTION

The inventors have developed compositions and methods for modulating corneal cells, to alter collagen expression and extracellular matrix formation in corneal tissue. These compositions and methods are useful for regenerating and/or augmenting the cornea, and thereby treating and/or preventing various conditions of the cornea and refractive errors of the eye.

In one aspect, the invention comprises a method of treating or preventing a condition associated with a thinning or irregularity of a cornea, comprising: contacting the cornea with a composition comprising a TGFβ3 polypeptide or a variant or fragment thereof, and dexamethasone or derivative thereof or related steroidal agent, thereby treating or preventing the condition.

In various aspects:

The TGFβ3 polypeptide consists of the amino acid sequence of SEQ ID NO:1.

The dexamethasone is dexamethasone phosphate.

The composition comprises 10 to 100 ng/ml of the TGFβ3 polypeptide.

The composition comprises 40 to 4000 ng/ml dexamethasone.

The composition is formulated as an eye drop.

The composition is formulated with gellan gum.

The composition is administered once daily or twice daily.

The composition is co-administered with one or more additional agents for the eye.

The one or more additional agents for the eye are selected from the group consisting of: anaesthetic agents, anti-inflammatory agents, anti-microbial agents, and lubricants.

The composition is administered in conjunction with use of a contact lens, corneal insert, corneal implant, or intrastromal ring.

The contact lens, corneal insert, corneal implant, or intrastromal ring is adapted for moulding or holding corneal shape during and/or following treatment with the composition.

The contact lens, corneal insert, corneal implant, or intrastromal ring is adapted to act as a carrier for the composition or as a composition eluting device.

The composition is administered in conjunction with corneal collagen crosslinking.

The administration of the composition is prior to and/or subsequent to crosslinking.

The condition is selected from the group consisting of: keratoconus, myopia, and astigmatism.

In an alternative aspect, the method comprises co-administration of a composition comprising the TGFβ3 polypeptide or a variant or fragment thereof, and a composition comprising the dexamethasone or derivative thereof or related steroidal agent.

In one further aspect, the invention comprises a method of treating or preventing damage or injury of a cornea, comprising: contacting the cornea with a composition comprising a TGFβ3 polypeptide or a variant or fragment thereof, and dexamethasone or derivative thereof or related steroidal agent, thereby treating or preventing the damage or injury of the cornea.

In various aspects:

The TGFβ3 polypeptide consists of the amino acid sequence of SEQ ID NO:1.

The dexamethasone is dexamethasone phosphate.

The composition comprises 10 to 100 ng/ml of the TGFβ3 polypeptide.

The composition comprises 40 to 4000 ng/ml dexamethasone.

The composition is formulated as an eye drop.

The composition is formulated with gellan gum.

The composition is administered once daily or twice daily.

The composition is co-administered with one or more additional agents for the eye.

The one or more additional agents for the eye are selected from the group consisting of: anaesthetic agents, anti-inflammatory agents, anti-microbial agents, and lubricants.

The composition is administered in conjunction with use of a contact lens corneal insert, corneal implant, or intrastromal ring.

The contact lens, corneal insert, corneal implant, or intrastromal ring is adapted for moulding or holding corneal shape during and/or following treatment with the composition.

The contact lens, corneal insert, corneal implant, or intrastromal ring is adapted to act a carrier for the composition or as a composition eluting device.

The damage or injury of the cornea is associated with one or more of: an abrasion, tear, ulcer, burn, puncture, and surgery.

In an alternative aspect, the method comprises co-administration of a composition comprising the TGFβ3 polypeptide or a variant or fragment thereof, and a composition comprising the dexamethasone or derivative thereof or related steroidal agent.

In yet a further aspect, the invention comprises a method of treating or preventing a refractive error of the eye, comprising: contacting they eye with a composition comprising a TGFβ3 polypeptide or a variant or fragment thereof, and dexamethasone or derivative thereof or related steroidal agent, thereby treating or preventing the refractive error of the eye.

In various aspects:

The TGFβ3 polypeptide consists of the amino acid sequence of SEQ ID NO:1.

The dexamethasone is dexamethasone phosphate.

The composition comprises 10 to 100 ng/ml of the TGFβ3 polypeptide.

The composition comprises 40 to 4000 ng/ml dexamethasone.

The composition is formulated as an eye drop.

The composition is formulated with gellan gum.

The composition is administered once daily or twice daily.

The composition is co-administered with one or more additional agents for the eye.

The one or more additional agents for the eye are selected from the group consisting of: anaesthetic agents, anti-inflammatory agents, anti-microbial agents, and lubricants.

The composition is administered for use in conjunction with a contact lens, corneal insert, corneal implant, or intrastromal ring.

The contact lens, corneal insert, corneal implant, or intrastromal ring is adapted for moulding or holding corneal shape during and/or following treatment with the composition.

The contact lens, corneal insert, corneal implant, or intrastromal ring is adapted to act as a carrier for the composition or as a composition eluting device.

The method is performed preceding or following refractive surgery.

The refractive error of the eye is associated with one or more of: myopia, hyperopia, astigmatism, and presbyopia.

In an alternative aspect, the method comprises co-administration of a composition comprising the TGFβ3 polypeptide or a variant or fragment thereof, and a composition comprising the dexamethasone or derivative thereof or related steroidal agent.

In still a further aspect, the invention encompasses a kit comprising:

a composition comprising a TGFβ3 polypeptide or a variant or fragment thereof, and dexamethasone or derivative thereof or related steroidal agent; and one or more contact lenses.

In various aspects:

The contact lens, corneal insert, corneal implant, or intrastromal ring is adapted for moulding or holding corneal shape during and/or following treatment with the composition.

The contact lens, corneal insert, corneal implant, or intrastromal ring act as a carrier for the composition or as a composition eluting device.

The TGFβ3 polypeptide consists of the amino acid sequence of SEQ ID NO:1.

The dexamethasone is dexamethasone phosphate.

The composition comprises 10 to 100 ng/ml of the TGFβ3 polypeptide.

The composition comprises 40 to 4000 ng/ml dexamethasone.

The composition is formulated as an eye drop.

The composition is formulated with gellan gum.

The composition is formulated for administration once daily or twice daily.

The composition is co-formulated with one or more additional agents for the eye.

The kit includes one or more additional agents for the eye.

The one or more additional agents for the eye are selected from the group consisting of: anaesthetic agents, anti-inflammatory agents, anti-microbial agents, and lubricants.

The kit includes a contact lens solution.

The kit includes instructions for use.

The kit is used for the treatment or prevention of a refractive error of the eye.

The kit is used for the treatment or prevention of a corneal condition selected from the group consisting of: keratoconus, myopia, hyperopia, astigmatism, presbyopia, and stromal dystrophies.

The kit is used for the treatment of a corneal condition selected from the group consisting of: an abrasion, tear, ulcer, burn, puncture, corneal melt, and surgical injury.

In an alternative aspect, the kit comprises as separate components a composition comprising the TGFβ3 polypeptide or a variant or fragment thereof, and a composition comprising the dexamethasone or derivative thereof or related steroidal agent.

In even a further aspect, the invention comprises a method of inducing collagen type II expression in a keratocyte, comprising: contacting the keratocyte with a composition comprising a TGFβ3 polypeptide or a variant or fragment thereof, and dexamethasone or derivative thereof or related steroidal agent, thereby inducing collagen type II expression in the keratocyte.

In various aspects:

The TGFβ3 polypeptide consists of the amino acid sequence of SEQ ID NO:1.

The dexamethasone is dexamethasone phosphate.

The composition comprises 10 to 100 ng/ml of the TGFβ3 polypeptide.

The composition comprises 40 to 4000 ng/ml dexamethasone.

The composition is formulated for administration via a contact lens, a corneal insert, a corneal implant, or an intrastromal ring.

The composition is formulated for administration as a solution, gel, cream, or emulsion.

The method is performed in vivo.

The method is performed ex vivo.

In an alternative aspect, the method comprises co-administration of a composition comprising the TGFβ3 polypeptide or a variant or fragment thereof, and a composition comprising the dexamethasone or derivative thereof or related steroidal agent.

The foregoing brief summary broadly describes the features and technical advantages of certain embodiments of the present invention. Further technical advantages will be described in the detailed description of the invention and examples that follows.

Novel features that are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to limit the invention's scope.

BRIEF DESCRIPTION OF THE DRAWINGS

FIG. 8A: Corneal keratocytes seeded in serum containing fibroblast proliferating medium, and cultured in control fibroblast proliferation medium for 3 weeks were negative for nestin.

FIG. 8B: Corneal keratocytes seeded in serum containing fibroblast proliferating medium, and cultured in control fibroblast proliferation medium for 3 weeks were negative for collagen Type II.

FIG. 8C: Confluent fibroblasts were then cultured in chondrogenic differentiation medium containing TGFβ3 and dexamethasone for 3 weeks.

FIG. 8D: The cells remained negative for collagen type II).

FIG. 8E: Pellet culture of confluent fibroblasts in chondrogenic differentiation medium.

FIG. 8F: After 3 weeks in culture the cell pellet was sectioned and labelled positive for the keratocyte marker keratocan.

FIG. 8G: After 3 weeks in culture the cell pellet was sectioned and labelled negative for the chondrocyte specific type II collagen.

FIG. 9A: Human corneal slices cultured for 2 weeks in control medium were negative for type II collagen.

FIG. 9B: Human corneal slices cultured for 1 week in chondrogenic differentiation medium and labelled for collagen type II.

FIG. 9C: Human corneal slices cultured for 2 week in chondrogenic differentiation medium and labelled for collagen type II.

FIG. 9D: Human corneal slices cultured for 2 weeks in control medium were positive for type I collagen.

FIG. 9E: Human corneal slices cultured for 1 week in chondrogenic differentiation medium and labelled for collagen type I.

FIG. 9F: Human corneal slices cultured for 2 weeks in chondrogenic differentiation medium and labelled for collagen type I. Strong labelling for type II collagen was seen in corneal slices treated for 2 weeks whereas slices treated for only 1 week were negative for type II collagen. Slices cultured in chondrogenic differentiation medium for both the time periods, although less strongly labelled when compared to the control treated slices, were positive for the native corneal collagen type I.

FIG. 10A: Human corneal slices cultured for 2 weeks in control medium.

FIG. 10B: Human corneal slices cultured for 2 weeks in chondrogenic differentiation medium and labelled for collagen type II. Similar results were obtained as shown by FIG. 9.

FIG. 10C: In vivo experiments showing untreated corneas.

FIG. 10D and FIG. 10E: treated corneas with a widespread labelling of type II collagen in the TGFβ3 and dexamethasone treated corneas of rats. In FIG. 10D, stronger labelling was seen in the anterior (upper) part of the cornea. Type II collagen appeared fibrillar and was evenly distributed throughout the ECM.

FIG. 14A: Quantitative gene expression of collagen type II in in vivo treated corneas.

FIG. 14B: Quantitative gene expression of collagen type I in in vivo treated corneas. There was an initial increase in type II collagen expression upon after 1 week of treatment. Upon withdrawal of the treatment there was a marked decrease in type II collagen expression, (FIG. 14A). Native corneal collagen type I expression was also initially upregulated, however upon long term treatment (up to 7 weeks) its expression was comparable to the control untreated cornea, (FIG. 14B).

FIG. 16A and FIG. 16B: Load deformation curves obtained for 3 week in vivo treated corneas from two rates.

FIG. 16C and FIG. 16D: Load deformation curves obtained for 3 week in vivo untreated corneas from two rats.

FIG. 17: Comparison of elastic modulus and hardness of 8 week treated and control human keratoconic cornea reveals a marked increase in both parameters in the treated cornea.

FIG. 18A: Reshaping of the cornea in the sheep eye by combining in vivo cell reprogramming with a rigid contact lens to hold the desired corneal shape before treatment.

FIG. 18B: Reshaping of the cornea in the sheep eye by combining in vivo cell reprogramming with a rigid contact lens to hold the desired corneal shape during treatment.

FIG. 18C: Reshaping of the cornea in the sheep eye by combining in vivo cell reprogramming with a rigid contact lens to hold the desired corneal shape after treatment.

DETAILED DESCRIPTION OF THE INVENTION

Figure 1A:
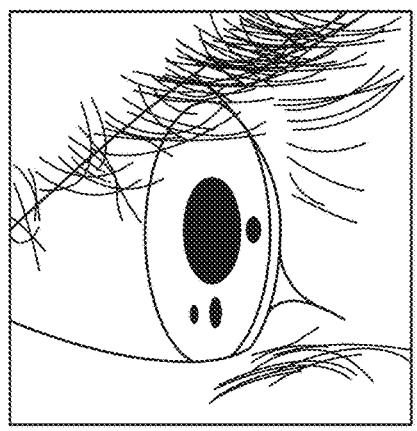
FIG. 1A: View of a normal cornea.

The following description sets forth numerous exemplary configurations, parameters, and the like. It should be recognised, however, that such description is not intended as a limitation on the scope of the present invention, but is instead provided as a description of exemplary embodiments.

Definitions

In each instance herein, in descriptions, aspects, embodiments, and examples of the present invention, the terms "comprising", "including", etc., are to be read expansively, without limitation. Thus, unless the context clearly requires otherwise, throughout the description and the claims, the words "comprise", "comprising", and the like are to be construed in an inclusive sense as to opposed to an exclusive sense, that is to say in the sense of "including but not limited to".

As used herein, "augmenting" refers to methods of increasing one or more of the thickness, hardness, elastic modulus, tensile strength, and regularity of the cornea, including the corneal tissue (e.g., the stromal layer). Augmentation may be used to impose a particular shape to the cornea, i.e., corneal curvature. Augmentation methods may be performed in the presence or absence of a particular condition of the eye, or of the cornea. Augmentation may involve the increase in components in the extracellular matrix of the cornea (e.g., collagen type II). Augmentation may also involve increasing the number of cells (e.g., keratocytes) in the cornea. The number of cells may be increased, for example, by altering the proliferative state of such cells from quiescent to active.

"Co-administration" or "co-administering" refers to the combined use of agents, for example, therapeutic agents for the eye, and includes the administration of co-formulations (i.e., combination formulations), as well as the simultaneous or sequential administration of separate formulations. Similarly, "in conjunction" refers to the combined use of a therapeutic composition and a therapeutic device/procedure. This can include use of the composition preceding use of the device/procedure, simultaneously with the device/procedure, and/or following use of the device/procedure.

A "condition" of the cornea refers to a state of disease, defect, damage, injury, degeneration, or dysfunction of the cornea. The condition may affect the corneal tissue (e.g., the stromal layer) or corneal cells (e.g., keratocytes). The condition may be an acute condition, for example, an abrasion or ulceration, or may be a chronic condition, for example, keratoconus or myopia.

The "cornea" as used herein refers to the transparent front part of the eye that covers the iris, pupil, and anterior chamber of the eye. It includes the corneal epithelium, Bowman's layer, corneal stroma, Descemet's membrane, and the corneal epithelium. Of particular interest is the stromal layer (also called the substantia propria) of the cornea, which comprises an extracellular matrix of regularly arranged collagen fibres along with keratocytes, A "derivative", as relating to a chemical derivative, refers to a compound that has been chemically modified. The present disclosure encompasses each of the chemical compounds described herein as well as any derivatives thereof, including chemically modified forms such as salts, hydrides, esters, and other modifications of the original compound.

"Isolated" as used herein, with particular reference to polypeptides, refers to a molecule that is separated from its natural environment. An isolated molecule may be obtained by any method or combination of methods as known and used in the art, including biochemical, recombinant, and synthetic techniques. To obtain isolated components, the polypeptides may be prepared by at least one purification or enrichment step. Of particular interest are polypeptides and peptides obtained by artificial means, i.e., non-natural, means. This includes but is not limited to, synthetic chemistry, recombinant technology, purification protocols, etc. Included are polypeptides isolated from natural, recombinant, or synthetic sources. Also included are polypeptides produced by chemical synthesis, or by plasmids, vectors, or other expression constructs that may be introduced into a cell or cell-free translation system. Such polypeptides are clearly distinguished from polypeptides as they naturally occur, without human intervention.

The terms "protein" or "polypeptide" (e.g., SEQ ID NO:1), and other such terms, for simplicity, refer to the molecules described herein. Such terms are not meant to provide the complete characterization of these molecules. Thus, a protein or polypeptide may be characterised herein as having a particular amino acid sequence, a particular 2-dimensional representation of the structure, but it is understood that the actual molecule claimed has other features, including 3-dimensional structure, mobility about certain bonds and other properties of the molecule as a whole. It is the molecules themselves and their properties as a whole that are encompassed by this disclosure. The terms "protein" and "polypeptide" are used interchangeably herein.

A TGFβ3 "polypeptide" refers to polypeptides obtained from any source, e.g., isolated naturally occurring polypeptides, recombinant polypeptides, and synthetic polypeptides, and to include polypeptides having the naturally occurring amino acid sequence as well as polypeptides having variant amino acid sequences, and fragments of such sequences, as described in detail herein. TGFβ3 may also be referred to in the art as transforming growth factor-beta3, TGFB3, ARVD, and FLJ16571.

Amino acid "sequence identity" refers to the amino acid to amino acid comparison of two or more polypeptides. A test sequence may be identical to a reference sequence (i.e., share 100% identity), or may include one or more amino acid substitutions. In preferred aspects, amino acid substitutions may possess similar chemical and/or physical properties such as charge or hydrophobicity, as compared to the reference amino acid. Sequence identity may be typically determined by sequence alignments at the regions of highest homology. Sequence alignment algorithms, for example BLAST® sequence alignment programs, are well known and widely used in the art. Based on the sequence alignment, the percent identity can be determined between the compared polypeptide sequences.

A "refractive error" as used herein, refers to error in the focusing of light by the eye. Refractive errors may include spherical errors and cylindrical errors. Both lower order aberrations and higher order aberrations are included. Specifically included as refractive errors are the conditions of the eye noted as myopia, hyperopia, astigmatism, anisometropia, and presbyopia.

"Regeneration", in relation to the cornea, refers to the restoration of one or more of the shape, thickness, regularity, hardness, elastic modulus, and tensile strength of the cornea, including that of the corneal tissue (e.g., the stromal layer). Methods of regeneration may be used to impose a particular shape to the cornea, i.e., corneal curvature. Regeneration methods may be performed in the treatment of a particular condition of the eye, or of the cornea. Regeneration may involve the increase in components in the extracellular matrix of the cornea (e.g., collagen type II). Regeneration may also involve increasing the number of cells (e.g., keratocytes) in the cornea. The number of cells may be increased, for example, by altering the proliferative state of such cells from quiescent to active.

"Reprogramming" of cells, for example, for corneal cells (e.g., keratocytes) refers to changes in the state of differentiation. Reprogramming is associated with one or more changes in cell morphology, cellular gene expression (e.g., collagen expression, including collagen type I and/or type II expression), or the cells proliferative state (e.g., quiescent or active).

The term "subject" refers to a human or non-human animal.

"Preventing" refers to stopping or delaying the onset of a condition, for example an eye condition, or particularly a corneal condition, such as a disorder or other defect of the cornea. A preventative measure will result in the stoppage or delay of one or more symptoms of the condition, or a lessening of symptoms if such do arise. Prevention of a corneal condition may involve augmenting the cornea, as described in detail herein.

"Treating" refers to reducing, ameliorating, or resolving a condition, for example an eye condition, or particularly a corneal condition, such as a disorder or other defect of the cornea. A treatment will result in the reduction, amelioration, or elimination of one or more symptoms of the condition. Treatment of a corneal condition may involve regeneration of the cornea, as detailed herein. The compositions and methods of the invention may be used for treating various conditions, for preventing various conditions, or for both treating and preventing various conditions, as described in detail herein.

Cell and Tissue Regeneration

Cell and tissue regeneration technologies hold considerable promise in therapeutic treatments. As disclosed herein, the inventors have developed compositions and methods for modulating cells using in situ cell reprogramming in order to affect collagen type II expression and extracellular matrix (ECM) deposition in corneal tissue. This, in turn, is used to strengthen and/or augment the cornea of the eye. The inventors thereby provide a unique approach for the in situ I in vivo regeneration and augmentation of the corneal stromal matrix.

Figure 1B:
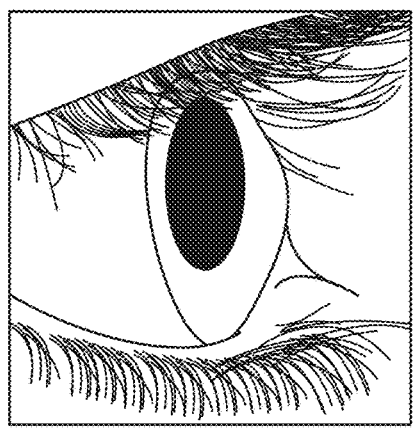
FIG. 1B: View of a keratoconic cornea.
Figure 1C:
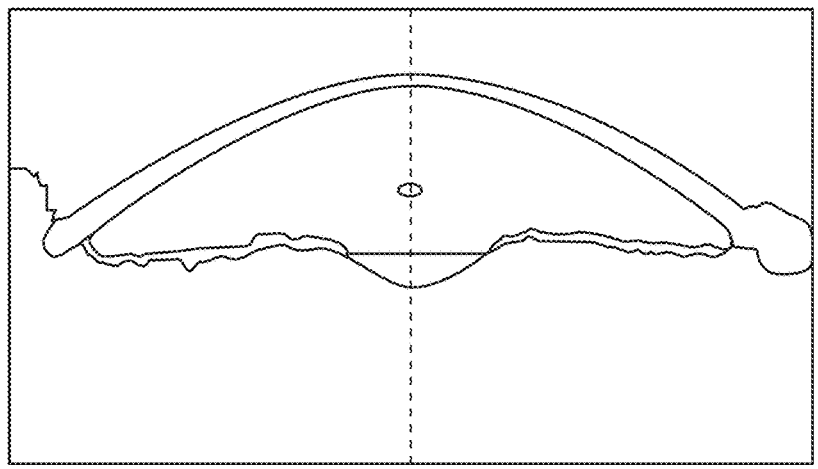
FIG. 1C: Scheimpflug image in severe keratoconus. Significant corneal thinning is appreciated in the central cornea.
Figure 1D:
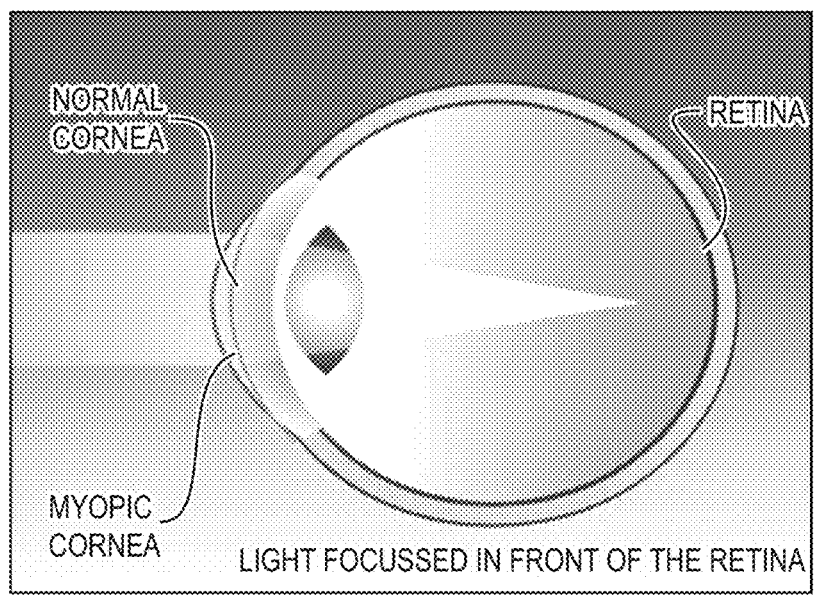
FIG. 1D: Schematic showing myopia caused by an increased curvature of the cornea such that light entering the eye is not focused onto the retina.

Accordingly, the disclosed methods may be utilised in in vivo tissue engineering therapy for various conditions of the cornea, including myopia and keratoconus. As noted above, myopia is characterised by the excessive curvature of the cornea (FIG. 1D), while keratoconus is a progressive ectatic corneal dystrophy leading to a characteristic pattern of corneal thinning (FIG. 1A-1C); images adapted from Romero-Jimenez, Santodomingo-Rubido, & Wolffsohn 2010).

Corneal keratocytes are relatively quiescent and normally only produce large amounts of extracellular matrix (ECM) when they switch to a fibroblast or myofibroblast phenotype. ECM deposition associated with those phenotypes usually leads to corneal fibrosis and loss of transparency (Kadler, Baldock, Bella, & Boot-Handford 2007). Chondrocytes, the cells that make up cartilage, secrete type II collagen which is a fibrillar collagen similar to type I found in the cornea. Type II collagen is also expressed by keratocytes during development of the chick cornea and it is only later replaced by type I in the mature chick stroma (Linsenmayer et al. 1990).

The inventors have previously shown that stromal cells from adult human and rat corneas can be reprogrammed to produce neuron specific proteins when treated with neuronal lineage specifying growth factors (Greene et al. 2013). This data demonstrates that an adult cell population can be reprogrammed simply by the modulation of the growth factor environment both in vitro and in vivo.

Now, as demonstrated herein, the inventors show that corneal stromal cells can be induced in vitro and ex vivo to produce cartilage specific fibrillar collagen, collagen type II, by treating the cells with transforming growth factor β3 (TGFβ3) and dexamethasone (Examples 8 and 9). In particular, the inventors have demonstrated that keratocytes in human keratoconic corneal biopsies express collagen type II when treated with these two compounds (Example 8). In addition, with animal studies, the inventors have demonstrated that the two compounds of TGFβ3 and dexamethasone can be delivered in vivo using eye drops to stimulate collagen II deposition (Example 9). Notably, the deposition of collagen type II was uniform, improving the biomechanics of the cornea, with no fibrosis or scarring, and no effect on corneal transparency (Examples 11 and 13).

Without wishing to be bound by theory, it is hypothesised that the collagen deposition is brought about by the reprogramming of cells within the stroma to a chondrocyte phenotype. It is known that chondrocytes secrete type II collagen which is not only a fibrillar collagen similar to type I found in the cornea, but is also expressed during development of the chick cornea (Linsenmayer et al. 1990). It is only later replaced by collagen type I in the mature stroma (Linsenmayer et al. 1990).

In the results described herein, an initial increase in collagen type I expression was observed upon treatment of corneal keratocytes with TGFβ3 and dexamethasone (Example 12). However, the inventors consider that the observed level of collagen type I deposition would be insufficient to stiffen/reshape a cornea. Furthermore, the deposition of collagen type II is deemed more feasible as a treatment strategy. It is noted that collagen type II is less susceptible to enzymatic degradation, for example, by enzymes present in a keratoconic cornea.

In accordance with the inventors' results, it is possible to use the reprogramming of keratocytes to produce new ECM molecules as an effective treatment to improve the biomechanical characteristics of the cornea. This approach is considered advantageous, as it reduces susceptibility to degradation by corneal enzymes, as noted above. The disclosed treatment module aims not only to stabilise the cornea, but also to provide remedial aid for conditions of the eye, including various corneal conditions and refractive errors of the eye. Thus, the methods of the invention may be used, for example, for the treatment of keratoconic keratocytes in the ectatic cornea. Additionally, the methods of the invention may be used for the treatment of myopia and various other conditions of the cornea, as described in detail herein.

Conditions Affecting the Eye and Cornea

The compositions described herein find particular use in regenerating or augmenting the cornea (e.g., the stromal layer), as well as corneal cells (e.g., keratocytes). The compositions may be used to address corneal thinning, weakening, cell loss, tissue loss, matrix loss, collagen loss, and/or irregularity. In this way, the compositions described herein may be utilised for various conditions affecting the eye, including conditions involving corneal defects, disease, damage, injury, and/or degeneration, as well as refractive errors of the eye.

In specific aspects, the invention encompasses methods for treating defects of the cornea. In certain situations, the methods of the invention may also be used to prevent corneal defects. The defects may be associated with a particular condition of the cornea. Exemplary conditions include keratoconus, as described in detail herein, and related conditions, which include corneal ectasias such as keratoglobus, pellucid marginal degeneration, and posterior keratoconus (see, e.g., Arffa 1997; Krachmer et al. 1984; Rabonitz 2004; Jinabhai et al. 2010). Specifically included as defects are myopia, presbyopia, and also astigmatisms, which encompass regular and irregular astigmatisms. Congenital defects of the cornea are also included. Amongst these are cornea plana and microcornea, the latter of which may be associated with fetal alcohol syndrome, Turner syndrome, Ehlers-Danlos syndrome, Weill-Marchesani syndrome, Waardenburg's syndrome, Nance-Horan syndrome, and Cornelia de Lange's syndrome. Included also is keratoglobus (mentioned above) that may be associated with Ehlers-Danlos syndrome type IV.

In further aspects, the invention encompasses methods for treating damage or degeneration of the cornea. In certain situations, the methods of the invention may be used to prevent corneal damage. Damage or degeneration may be associated with a particular condition of the cornea. Specifically included is corneal melt, for example, corneal melt associated with an inflammatory disorder, such as rheumatoid arthritis. Other exemplary conditions include keratitis, such as marginal keratitis, stromal keratitis, exposure keratitis, neurotrophic keratitis, filamentary keratitis, rosacea keratitis, viral keratitis including herpes keratitis, fungal keratitis, protozoal keratitis, and other infectious keratitis, such as luetic interstitial keratitis, microsporidial keratitis, Thygeson's keratitis, and infectious crystalline keratopathy. Included also is ulcerative keratitis, also called peripheral ulcerative keratitis (PUK), which includes ulcerative keratitis that is associated with a systemic disease, such as rheumatoid arthritis Wegener's granulomatosis, systemic lupus erythematosus, relapsing polychondritis, and polyarteritis nodosa. Endophthalmitis is also included. Included as well are chronic corneal edema, Mooren's ulcer, dellen, phlyctenulosis, Terrien's degeneration, Salzman's degeneration, spheroidal degeneration, and Fuch's dystrophy. Such conditions are well known and well characterised in the art. See, e.g., Jackson 2008; Denniston 2009; and Willshaw et al. 2000. Additionally included are stromal dystrophies, for example, lattice corneal dystrophy (e.g., type 1 and type 2), granular corneal dystrophy (e.g., type 1 and type 2), macular corneal dystrophy, Schnyder corneal dystrophy, congenital stromal corneal dystrophy, and fleck corneal dystrophy.

In still further aspects, the invention encompasses methods for treating injury to the cornea. Included are injuries due to physical damage, chemical damage, radiation damage, and/or damage from particular medication. Injury may be associated with corneal abrasion, corneal erosion, corneal puncture, membrane rupture, corneal scarring, or corneal ulcers, including melting ulcers, indolent ulcers, and superficial ulcers. Included also are injuries and other damage associated with eye surgery, including surgical wounds, corneal damage following radial keratectomy, and acute problems following keratoplasty, which include persistent epithelial defects. Additionally included are injuries associated with corneal melt, for example, corneal melt following surgery or other treatments of the eye (e.g., topical NSAID administration). Corneal melting may be attributable to infectious, inflammatory, or trophic causes. Included also are injuries and damage of the cornea associated with aging.

In even further aspects, the invention encompasses methods for treating or preventing refractive errors of the eye. Such refractive errors may be associated with particular conditions, including myopia, hyperopia, presbyopia, anisometropia, higher order aberrations, and various astigmatisms. Higher order aberrations include, but are not limited to, comas, trefoils, quadrafoils, spherical aberrations, and aberrations identified by mathematical expressions (e.g., Zernike polynomials).

Conditions of the cornea may be diagnosed by various methods, including fluorescein staining, which may include a Seidel's test, specular microscopy, corneal topography, isometric tomography, pachymetry, ultrasound, slit lamps, corneal scrapes, and biopsies. Diagnosis may also involve assessments for visual acuity and/or opacification. Corneal conditions may be associated with one or more symptoms of: pain, photophobia, foreign body sensation, reduced visual acuity, oedema, white cell infiltrate, fluorescein uptake, vascularisation, redness, and systemic symptoms such as headaches, nausea, and fatigue. Similarly, symptoms of refractive errors may include but are not limited to: reduced visual acuity as well as blurry vision, double vision, haziness of vision, visual fatigue, foreign body sensation, problematic glare or halos, starburst patterns, ghost images, impaired night vision, squinting, excessive staring, excessive blinking, headaches, eye rubbing, eye strain, eye surface dessication, eye irritation, redness, and spasms of the eye.

Therapeutic Compositions

As noted above, the compositions described herein may be utilised for treating and/or preventing various conditions of the eye, including conditions affecting the cornea and refractive errors of the eye. The compositions may include a TGFβ3 polypeptide, or variants or fragments thereof, along with dexamethasone, or derivatives thereof or related steroidal agents.

In various aspects, the composition may be formulated to include the noted combination of components (a TGFβ3 polypeptide (or variants or fragments thereof) plus dexamethasone (or derivatives thereof or related steroidal agents)), or may be formulated to include a first component (a TGFβ3 polypeptide (or variants or fragments thereof) or alternatively dexamethasone (or derivatives thereof or related steroidal agents)) with the second component to be added in prior to administration. Alternatively, the composition may be formulated to include a first component (a TGFβ3 polypeptide (or variants or fragments thereof) or alternatively dexamethasone (or derivatives thereof or related steroidal agents)), which is used in simultaneous or sequential administration with a formulation that includes the second component.

In one aspect, the TGFβ3 polypeptide may include at least the following amino acid sequence: ALDTNYCFRN LEENCCVRPL YIDFRQDLGW KWVHEPKGYY ANFCSGPCPY LRSADTTHST VLGLYNTLNP EASASPCCVP QDLEPLTILY YVGRTPKVEQ LSNMVVKSCK CS (SEQ ID NO:1) (GenBank Reference CAR70088.1). The TGFβ3 polypeptide may include at least 112 amino acids shown above, and may have a molecular mass of 25.5 kDa. Alternatively, the TGFβ3 polypeptide may be derived from amino acids 644-850 (207 amino acids) of the precursor polypeptide sequence identified in GenBank Reference CAA33024.1; GenBank Accession No. CAA33024; or NCBI Reference Sequence NP_003230.1.

In other aspects, a TGFβ3 variant or fragment may be utilised. For example, the variant or fragment may exhibit at least 75% sequence identity to SEQ ID NO:1, preferably at least 80% identity, more preferably at least 85%, most preferably at least 90%, at least 91%, at least 92%, at least 93%, at least 94%, at least 95%, at least 96%, at least 97%, at least 98%, at least 99% or about 100% sequence identity to SEQ ID NO:1, as described herein. It is of particular interest where the TGFβ3 variant exhibits biological activity, for example, activity that is similar or improved compared to the non-variant polypeptide In further aspects, a particular fragment may be utilised. For example, the TGFβ3 fragment may comprise at least 80 amino acids, at least 85 amino acids of SEQ ID NO:1, more preferably at least 90 amino acids, at least 91 amino acids, at least 92 amino acids, at least 93 amino acids, at least 94 amino acids, at least 95 amino acids, at least 96 amino acids, at least 97 amino acids, at least 98 amino acids, at least 99 amino acids, most preferably at least 100 amino acids, at least 101 amino acids, at least 102 amino acids, at least 103 amino acids, at least 104 amino acids, at least 105 amino acids, at least 106 amino acids, 107 amino acids, 108 amino acids, 109 amino acids, 110 amino acids, or 111 amino acids of SEQ ID NO:1. Of particular interest are functional fragments of TGFβ3, for example, fragments that exhibit biological activity, for example, activity that is similar or improved compared to the reference polypeptide.

In a particular aspect, the TGFβ3 polypeptide or the variant or fragment thereof may be provided as a recombinant polypeptide. For example, the polypeptide may be expressed in cell or cell-free expression systems as widely known and used in the art. Included amongst these are bacterial, fungal, plant, and mammalian expression systems. Expression systems using *E. coli* cells, CHO cells, HEK cells, and *Nicotiana benthamiana* cells are specifically included. The TGFβ3 polypeptide or the variant or fragment thereof may be provided as a human recombinant polypeptide expressed in human or non-human expression systems. The TGFβ3 polypeptide or the variant or fragment thereof may be provided as a disulfide-linked homodimeric, non-glycosylated, polypeptide chain, in accordance with known methods.

The TGFβ3 polypeptide or the variant or fragment thereof may be isolated from recombinant expression systems by standard methods, including well known chromatographic techniques. The TGFβ3 polypeptide or the variant or fragment thereof may include a sequence tag to facilitate cleavage, isolation, and/or localisation of the polypeptide. In accordance with the present invention, the TGFβ3 polypeptide may be obtained from various commercial sources. For example, recombinant human TGFβ3 may be obtained from R&D Systems (Catalogue Nos. 243-B3-002; 243-B3-010), BioVision, Inc. (Catalogue Nos. 4344-500; 4344-50; 4344-5), or Prospec Protein Specialists (Catalogue Nos. CYT-113; CYT-319).

The biological activity of the TGFβ3 polypeptide or the variant or fragment thereof may be measured in accordance with widely known and used methods. For example, biological activity may be measured in culture by the polypeptides ability to inhibit the mink lung epithelial (Mv1Lu) cells proliferation (see, e.g., Premaraj et al. 2006). Exemplary activity by this measurement is shown by an $ED_{50}$ of ≤50 ng/ml. Alternatively, biological activity may be measured by the dose-dependent inhibition of IL-4 induced proliferation of mouse HT-2 cells (BALB/c spleen activated by sheep erythrocytes in the presence of IL-2) (see, e.g., Tsang et al. 1995). Exemplary activity by this measurement is typically 0.1 to 0.5 ng/ml. Alternatively, the composition that includes the combination of agents described herein may be measured for biological activity using the methods noted below. For example, induction of collagen type II (e.g., collagen type II, alpha 1) in keratocytes can be assessed by one or more of: immunohistochemical assays, protein assays, Western blot analysis, polymerase chain reaction (PCR) analysis, and quantitative PCR technologies.

As described herein, the composition may also include dexamethasone, a derivative thereof, and/or a related steroidal agent. Dexamethasone is characterised as having the following chemical structure:

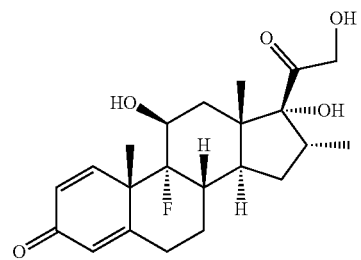

The trade names for dexamethasone include, for example, Decadron®, Dexasone®, Diodex®, Hexadrol®, Maxidex®, and Minims®.

In various aspects, derivatives of dexamethasone may be used, including any esters and salts thereof. Exemplary derivatives include but are not limited to: dexamethasone-17-acetate (CAS RN: 1177-87-3), dexamethasone disodium phosphate (CAS RN: 2392-39-4), dexamethasone valerate (CAS RN: 14899-36-6), dexamethasone-21-isonicotinate (CAS RN: 2265-64-7), dexamethasone palmitate (CAS RN: 33755-46-3), dexamethasone propionate (CAS RN: 55541-30-5), dexamethasone acefurate (CAS RN: 83880-70-0), dexamethasone-21-galactoside (CAS RN: 92901-23-0), dexamethasone 21-thiopivalate, dexamethasone 21-thiopentanoate, dexamethasone 21-thiol-2-methyl-butanoate, dexamethasone 21-thiol-3-methyl-butanoate, dexamethasone 21-thiohexanoate, dexamethasone 21-thiol-4-methyl-pentanoate, dexamethasone 21-thiol-3,3-dimethyl-butanoate, dexamethasone 21-thiol-2-ethyl-butanoate, dexamethasone 21-thiooctanoate, dexamethasone 21-thiol-2-ethyl-hexanoate, dexamethasone 21-thiononanoate, dexamethasone 21-thiodecanoate, dexamethasone 21-p-fluorothiobenzoate or a combination thereof. Specifically included are dexamethasone alcohol and dexamethasone sodium phosphate. Dexamethasone derivatives are also included, as described in U.S. Pat. No. 4,177,268.

The composition may include related steroidal agents, in lieu of or in addition to dexamethasone. For example, other corticoid steroids may be utilised, in replacement of or along with dexamethasone. Preferred for use as related steroids are Group C steroids according to Coopman classification, which includes betamethasone-type steroids, such as dexamethasone, dexamethasone sodium phosphate, betamethasone, betamethasone sodium phosphate, and fluocortolone. Other related steroidal agents include but are not limited to: fluoromethalone, lotoprendol, medrysone, prednisolone, prednisone, rimexolone, hydrocortisone, lodoxamide, or any derivative or combination thereof. Specifically included are fluoromethalone acetate, fluoromethalone alcohol, prednisolone acetate, prednisolone sodium phosphate, lotoprendol etabonate, hydrocortisone acetate, and lodoxamide tromethamine. It is understood, for any of the chemicals of this disclosure, that the chemicals may be in various modified forms such as acetate forms, and sodium phosphate forms, sodium salts, and the like.

The composition may include, for example, 0.04 ng/ml to 4 ng/ml; or 0.04 ng/ml to 0.4 ng/ml; or 0.4 ng/ml to 4 ng/ml; or 4 to 40 ng/ml; or 40 ng/ml to 400 ng/ml, or 40 ng/ml to 4000 ng/ml dexamethasone, or derivative thereof or related steroidal agent; or about 0.04 ng/ml, about 0.08 ng/ml, about 0.12 ng/ml, about 0.4 ng/ml, about 0.8 ng/ml, about 1.2 ng/ml, about 4 ng/ml, about 12 ng/ml, about 24 ng/ml, about 40 ng/ml, about 80 ng/ml, about 120 ng/ml, about 240 ng/ml, about 400 ng/ml, about 800 ng/ml, about 1000 ng/ml, about 1600 ng/ml, about 2000 ng/ml, about 2400 ng/ml, about 3200 ng/ml, or about 4000 ng/ml dexamethasone, or derivative thereof or related steroidal agent.

As further examples, the composition may include 0.4 μg/ml to 40 μg/ml; or 0.4 μg/ml to 4 μg/ml; or 4 μg/ml to 40 μg/ml dexamethasone, or derivative thereof or related steroidal agent; or about 0.4 μg/ml, about 0.8 μg/ml, about 1 μg/ml, about 1.2 μg/ml, about 2 μg/ml, about 4 μg/ml, about 8 μg/ml, about 12 μg/ml, about 20 μg/ml, or about 40 μg/ml dexamethasone, or derivative thereof or related steroidal agent.

As yet further examples, the composition may include 0.1 mg/ml to 1 mg/ml; or 0.5 mg/ml to 5 mg/ml; or 1 mg/ml to 10 mg/ml; dexamethasone, or derivative thereof or related steroidal agent; or about 0.1 mg/ml, about 0.5 mg/ml, about 1 mg/ml, about 2 mg/ml, about 5 mg/ml, or about 10 mg/ml dexamethasone, or derivative thereof or related steroidal agent.

The composition may include, for example, 1 ng/ml to 1 μg/ml; or 1 ng/ml to 10 ng/ml; or 10 ng/ml to 100 ng/ml; or 100 ng/ml to 1 μg/ml TGFβ3 polypeptide or variants or fragments thereof, or about 1 ng/ml, about 5 ng/ml, about 10 ng/ml, about 20 ng/ml, about 50 ng/ml, about 100 ng/ml, about 200 ng/ml, about 500 ng/ml, about 800 ng/ml, or about 1 μg/ml TGFβ3 polypeptide or variants or fragments thereof. In particular aspects, the composition may include at least 40 ng/ml dexamethasone, or derivative thereof or related steroidal agent, along with at least 4 ng/ml TGFβ3 polypeptide, or variants or fragments thereof.

The composition may also include one or more anti-inflammatory agents. Exemplary anti-inflammatory agents include, at least, ketotifen fumarate, diclofenac sodium, flurbiprofen sodium, ketorlac tromethamine, suprofen, celecoxib, naproxen, rofecoxib, or any derivative or combination thereof. Particularly included are non-steroidal anti-inflammatory drugs (NSAIDs). The composition may additionally include one or more anaesthetic agents. Exemplary anaesthetics include, at least, topical anaesthetics such as proparacaine, lidocaine, and tetracaine, and any derivative or combination thereof. Other agents for the eye may be selected for inclusion with the composition; these may be chosen by the skilled artisan based on the condition and needs of the subject under treatment.

The compositions as described herein may be formulated for topical administration, as described herein and in accordance with known methods. In certain circumstances, intraocular administration may be desirable. The composition may be provided in any form suitable for administration to the eye. Exemplary formulations include, at least, solutions, suspensions, emulsions (dispersions), gels, creams, or ointments in a suitable ophthalmic vehicle. For example, the composition may be provided in the form of eye drops, a semisolid gel, or a spray. In certain aspects, moulding contact lenses or other inserts/implants may be impregnated with the composition of the invention. In this manner, the composition can be delivered to the cornea continuously and in a time-release manner as the subject is wearing the contact lenses.

For topical administration to the eye, the compositions may be formulated with a pH range of 5.0 to 8.0. This pH range may be achieved by the addition of buffers to the solution. It is preferred that the formulations are stable in buffered solutions. That is, there is no adverse interaction between the buffer and the active agents that would cause the composition to be unstable, e.g., by precipitation or aggregation. The composition may be hypertonic (5% to 40%, preferably approximately 10, 20, 30, or 40%) or hypotonic (0% to 5%, preferably approximately 1, 2, 3, or 4%) depending on the needs of the subject (e.g., working needs, rest hours, sleeping, etc.) A hypertonic composition (e.g., 40%) may be used when combined with moulding contact lenses, as described in detail herein.

The compositions may include one or more suitable preservatives as optional ingredients. Suitable preservatives may be added to prevent contamination, for example, bacterial contamination. Such agents may include, but are not limited to, benzalkonium chloride, thimerosal, chlorobutanol, methyl paraben, propyl paraben, phenylethyl alcohol, EDTA, sorbic acid, Onamer® M, and other agents known to those skilled in the art, or any combination thereof. Such preservatives may be typically employed at a level of 0.001% to 1.0% by weight of the composition.

The compositions may contain an optional co-solvent. The solubility of the components of the present compositions may be enhanced by a surfactant or other appropriate co-solvent in the composition. Such co-solvents/surfactants include, for example, polysorbate 20, 60, and 80, polyoxyethylene/polyoxypropylene surfactants (e.g. Pluronic® F-68, F-84, and P-103), cyclodextrin, tyloxapol, and other agents known to those skilled in the art, and any combination thereof. Such co-solvents may be typically employed at a level of 0.01% to 2% by weight of the composition.

Penetration enhancing agents may be used to increase uptake of the composition into the eye. Exemplary agents include, at least, cetylpyridinium chloride, ionophores such as lasalocid, benzalkonium chloride, Parabens, Tween 20, saponins, Brij Brij 78, Brij 98, ethylenediaminetetraacetic acid, bile salts, and bile acids (such as sodium cholate, sodium taurocholate, sodium glycodeoxycholate, sodium taurodeoxycholate, taurocholic acid, chenodeoxycholic acid, and ursodeoxycholic acid), capric acid, azone, fusidic acid, hexamethylene lauramide, saponins, hexamethylene octanamide, and decylmethyl sulfoxide.

In addition, bioadhesive polymers may be used to adhere to the mucin coat covering the eye, to prolong contact of the composition with the eye. Bioadhesive polymers may be macromolecular hydrocolloids with numerous hydrophilic functional groups, such as carboxyl-, hydroxyl-, amide, and sulphate capable of establishing electrostatic interactions. Exemplary agents include, at least, polyarylic acid (e.g., carbopol, carbophil, and polycarbophil) and carboxymethyl cellulose.

Controlled release systems may also be used; such systems may involve in situ gels, colloidal particles, nanoparticles, and/or niosomes. Other drug delivery systems include but are not limited to: non-erodible ocular inserts, erodible ocular inserts, hydrogels, collagen shields, liposomes, drug-loaded films (e.g., NOD®), and ionotophoresis.

The compositions may include, also, an optional agent to increase viscosity. Viscosity increased above that of simple aqueous solutions may be desirable to increase ocular absorption of the active compounds, to decrease variability in dispensing the formulation, to decrease physical separation of components of a suspension or emulsion of the formulation and/or to otherwise improve the ophthalmic formulation. Such viscosity builder agents include as examples polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or a combination thereof. Such agents may be typically employed at a level of to 2% by weight of the composition.

In particular aspects, the compositions include a gelling agent, for example, high molecular weight water-soluble polysaccharides such as gellan gum. Gellan gum may be obtained from various commercial sources, for example, as sold under the trade name Kelcogel®. In particular, Kelcogel® LT100 may be used as a fine mesh, high acyl gellan, which forms soft, elastic, non-brittle gels. In specific aspects, the gellan gum based composition is formulated as a 0.5% eye drop Other agents may be used to further stabilise or otherwise enhance the composition. For example, one or more of EDTA, sodium chloride, tyloxapol, sodium sulfate, and/or hydroxyethylcellulose may have additional beneficial effects of further stabilising the composition.

Therapeutic Methods

As noted above, the compositions described herein find particular use in regenerating or augmenting the cornea (e.g., the stromal layer), as well as corneal cells (e.g., keratocytes). In particular, the compositions may be used to provide enhanced shaping, thickness, regularity, hardness, elastic modulus, tensile strength, or functionality (e.g., refraction) of the cornea. Thus, the compositions described herein may be used to address various conditions of the cornea and correct refractive errors of the eye, and may be used as adjunct therapy with other eye treatments.

As previously noted, the composition may be formulated in any suitable means for administration to the eye. Included as formulations are ophthalmic solutions, creams, emulsions, ointments, and gels. Specifically noted are formulations that are made as eye drops. In a particular aspect, the composition may be administered as an eye drop using any of the many types of eye drop dispensers on the market. As exemplifications, the container for the compositions of the invention may be clear, translucent, and opaque and may contain other properties or combination of properties such as being glass lined, tamper proof, packaged in single or few dose aliquots, and any combination thereof.

The composition may be administered in therapeutically effective amounts to a subject to achieve a desired medical outcome. In particular, the composition may be administered in amounts to address an ophthalmic condition described herein, or at least mitigate one or more symptoms of such condition. The precise dosage of the composition (i.e., amount and scheduling) may be determined by a clinician, based on the subject and the condition presented. Exemplary formulations (e.g., eye drops) may be administered 1 to 24 times per day, or 1 to 12 times per day, or 1 to 6 times per day, or 1 to 4 times per day, or 1 to 3 times per day, or 1 to 2 times per day, or 1, 2, 3 4, 6, 8, 12, 18, or 24 times per day. The composition may be topically applied as an eye drop by placing one drop in each eye to be treated. Alternatively, 2 to 3 drops may be applied to each eye.

For the described composition, the dosage range may be, for example, 0.2 pg to 2.4 ng; or 2 pg to 2.4 ng of dexamethasone, or derivative thereof or related steroidal agent; or about 0.2 pg, about 0.4 pg, about 0.6 pg, about 0.8 pg, about 1.2 pg, about 2.4 pg, about 2 pg, about 4 pg, about 6 pg, about 8 pg, about 12 pg, about 18 pg, about 24 pg, about 0.2 ng, about 0.26 ng, about 0.4 ng, about 0.6 ng, about 0.8 ng, about 1.2 ng, about 1.8 ng, or about 2.4 ng of dexamethasone, or derivative thereof or related steroidal agent, per eye for one dose.

As other examples, the dosage range may be 12 ng to 1.3 µg; or 6 ng to 600 ng dexamethasone, or derivative thereof or related steroidal agent; or about 6 ng, about 8 ng, about 12 ng, about 16 ng, about 18 ng, about 24 ng, about 26 ng, about 30 ng, about 36 ng, about 40 ng, about 48 ng, about 52 ng, about 54 ng, about 60 ng, about 72 ng, about 78 ng, about 80 ng, about 90 ng, about 120 ng, about 130 ng, about 160 ng, about 180 ng, about 240 ng, about 260 ng, about 300 ng, about 360 ng, about 400 ng, about 480 ng, about 520 ng, about 540 ng, about 600 ng, about 720 ng, about 780 ng, about 900 ng, about 1.2 µg, about 1.3 µg of dexamethasone, or derivative thereof or related steroidal agent, per eye for one dose.

As still other examples, the dosage range may be 1.5 µg to 150 µg; 2.6 µg to 260 µg; or 6.5 µg to 650 µg of dexamethasone, or derivative thereof or related steroidal agent; or about 1.5 µg, about 2 µg, about 3 µg, about 4.5 µg, about 6 µg, about 6.5 µg, about 7.5 µg, about 10 µg, about 15 µg, about 22.5 µg, about 32.5 µg, about 20 µg, about 26 µg, about 30 µg, about 40 µg, about 45 µg, about 60 µg, about 65 µg, about 75 µg, about 80 µg, about 90 µg, about 100 µg, about 120 µg, about 130 µg, about 150 µg, about 180 µg, about 225 µg, about 240 µg, about 260 µg, about 200 µg, about 300 µg, about 325 µg, about 450 µg, about 600 µg, or about 650 µg dexamethasone, or derivative thereof or related steroidal agent, per eye for one dose. It will be recognised that specific formulations of dexamethasone are commercially available, and such may be utilised in accordance with accepted dosage amounts and scheduling.

Any of the above noted dosages of dexamethasone may be co-administered with a dosage range of, for example, 5 pg to 65 ng; or 0.5 ng to 65 ng of TGFβ3 polypeptide, or variants or fragments thereof; or about 5 pg, about 10 pg, about 15 pg, about 20 pg, about 30 pg, about 45 pg, about 60 pg, about 0.05 ng, about 0.1 ng, about 0.15 ng, about 0.2 ng, about 0.3 ng, about 0.45 ng, about 0.5 ng, about 0.6 ng, about 0.65 ng, about 1 ng, about 1.5 ng, about 2 ng, about 3 ng, about 4 ng, about 4.5 ng, about 6 ng, about 6.5 ng, about 7.5 ng, about 9 ng, about 10 ng, about 12 ng, about 13 ng, about 15 ng, about 16 ng, about 20 ng, about 22.5 ng, about 24 ng, about 30 ng, about 32.5 ng, about 36 ng, about 40 ng, about 45 ng, about 48 ng, about 50 ng, about 52 ng, about 60 ng, or about 65 ng of TGFβ3 polypeptide, or variants or fragments thereof, per eye for one dose.

Dosage for one eye may be about one drop of the disclosed composition. One drop of composition may be 10

μl to 200 μl, 20 μl and 120 μl, or 50 μl to 80 μl or any values in between. For example, dispensers such as pipettors can dispense drops from 1 μl to 300 μl and any value in between. Preferably, the dispenser metes out about 15 μl, about 20 μl, about 30 μl, about 45 μl, about 60 μl, or about 65 μl per drop of the disclosed composition.

Where the composition is administered via a contact lens or another insert/implant device, the contact lens or insert/implant may include, for example, 0.01 mg to 10 mg of dexamethasone, or derivative thereof or related steroidal agent; or about 0.01 mg, about 0.1 mg, about 0.5 mg, about 0.7 mg, about 1 mg, about 5 mg, or about 10 mg of dexamethasone, or derivative thereof or related steroidal agent. Alternatively, the contact lens or insert/implant may include 10 ng to 100 ng of dexamethasone, or derivative thereof or related steroidal agent; or about 1 ng, about 5 ng, about 10 ng, about 20 ng, about 50 ng, about 80 ng, or about 100 ng dexamethasone, or derivative thereof or related steroidal agent. As further examples, the contact lens or insert/implant may include about 10 ng to 1 μg of TGFβ3 polypeptide, or variants or fragments thereof; or about 10 ng, about 50 ng, about 100 ng, about 200 ng, about 500 ng, about 800 ng, or about 1 μg TGFβ3 polypeptide, or variants or fragments thereof.

The compositions described herein may be used in conjunction with various surgical procedures or other treatments. For example, the compositions can be used along with surgical and non-surgical methods for the refractive correction of the eye. Exemplary methods include but are not limited to: radial keratotomy (RK), including mini asymmetric radial keratotomy (MARK), hexagonal keratotomy (HK), photorefractive keratectomy (PRK), keratomilleusis, laser in situ keratomileusis (LASIK), e.g., intraLASIK®, laser epithelial keratomileusis (LASEK), e.g., Epi-LASEK, automated lamellar keratoplasty (ALK), laser thermal keratoplasty (LTK), conductive keratoplasty (CK), limbal relaxing incisions (LRI), astigmatic keratotomy (AK), epikeratophakia, anterior ciliary sclerotomy (ACS), scleral reinforcement surgery, presbyopia reversal, laser reversal of presbyopia (LRP), intracorneal rings (ICR), intrastromal corneal ring segments (e.g., INTACTS®), implantable contact lenses, scleral expansion bands (SEB), and Kamra™ inlays. Also included are thermokeratoplasty, orthokeratology, enzyme orthokeratology, and chemical orthokeratology.

The compositions may be used in conjunction with surgical correction of non-refractive conditions, for example, surgical correction of a corneal tear. In particular aspects, the compositions described herein may be used in conjunction with specific surgical methods performed on the cornea. Exemplary methods include but are not limited to: corneal transplant surgery, penetrating keratoplasty (PK), phototherapeutic keratectomy (PTK), pterygium excision, corneal tattooing, keratoprosthesis insertion (e.g., KPro or Dohlman-Doane), and osteo-odonto-keratoprosthesis insertion (OOKP).

The compositions may be used in conjunction with corneal collagen crosslinking. Corneal crosslinking typically involves the use of riboflavin solution activated by exposure to UV-A light. Noted crosslinking methods include but are not limited to: corneal crosslinking with the epithelium removed (Dresden protocol, or epi-off), transepithelial crosslinking (epi-on), and accelerated crosslinking. Crosslinking procedures are generally available, and marketed as CXL, C3-R® CCL® and KXL® corneal crosslinking, amongst others. Administration of the composition may be prior to, and/or subsequent to, the crosslinking procedure. It is proposed that the disclosed compositions can be used to avoid or counter the deleterious effects of crosslinking procedures, such as stromal haze and cell loss (described in more detail, below). Moreover, corneal regeneration with the disclosed compositions can allow crosslinking to be performed on subjects who were previously ineligible for such procedures, e.g., those with corneal thickness less than 400 μm. Furthermore, the disclosed compositions can be used to slow or halt progressive corneal thinning, which would not be addressed by the use of crosslinking on its own.

The compositions described herein may be co-administered with one or more additional agents for the eye. In various aspects, co-administration may be by simultaneous or subsequent administration with such agents, or by co-formulation with such agents. Depending on the condition being treated or prevented, the compositions described herein may be co-administered with one or more agents, which include but are not limited to: antihistamines, sympathomimetics, beta receptor blockers, parasympathomimetics, parasympatholytics, prostaglandins, nutrients, vasoconstrictors, lubricants, anti-microbials, and anaesthetics. Specifically included are various anti-inflammatory agents, including non-steroidal anti-inflammatory drugs (NSAIDs). The compositions may also be co-administered with eye lubricating solutions and tear-replacing solutions.

Non-limiting examples of anaesthetics include: benzocaine, bupivacaine, cocaine, etidocaine, lidocaine, mepivacaine, pramoxine, prilocalne, chloroprocaine, procaine, proparacaine, ropicaine, and tetracaine. Non-limiting examples of anti-inflammatory agents include: aspirin, acetaminophen, indomethacin, sulfasalazine, olsalazine, sodium salicylate, choline magnesium trisalicylate, salsalate, diflunisal, salicylsalicylic acid, sulindac, etodolac, tolmetin, diclofenac, ketorolac, ibuprofen, naproxen, flurbiprofen, ketoprofen, fenoprofen, suprofen, oxaproxin, mefenamic acid, meclofenamic acid, oxicams, piroxicam, tenoxicam, pyrazolidinediones, phenylbutazone, oxyphenthatrazone, pheniramine, antazoline, nabumetone, COX-2 inhibitors (Celebrex®), apazone, nimesulide, and zileuton. Glucocorticoids such as hydrocortisone, prednisolone, fluorometholone, and dexamethasone may also be used as anti-inflammatory agents.

Exemplary anti-microbial agents include but are not limited to: bacitracin zinc, chloramphenicol, chlorotetracycline, ciprofloxacin, erythromycin, gentamicin, norfloxacin, sulfacetamide, sulfisoxazole, polymyxin B, tetracycline, tobramycin, idoxuridine, trifluridine, vidarabine, acyclovir, foscarnet, ganciclovir, natamycin, amphotericin B, clotrimazole, econazole, fluconazole, ketoconazole, miconazole, flucytosine, clindamycin, pyrimethamine, folinic acid, sulfadiazine, and trimethoprim-sulfamethoxazole. Exemplary vasoconstrictors include but are not limited to: dipivefrin (Propine®), epinephrine, phenylephrine, apraclonidine, cocaine, hydroxyamphetamine, naphazoline, tetrahydrozoline, dapiprazole, betaxolol, carteolol, levobunolol, metipranolol, and timolol. Nutrients include vitamins, minerals, and other beneficial agents such as vitamin A, vitamin $B_1$, vitamin $B_6$, vitamin $B_{12}$, vitamin C (ascorbic acid), vitamin E, vitamin K, and zinc.

In specific aspects, the composition described herein is formulated as eye drops, and such eye drops are used in conjunction with other eye drop formulations. Such other eye drops may include but are not limited to: rinse/lubricating eye drops, dry eye treatments, steroid and antibiotic eye drops, glaucoma eye drops, allergy/anti-inflammatory eye drops, and conjunctivitis eye drops.

The compositions may be used in conjunction with contact lenses, corneal inserts, corneal implants, or intrastromal rings, to assist in supporting or reshaping the subject's cornea. Included amongst corneal inserts are corneal inlay and corneal onlay devices. For example, contact lenses, intrastromal rings, or other inserts/implants may be used for moulding or holding corneal shape preceding, during, and/or following treatment with the composition. It is noted that a corneal 'insert' typically refers to a temporary device inserted into the cornea, while a corneal 'implant' typically refers to a more permanent device. However, many well known devices are described interchangeably in the art as implants/inserts. Therefore, the terms 'insert/implant' as used herein are not to be deemed as strictly limiting based on time of usage.

The contact lens, corneal insert, corneal implant, or intrastromal ring may be used with the disclosed composition for treatment of corneal defects, diseases, damage, injury, and/or degeneration, as well as refractive errors of the eye. In various aspects, the contact lens, corneal insert, corneal implant, or intrastromal ring may act as a carrier for the composition or as a composition eluting device. In other aspects, the contact lens, intrastromal ring, or other corneal insert/implant may be utilised with the composition that is suitable for administration to the eye, e.g., eye drops, as described in detail herein. In certain aspects, computer software may be used to determine the contact lenses, corneal inserts, corneal implants, or intrastromal rings that are most suitable for the subject and/or to determine the formulation of the composition. In particular aspects, treatment utilising contact lenses, corneal inserts, corneal implants, or intrastromal rings along with the composition described herein is used preceding or following eye surgery, e.g., refractive or transplant surgery.

The treatment may involve assessing the subject (e.g., age, working needs of the subject, eye defect or disease, etc.), prescribing the use of moulding contact lenses, corneal inserts, corneal implants, or intrastromal rings to assist with the needed changes in the radius of curvature of the anterior surface of the cornea, and prescribing the composition described herein to be used in conjunction with the contact lenses or implants/inserts. The contact lenses or implants/inserts which are prescribed and utilised by the subject can be used exert a mechanical force on the cornea thereby inducing a change in shape, i.e., the refractive power, of the cornea.

In certain preferred aspects, the cornea may be supported or shaped by use of a corneal insert, corneal implant, or intrastromal ring in conjunction with the disclosed composition. Examples of commercially available devices include INTACS® and KeraRing intrastromal corneal rings. In another aspect, a moulding contact lens may be used in conjunction with the disclosed composition. The contact lens may be hard or rigid, or it may be a soft lens. Alternatively, the contact lens may comprise both hard and soft portions. If a soft contact lens is used, more positive or negative curvature can be induce in the cornea, and the discomfort in the subject's eyes will diminish as he or she adapts to the contact lenses. If a hard contact lens is used, more mechanical pressure can be exerted on the cornea. The contact lenses may be gas permeable. Moulding contact lenses may be obtained from commercial sources. Examples of commercially available lenses include, at least, DreamLite, OK Lens, EyeDream, MiracLens, DreamLens, i-GO OVC, GOV, Wake and See, CRT, Fargo/iSee, Emerald and Wave Contact Lens System lenses.

Once the contact lens, corneal insert, corneal implant, or intrastromal ring is placed on/into the eye of the subject, the composition described herein (e.g., eye drops) may be administered to the eye. In certain circumstances, it may be desirable to pre-administer the composition prior to placement of the contact lens, corneal insert, corneal implant, or intrastromal ring. Advantageously, the contact lenses, intrastromal rings, or other inserts/implants and the composition may be used in conjunction to produce a change in the shape, and thereby the refractive power, of the cornea. The composition may be administered more frequently to allow the cornea to adopt the desired change in shape. In certain aspects, the composition is administered at least every 24, 12, or 8 hours. In other aspects, the composition is administered every 6 hours. In certain other aspects, the composition is administered approximately every 3 hours. In yet other aspects, the composition is administered approximately every 2 hours. In still other aspects, the composition is administered every hour.

Without wishing to be bound by any particular theory, the combined use of contact lenses, corneal inserts, corneal implants, or intrastromal rings and the composition described herein may induce changes in the molecular structure of the cornea and may induce changes in the cells and proteins such as collagen (e.g., collagen type II) found in the corneal stroma. The surface of the cornea is thereby made more uniform. By reducing irregularities in the surface of the cornea, the quality and clearness of all images (i.e., visual acuity) is improved.

For the calculation of the moulding contact lenses the flattest keratometry is taken. One of skill in this art could also use the steeper keratometry or an average of both and based on this corneal curvature make the necessary calculations to flatten or steepen the radius of curvature of the anterior surface of the cornea and thus correct the refractive defect of the eye. The base curve of the moulding contact lens may be calculated based on the change in the refractive power for each eye separately. In particular aspects, the base curve of the moulding contact lens may be calculated starting with one to four flatter or steeper diopters, more preferably one to three flatter or steeper diopters, even more preferably one to two flatter or steeper diopters, depending on the refractive error that is required. The peripheral base curve depends on the adaptation of the moulding contact lens and is calculated to be 0.5 mm of radius greater than the central zone, but can vary depending on the design.

The diameter of the moulding contact lens used in accordance with the invention may be from 8.0 mm to 18.0 mm. Commercially available lenses are produced with such diameters. In certain aspects, the moulding contact lens may be a hard contact lens with a diameter ranging from 8.0 mm to 12.0 mm. In other aspects, the moulding contact lens may be a soft contact lens with a diameter ranging from 13.0 mm to 15.0 mm. Soft contact lenses may cover the entire cornea and go from sclera to sclera. In still other aspects, the moulding contact lens may be comprised of hard and soft materials. The contact lens may be hard in the centre, out to approximately 12.0 mm, 13.0 mm, 14.0 mm, or 15.0 mm, and then soft in the periphery out to 16.0 mm, 17.0 mm, and 18.0 mm. A larger contact lens, preferably a soft contact lens, may be used at night as a moulding contact lens.

The power of the moulding contact lenses can be determined to the nearest possible refractive power that the subject requires to see comfortably. During the adaptation process with the moulding contact lenses, if the vision is not adequate for the needs of the subject, the subject is prescribed eyeglasses while the subject is undergoing treatment. As the cornea is being reshaped or has been reshaped, various optometric measurements may be repeated to confirm that the treatment is progressing as planned and is adequate. Such measurements may include assessment of visual acuity for near and far vision, orthotypes, keratometry measurements, objective and subjective retinoscopy, diagrams of the adaptation of the moulding contact lens, movement of the moulding contact lens, and comfort of the moulding contact lens.

After the measurements are taken, changes may be made to the treatment program based on these measurements. With each evaluation, a decision may be made whether to continue with the same moulding contact lens or whether a new contact lens should be used. In addition, the same decision can be made with regard to the composition being used with the moulding contact lenses. Changes in the moulding contact lenses and/or in the composition can be made to induce the desired reshaping of the cornea over several weeks. In certain aspects, weekly periodic revisions are performed during the first 8 weeks after beginning treatment.

The composition as described herein induces changes in the collagen content of the cornea (e.g., collagen type II). Other aspects of the anatomy, histology, and physiology of the cornea may also be affected by composition. In certain aspects, the composition may be hypertonic or hypotonic to induce changes in corneal hydration. In other aspects, the composition may be used to change the molecular structure of the cornea (e.g., the extracellular matrix) and in this way augment or repair the cornea, or reshape the cornea to the desired curvature.

When reshaping the cornea, it may be desirable to co-administer one or more enzymes to soften the cornea. Exemplary enzymes include but are not limited to hyaluronidase, chondroitinase ABC, chondroitinase AC, keratanse, and stromelysin, which have been shown to work on various proteoglycan components of the cornea. Included also are the enzyme collagenase, matrix metalloproteinase 1 (interstitial collagenase), and matrix metalloproteinase 2 (gelatinase). Where the composition is co-administered with any such enzymes, it may be desirable to include a vehicle such as a polymer (e.g., methylcellulose, polyvinyl alcohol, cellulose, etc.) in the composition to enhance the working of such enzymes. Additional agents may be included to activate metalloproteinase enzymes, e.g., interleukin-1a, tumour necrosis factor $\alpha/\beta$ and any subtypes thereof, monosodium urate monohydrate, 4-amino phenylmercuric acetate, human serum amyloid A, human $B_2$ microglobin, and copper chloride. Also included may be carbamide (urea). Any combination of these agents may also be used.

The composition may also be co-administered with one or more enzymes that degrade other sugars or proteins found in the cornea. The composition may be co-administered with one or more anaesthetics used to reduce the irritation of the moulding contact lens or any corneal insert/implant to the cornea. The composition may be co-administered with one or more lubricants to improve the comfort of the subject during the treatment. In other aspects, the composition may be co-administered with one or more anti-microbial agents such as anti-bacterial, anti-viral, and/or anti-fungal agents. The composition may also be co-administered with one or more vasoconstrictors. The person of skill in the art can determine the appropriate agents for co-administration to the subject based on the condition being treated.

In certain aspects, the composition may be provided in a kit. The kit may include one or more of: moulding contact lenses, lubricating eye drops, cleaning or other solutions for the contact lenses, a contact lens carrying case, an extra pair of contact lenses, and instructions for wearing the contact lenses and using the composition. The composition provided with the kit may be formulated to include the noted combination of components (a TGFβ3 polypeptide (or variants or fragments thereof) plus dexamethasone (or derivatives thereof or related steroidal agents)), or the kit may include the components as separate formulations, to be mixed together prior to administration, or to be administered together, i.e., by simultaneous or sequential administration.

EXAMPLES

The examples described herein are provided for the purpose of illustrating specific embodiments and aspects of the invention and are not intended to limit the invention in any way. Persons of ordinary skill can utilise the disclosures and teachings herein to produce other embodiments, aspects, and variations without undue experimentation. All such embodiments, aspects, and variations are considered to be part of this invention.

Example 1: Overview of Experiments

In previous experiments, the inventors have shown that it is possible to direct keratocytes to differentiate down a neuronal lineage. The experiments described herein have aimed to investigate the potential of keratocytes to switch to a chondrocyte-like cells that secrete cartilage specific collagen type II. This type of cartilage is thought to be expressed during development (Linsenmayer et al. 1990). A further aim has been to establish whether collagen type II deposition could be induced in vivo in the corneas of live rats and whether this treatment positively affected the optical properties of the corneas. A still further aim has been to determine whether keratocytes in keratoconic tissue could be amenable to this method of cell reprogramming and subsequent production of collagen type II rich ECM. Finally, the experiments have aimed to evaluate the effect of type II collagen deposition on the biomechanical properties of the in vivo and ex vivo treated corneas using nanoindentation testing, a bioengineering approach that enables analysis of hardness and elastic modulus.

Example 2: Tissue Samples

Human Tissue
Cadaveric whole human corneas, keratoconic corneas obtained at the time of transplant surgery, human limbal rims and surgeon cut DSEK caps (excess stromal tissue from Descemet's stripping endothelial keratoplasty) were obtained from donors sourced through the New Zealand National Eye Bank (Auckland, New Zealand). Human limbal rims were collected after the central corneal button had been removed for corneal transplantation surgery leaving a 2 mm corneal margin from the limbal junction. Prior to the use of tissue, research ethics approval and consent was obtained from the Northern X Regional Human Ethics Committee. All tissue, until use, was stored in New Zealand Eye Bank medium (2% FCS, 2 mM L-glutamine, 1×Anti-Anti in Eagles MEM) and transported in New Zealand Eye Bank transport medium (Eye Bank medium supplemented with 5% dextran).
Animal Tissue
Ethics approval for animal studies was obtained from the University of Auckland Animal Ethics Committee (application number R856). Eyes and cartilage from 6-8 week old adult male Wistar rats were obtained after euthanisation using a carbon dioxide chamber. The whole eye was removed from the animal and the cornea was carefully dissected out using surgical scissors with the aid of a dissecting microscope. The xiphoid process, which is part of the sternum that contains a thin, broad plate of cartilage at its end, was dissected out using a scalpel blade. The animal tissue was washed with povidone-iodine (PVP-I) and sodium thiosulphate. The excess fat and tissue covering the cartilage was scraped away with a blade. Freshly harvested eyes and cartilage were stored for a minimal amount of time in phosphate buffered saline solution until use.

Example 3: Histological Analysis

Tissue Preparation and Cryosectioning

Corneal and cartilage pieces (2 mm×2 mm) were embedded in Optimal Cutting Temperature compound (OCT, Tissue-Tek, Sakura, The Netherlands) before being snap frozen in liquid nitrogen. Sections 10-15 µm thick were cut using a Microm HM550 Cryostat (Thermo-Scientific, USA) and mounted on SuperFrost™ Plus electrostatic slides (Menzel-Glenser, Germany). Cryosections were stored at −20° C. until further use.

Cell and Tissue Culture

Tissue Digestion and Cell Preparation from Human and Rat Corneas

Limbal rims were dissected to isolate stroma from sclera in a class II laminar flow hood. Following this, the corneal epithelium and endothelium was gently scraped off with a keratome and discarded. DSEK caps also received gentle scraping with a keratome to remove the epithelium. Remaining stromal tissue was then digested in 0.4% type II collagenase (Sigma-Aldrich), in Hanks balanced salt solution (GIBCO®, Life Technologies) at 37° C. with gentle mixing on an orbital shaker. A variety of digestion times were used with 5 hours being the time required for optimal tissue digestion and cell viability.

After tissue digestion was complete the cells were pelleted by centrifuging at 1200 rpm for seven minutes. The cells were then resuspended in a minimal amount of an appropriate cell culture medium and counted using a Leica DM IL bench top inverted microscope and a Neubauer hemocytometer. A 1:1 ratio of cell suspension added to trypan blue solution (0.04% trypan blue stock in PBS) was used with a minimum of three counts per sample and the average value taken.

Cell Culture of Corneal Keratocytes

All cell manipulations were performed in a class II laminar flow hood using aseptic technique. Isolated keratocytes were cultured in either 12 or 24 well cluster plates (Falcon) on plastic or glass coverslips in 2-3 ml of cell culture media. Cells were kept in a humidified incubator at 37° C. with 5% $CO_2$. Culture media was changed after 24 hours then every two days subsequently or more frequently if required. Cultures were viewed daily with a Leica DM IL bench top inverted microscope. For cell pellet culture, freshly obtained cells after tissue were pelleted by centrifuging at 300 g for 7 minutes at 20° C. in a plastic conical tube. Appropriate culture media was added to the tubes. After 24 hours of incubation at 37° C., the cells had contracted and formed a pellet which did not adhere to the walls of the tube. The pellets were cultured in 2 ml of media in a humidified atmosphere of 5% $CO_2$ at 37° C. for three weeks. Media was changed every other day.

Organotypic Slice Culture

Figure 2:
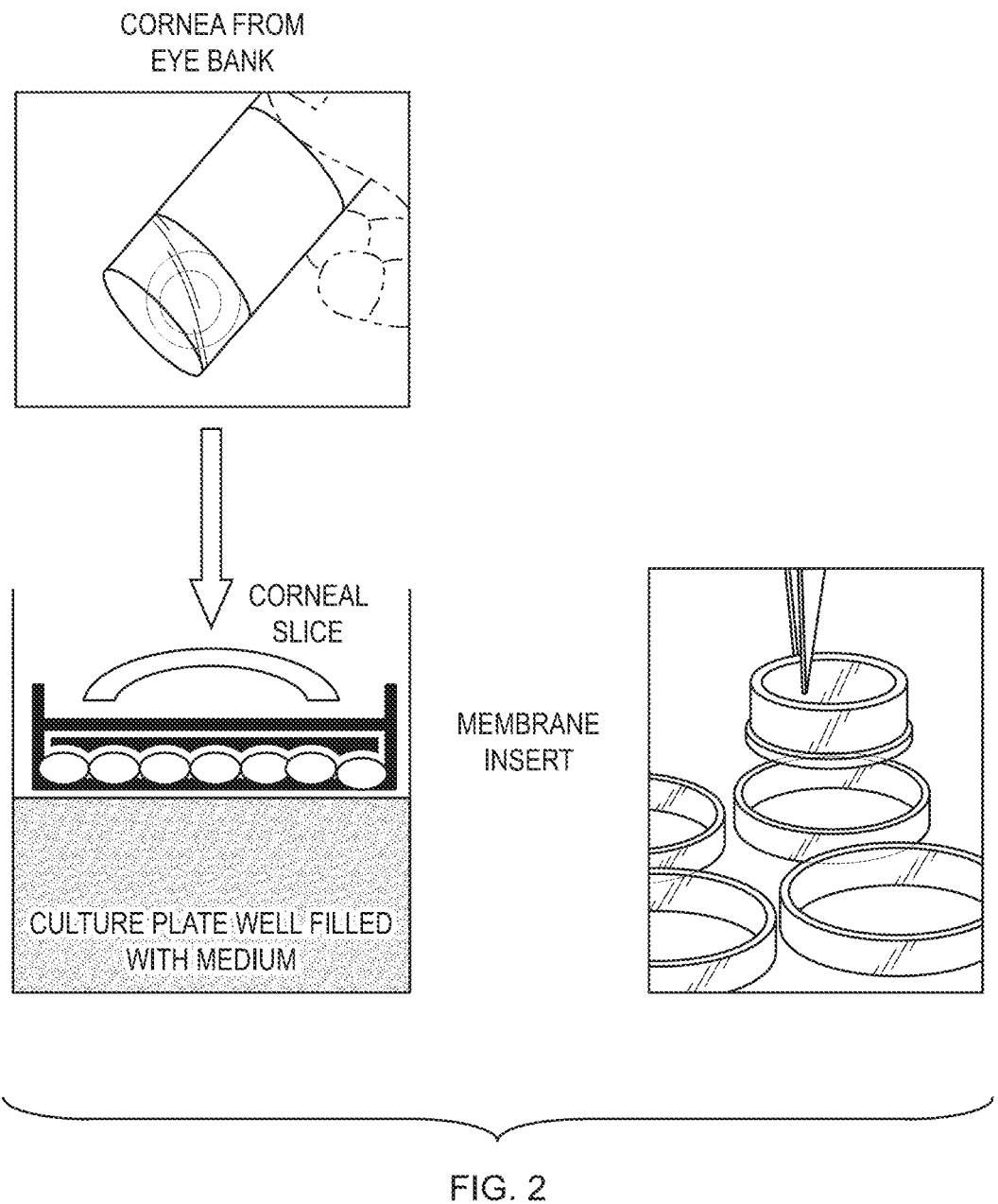
FIG. 2: Organotypic slice culture set up.

Human and rat corneal and cartilage tissue was thin-sliced (1-2 mm) in an anteroposterior plane with a blade and the slices were placed in an organotypic air-liquid interphase culture system (FIG. 2). Briefly, the explants of healthy tissue were cultured on 0.4 µm pore size cell culture inserts (Millicell, France) at the interface between culture medium and a $CO_2$ rich environment. Corneal sections were placed epithelium side up on cell culture plate inserts with 3 ml of culture medium. The culture media was changed every other day.

Example 3: In Vitro Reprogramming

Culture Media

Several custom made media were used as described in the table below.

TABLE 1

Cell culture media used

| Name | Medium Base | Other Components |
| --- | --- | --- |
| Fibroblast proliferation medium | Dulbecco's Modified Eagle Medium (DMEM) (Life Technologies, GIBCO ®) | 10% FBS, 1% Anti-anti (100X stock), 1% GlutaMAX ™ (100X stock) |
| Chondrogenic reprogramming medium | Advanced DMEM (Life Technologies, GIBCO ®) | 10 ng/ml TGFβ3 (Abcam, ab52313), $10^{-7}$ M dexamethasone (Abcam, ab120743), 1% GlutaMAX ™ (Life Technologies, GIBCO ®) (100X stock), 1% Anti-Anti (100X stock) (Life Technologies, GIBCO ®) |
| Control medium | Dulbecco's Modified Eagle Medium (DMEM) | 1% GlutaMAX ™ (100X stock), 1% Anti-Anti (100X stock) |

Chondrogenic Reprogramming of Keratocytes

Tissue slices were cultured in the chondrogenic differentiation medium for varying time intervals to determine the optimum time required for the growth factor treatment. Samples were collected for each time point (Table 2). For obtaining a monolayer of cells, keratocytes were seeded on glass coverslips at a density of 15×10 4 per cm 2. The cells were allowed to attach to the coverslips for 24 hours and culture media was changed every other day. Cultures were maintained for up to 3 weeks.

TABLE 2

Experimental time points for corneal tissue slice culture

|  | Time point 1 Week 1 | Time point 1 Week 2 | Time point 1 Week 3 |
|---|---|---|---|
| Sample 1 | chondrogenic differentiation medium | control medium | control medium |
| Sample 2 | chondrogenic differentiation medium | chondrogenic differentiation medium | control medium |
| Sample 3 | chondrogenic differentiation medium | chondrogenic differentiation medium | chondrogenic differentiation medium |
| Sample 4 | control medium | control medium | control medium |

Example 4: In Vivo Reprogramming

Gel Eye Drop Formulation for Growth Factor Delivery

Eye drops were formulated using gellan gum which is a water soluble polysaccharide produced by the bacterium, *Pseudomonas elodea*. The use of gel base formulation allows a prolonged corneal residence time and increased ocular bioavailability of the therapeutic agent. Since polymeric gellan gum is an anionic polymer it undergoes in situ gelling in the presence of mono- and divalent cations such as $Ca^{2+}$, $Mg^{2+}$, $K^+$, and $Na^+$ (Bakliwal, & Pawar 2010). The electrolytes present in the tear fluid cause the gelation of the polymer when it is instilled in the eye and this in turn results in a longer residence time and increased bioavailability of the drug (Ludwig 2005). Based on previous formulation studies, the polymer formulation is a non-irritant and safe for in vivo use (Rupenthal, Green, & Alany 2011).

A 0.5% solution was prepared by first heating distilled water to 80° C. followed by the addition of gellan gum (Kelcogel™ USA) with constant stirring. Once the powder was completely dissolved, the solution was cooled and stored at 4° C. The appropriate amounts of growth factors were added to the runny gel with constant stirring. A ten times higher concentration of growth factors than that used in the culture medium was used to make up for the drug lost through naso-lacrymal drainage and blinking. The eye drop gel included a final concentration of 100 ng/ml TGFβ3 and approximately 4 μg/ml dexamethasone.

Treatment with Neurogenic and Chondrogenic Factors

Figure 3:
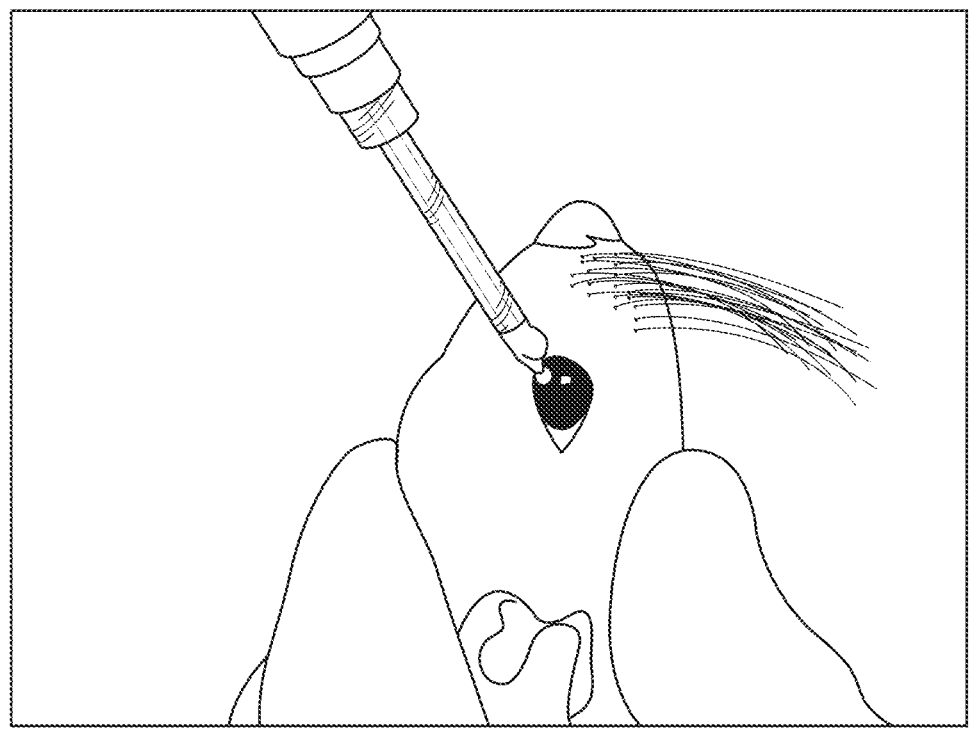
FIG. 3: Growth factor eye drops instilled in the eye of adult male Wistar rat.
Figure 4:
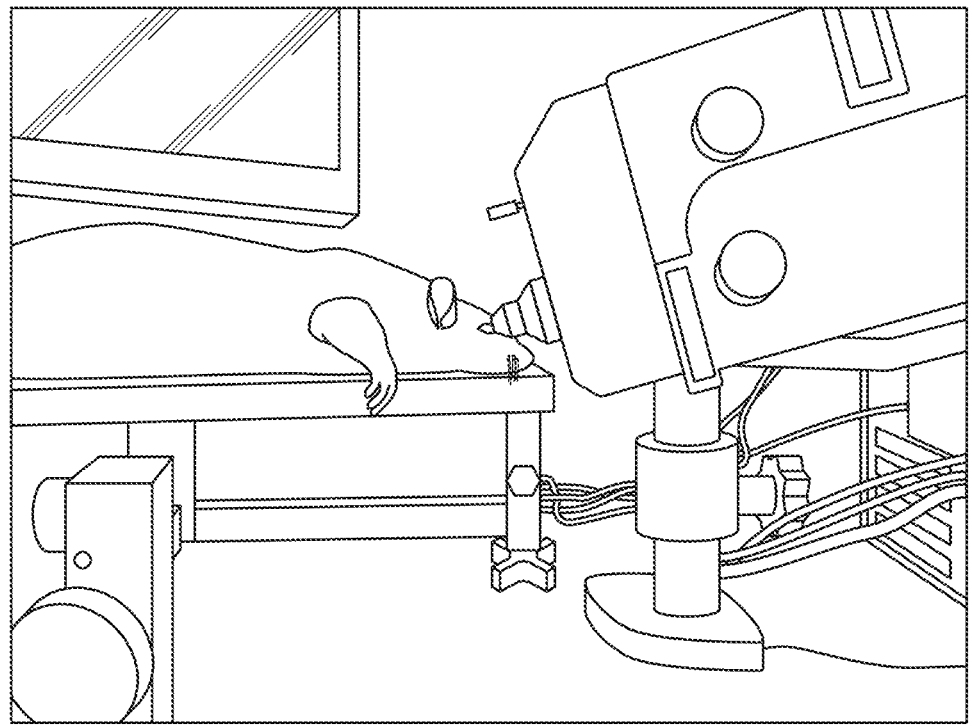
FIG. 4: Phoenix Micron IV in vivo eye imaging system set up specific for imaging rat eyes.
Figure 5A:
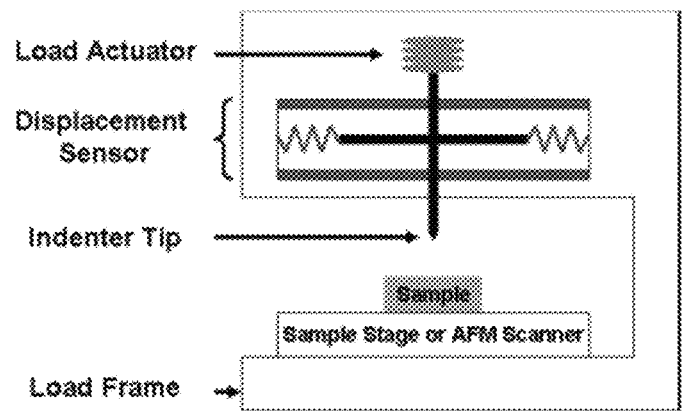
FIG. 5A: Schematic of a nanoindenter system.
Figure 5B:
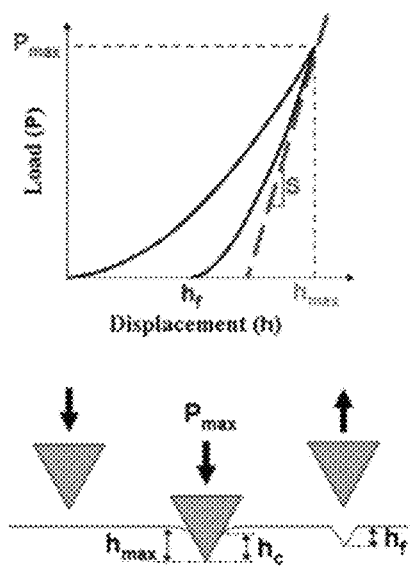
FIG. 5B: Schematic of a typical load-displacement curve obtained during the indentation process which is used to calculate corneal elasticity and hysteresis. $P_{max}$=maximum load applied; $h_{max}$=penetration depth; $h_c$=contact depth (the height of the contact between the tip and the sample); $h_f$=final depth; S=unloading stiffness.

The animals were manually restrained and approximately 15 pL of the eye drops were instilled in the right eye (FIG. 3). The contra lateral eye was used as the control eye. Thrice daily eye drops were administered for up to 5 days for neuronal specification and for up to 8 weeks for chondrogenic specification.

Example 5: Immunohistochemical (IHC) Analysis

Tissue Harvesting and Treatment

At the end of the treatment the animals were euthanised using a carbon dioxide chamber. The eyes were harvested and rinsed in phosphate buffered saline. The corneas were then dissected out carefully and fixed in 4% paraformaldehyde (PFA) for 1 hour and treated with sucrose solution in order to cryoprotect the tissue before freezing and sectioning. Sucrose as a cryoprotection is a dehydrant that prevents the formation of ice crystal artefact in frozen tissue sections. In the case of slow freezing of the tissue cryoprotection is particularly important.

Briefly, the corneas were immersed in 20% sucrose solution for 5 hours at 4° C. and then moved to a 30% sucrose solution and kept at 4° C. until the tissue sinks (usually overnight). The corneas were then embedded in OCT compound and immersed in liquid nitrogen to bring about rapid freezing. The frozen blocks of tissue were stored at −80° C. until further use. Approximately 10-15 μm thick cryostat sections were mounted on SuperFrost™ Plus slides and the slides were stored at −80° C. until needed. In the case of cell cultures, the cells cultured on coverslips were rinsed with PBS and fixed with 4% PFA for 15 minutes. Coverslips were immersed in PBS until further use.

Immunohistochemistry

For tissue cryosections, before carrying out immunohistochemistry, the slides were kept at room temperature for 15-20 minutes. The OCT was washed off using PBS and the zone around the tissue demarcated using a wax pen. The tissue slices were first incubated with a blocking solution of 10% normal goat serum for 1 hour followed by overnight incubation with the appropriate dilution of primary antibody at 4° C. The slides were then rinsed three times in PBS before incubation with the appropriate dilution of secondary antibody. The secondary antibody was left on for 2 hours at room temperature. Slices were counterstained with the nuclear marker 4', 6'-diamidino-2-phenylindol (DAPI) and mounted in Citifluor antifade agent (ProSciTech, Australia). An Olympus FluoView™ FV-1000 confocal laser scanning microscope (405 nm, 473 nm, and 559 nm wavelength lasers) and Leica DMRA fluorescence microscope were used for imaging.

TABLE 3

Antibodies used

| Antibody | Supplier/Cat. No. | Dilution used |
|---|---|---|
| Primary antibodies | | |
| Mouse anti Collagen Type I | Abcam/ab63080 | 1:2000 |
| Mouse anti Collagen Type II | Millipore/MAB8887 | 1:200 |
| Mouse anti Collagen Type III | Biogenesis/2150-0081 | 1:100 |
| Mouse anti Vimentin | Sigma/V6630 | 1:1000 |
| Mouse anti α Smooth muscle actin | Novocastra/NCL-SMA | 1:100 |
| Secondary antibodies | | |
| Goat anti mouse Alexa 568 | Molecular probes ®/ A-11031 | 1:500 |
| Goat anti rabbit Alexa 488 | Molecular Probes ®/ A-11034 | 1:500 |
| Goat anti mouse Alexa 488 | Molecular Probes ®/ A-11001 | 1:500 |

Example 6: Gene Expression Analysis

RNA Isolation and cDNA Synthesis

The mRNA extraction from samples was carried out using the PureLink® RNA MicroKit (Invitrogen). In brief, tissue samples were mixed with 0.75 ml TRIzol® and carrier RNA and homogenised using a hand held homogeniser (PRO Scientific, Inc.). The samples where then incubated with 0.2 ml of chloroform followed by centrifugation at 12000 rpm and 4° C. for 15 minutes. The upper phase was separated and was mixed with ethanol and then transferred to the collection column tube.

The RNA was collected on the column by centrifuging at 12000 rpm for 1 minute. The flow-through was discarded and the extracted RNA treated with deoxyribonuclease (DNAse). The column was washed several times with the buffers provided and the RNA was finally dispersed in ribonuclease (RNAse) free water. The concentration was determined using a NanoDrop® (Thermo Scientific) and the mRNA was stored at −80° C.

The SuperScript® VILO™ cDNA Synthesis Kit (Invitrogen™, Life Technologies) was used to prepare cDNA. Briefly, 100 ng of RNA was incubated at 25° C. for 10 minutes with VILO™ Reaction Mix, SuperScript® Enzyme Mix, and RNAse free water. The samples were then incubated at 42° C. for 120 minutes followed by 85° C. incubation for 5 minutes. The cDNA was stored at −20° C.

Quantitative PCR Using TaqMan® Gene Expression Assays

TaqMan® Gene Expression Assays for the genes of interest were obtained. In the PCR step, 10 μL of TaqMan® Universal Master Mix II was combined with 1 μL of the assay, approximately 25 ng of cDNA and 9 μL water to make up a volume of 20 μL. The tubes were vortexed and centrifuged briefly to spin down the contents. Each cDNA sample was prepared in triplicate and pipetted into a 384 well plate. 20 μL of each reaction mixture was loaded into each well of a MicroAmp® Optical 384-Well Reaction Plate (Applied Biosystems). The plate was then covered with a MicroAmp® Optical Adhesive Film (Applied Biosystems) and the plate was centrifuged briefly to eliminate air bubbles. The plate was transferred to the 7900HT Fast Real-Time PCR System and was run using the following thermal cycling parameters, 50° C. for 2 min, 95° C. for 10 minutes followed by 40 cycles of 95° C. at 15 sec and 60° C. at 1 minute. Results were analysed as described in the previous section.

TABLE 4

TaqMan ® gene assays used for QPCR

| Gene symbol | Gene name | Assay ID |
| --- | --- | --- |
| Col1a1 (Rat) | Collagen, type I, alpha 1 | Rn01463848_m1 |
| Col2a1 (Rat) | Collagen, type II, alpha 1 | Rn01637085_m1 |
| Col2a1 (Rat) | Collagen, type II, alpha 1 | Rn01637087_m1 |
| Pop4 (Rat) | Ribonuclease P protein subunit p29 (housekeeping gene) | Rn02347225_m1 |
| COL2A1 (Human) | Collagen, type II, alpha 1 | Hs00264051_m1 |
| CDKN1A (Human) | Cyclin-Dependent Kinase Inhibitor 1 (housekeeping gene) | Hs00355782_m1 |

Example 7: Testing of Biomechanical and Optical Properties of Corneas Following In Situ Stromal ECM Protein Deposition Examination of Anterior Segment (Frontal Structures) of the Rodent Eye Corneal biomechanics have been shown to be relevant in the diagnosis and treatment of various corneal diseases and provide insight into the structure of the cornea and its relation to corneal physiological function. Corneas that have undergone treatment to bring about the deposition of ECM protein also need to be tested for corneal opacity as reduced transparency would be undesirable.

The Phoenix Micron IV Rodent eye Imaging System (Phoenix Research Labs) was used to examine the corneas of treated rats. Rats were first sedated using an intraperitoneal injection of ketamine and Domitor® (3:2). The slit-lamp attachment of the Micron IV imaging system was used to examine the layers of the cornea in detail and check corneal integrity and transparency. Retinal imaging was also done to check corneal transparency. Following imaging, the rats were administered Antisedan® (atipamezole) for reversal of the sedative.

Nanoindentation Measurements of In Vitro and In Vivo Treated Corneas

Nanoindentation provides mechanical measurements of materials of interest through the application of ultra-small forces perpendicular to the sample plane of interest and measurement of the resultant sample indentation (Dias & Ziebarth 2013). Nanoindentation has recently emerged as a powerful tool for measuring nano- and microscale mechanical properties in tissues and other biomaterials (Ebenstein & Pruitt 2006). The more recent advancement of in situ scanning probe microscopy (SPM) imaging, where the nanoindenter tip is simultaneously used as a 3D imaging device combined with nanoindentation has enabled a new wave of novel materials research (Dickinson & Schirer 2009). Force, displacement, and time are recorded simultaneously while a nanoindentation tip is pushed into the corneal tissue under a controlled load. The forces applied during nanoindentation can be as small as a few nanoNewtons or as large as several Newtons enabling a range of size scales to be studied. Nanoindentation tests are output as a load-displacement curve which can be analysed using well defined equations to calculate the mechanical properties relating to rigidity, integrity, and elasticity of the cornea.

Human keratoconic corneas were put into organotypic culture either in control medium or in medium containing the specific ECM protein inducing reprogramming factors. Nanoindentation measurements were then taken at the end of the treatment time. For the in vivo study, the animals were manually restrained and approximately 15 μL of the gel eye drop formulation containing the reprogramming factors were instilled in the right eye of each Wistar rat. The contra lateral eye was used as the control eye. Eye drops were administered thrice daily for up to seven weeks. Nanoindentation measurements were recorded after week 1, week 3, or week 7 of the treatment period on isolated eyes.

Figure 6A:
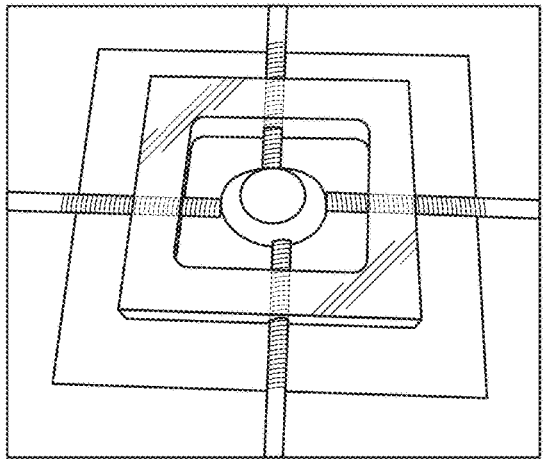
FIG. 6A: Nanoindentation rigs designed to hold the human corneal button.
Figure 6B:
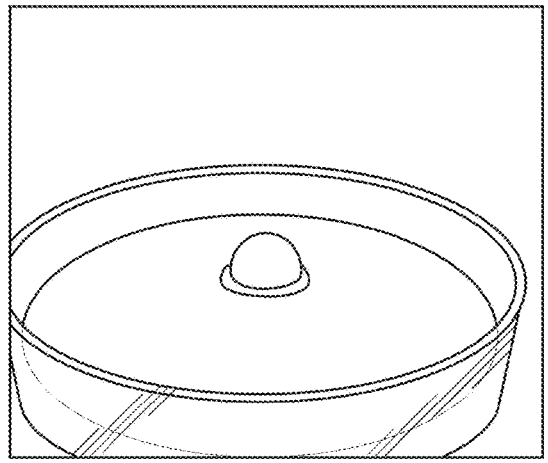
FIG. 6B depicts the rat globe.
Figure 6C:
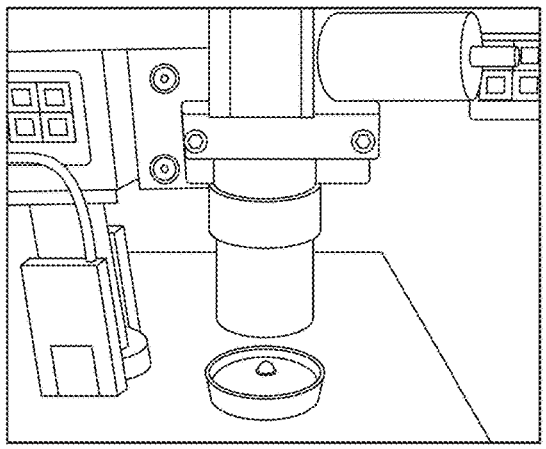
FIG. 6C: The central section of the cornea is located by using the microscope.

Nanoindentation testing was carried out at the Chemical and Materials Engineering lab at the University of Auckland. In order to test the cornea in its natural position a mould was required for nanoindentation. Previous studies have used polystyrene and blue tack to hold the corneas in place. The effect of the mould deforming under the load was a potential source of error so a hard mould was decided on for testing. The first material that was used to create a mould was conventional play dough. This was formed to the exact shape and curvature of human cornea samples (FIG. 6C). The play dough was then left to harden over the next two days before being used in testing. The testing of the rat eyes was slightly different as the entire globe was used. To hold the globes in place a petri dish filled with a resin and having small indent to hold the globe was used (FIG. 6C). PBS was used to keep the samples from drying out.

Because the samples are very soft biological samples a conospherical fluid tip was used for all nanoindentation testing. The indent load used for the human samples was 50 μN. For the rat globes a range of loads between 3 and 5 μN were used. The fibre optic light was switched on and the sample placed directly under the stream of light from the microscope. The central section of the cornea was placed directly in the stream of light as accurately as possible (FIG. 6C). The sample was focused by adjusting the Z slider until the surface of the cornea could be observed in good resolution. To ensure that the focus was on the central highest point of the cornea sample, the view was moved in the x and y directions to observe how the focus changed.

Figure 6D:
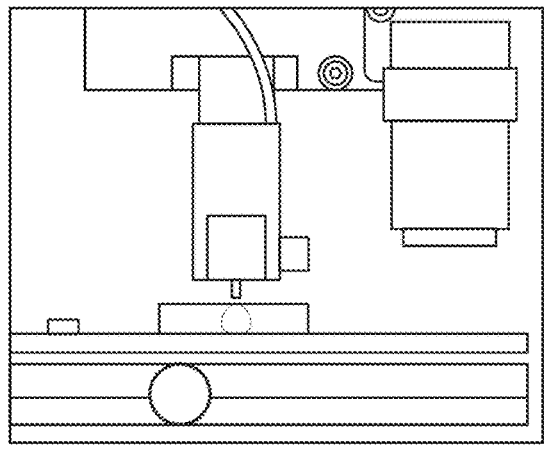
FIG. 6D: Once located the indenter probe is used.

Once the data collection point was focused on the centre of the cornea, the sample boundary was defined and a quick approach was performed. Before indenting the load function had to be set up correctly. The actual indentation process is automated by the Hysitron Triboindenter® (FIG. 6D). The pre-defined load was placed on the indenter tip which penetrates the sample until it reaches a defined limit. The tip was then held for 10 seconds before the tip was unloaded from the sample. The hardness of the sample is determined by the area of residual indentation (Ar) after the tip is unloaded.

$$\text{Hardness} = \frac{\text{Maximum Load }(P)}{\text{Area of residual indentation }(Ar)}$$

Where $P_{max}$ is the maximum indentation load and Area is the contact area of the conospherical tip with the sample. The reduced elastic modulus is a representation of the elastic modulus in both the sample and the indenter tip as shown by the following equation:

$$\left(\frac{1}{Er}\right) = \left(\frac{1-vi^2}{Ei}\right) + \left(\frac{1-vm^2}{Em}\right)$$

Where i referrers to the indenter and m refers to the sample material. The reduced elastic modulus tells us how elastic a sample is. Because the same indenter tip is used for each test the reduced elastic modulus can be used to compare the elasticity in each sample being tested.

Example 8: Adult Human Corneal Keratocytes Produce Cartilage Specific Collagen Type II Upon Treatment with Exogenous TGFβ3 and Dexamethasone It is known that one growth factor may act on several types of cells with similar or varied effects whilst more than one growth factor may share similar biological functions. When choosing growth factors, cytokines, and chemicals that might bring about collagen deposition in the corneal stroma it was important to consider the known effects of certain exogenous factors. In the present experiments, a combination treatment of TGFβ3 and dexamethasone was utilised.

Most of the evidence for the effects of TGFβ3 and dexamethasone has been obtained by studies done on their effects on stem/progenitor cells (Schuldiner, Yanuka, Itskovitz-Eldor, Melton, & Benvenisty 2000; Worster, Nixon, Brower-Toland, & Williams 2000). A combination of TGFβ and dexamethasone has been previously used to induce progenitor cells to differentiate into chondrocytes in vitro (Diekman, Rowland, Lennon, Caplan, & Guilak 2009; Johnstone et al. 1998; Kolambkar, Peister, Soker, Atala, & Guldberg 2007; Winter et al. 2003). Furthermore, dexamethasone, a synthetic steroid drug has been used to treat inflammatory eye conditions. Therefore a combination of TGFβ3 and dexamethasone was used in the chondrogenic differentiation medium to drive the differentiation of keratocytes towards a chondrocyte phenotype.

In the present experiments, the expression of type I and type II collagen was specifically noted. It is known that fibrillar types of collagen such as types I and II self-assemble and crosslink to form highly crystalline fibres exhibit a very high stiffness, low extensibility and a remarkable elastic energy storage capacity (Wells 2003). It is the crosslinking which contributes towards the stiffness and tensile strength of the fibres.

The corneal stromal extracellular matrix (ECM) is composed of tightly packed heterotypic collagen fibrils made up mostly of collagen types I and V. Similar to corneal fibrils, cartilage fibrils are heterotypic (made up of types II and XI) and have a uniform diameter of 25 nm (slightly smaller than corneal fibrils) (Mendler, Eich-Bender, Vaughan, Winterhalter, & Bruckner 1989). Collagen II is the major fibril component of cartilage and is similar to collagen I in that the molecule essentially consists of a single uninterrupted helical domain 300 nm in length. Owing to their similarities, collagens II and XI are considered to be the cartilage analogues of collagens I and V (corneal stroma collagens) in other tissues.

Figure 7A:
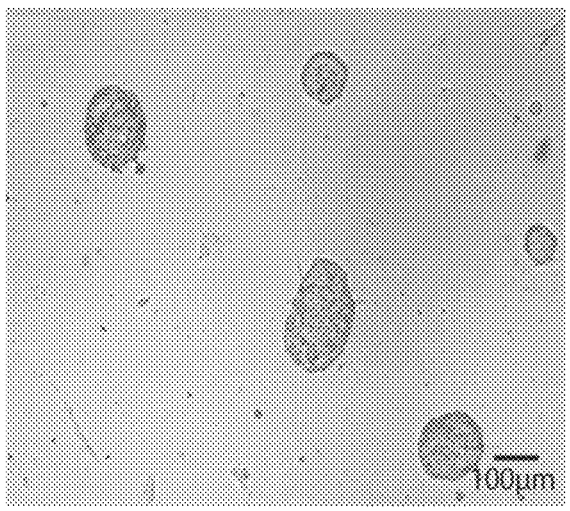
FIG. 7A: Corneal keratocytes seeded in chondrogenic differentiation medium. Keratocytes cultured for 3 weeks in chondrogenic differentiation medium containing TGFβ3 and dexamethasone formed spheres, which were labelled with nestin around the periphery of the spheres.
Figure 7B:
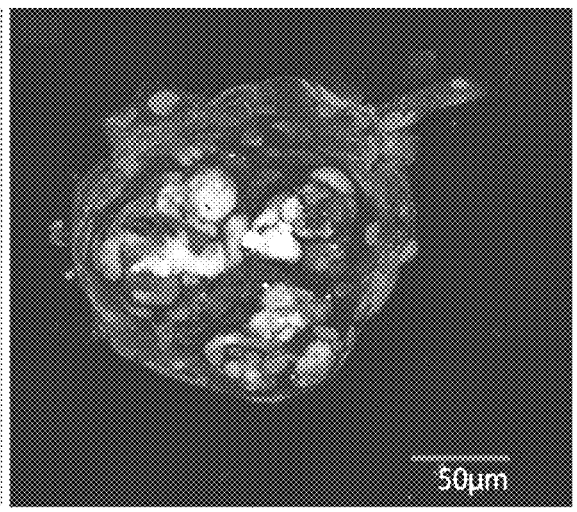
FIG. 7B: Corneal keratocytes seeded in chondrogenic differentiation medium. Keratocytes cultured for 3 weeks in chondrogenic differentiation medium containing TGFβ3 and dexamethasone formed spheres, which were labelled with collagen type II within the core.
Figure 7C:
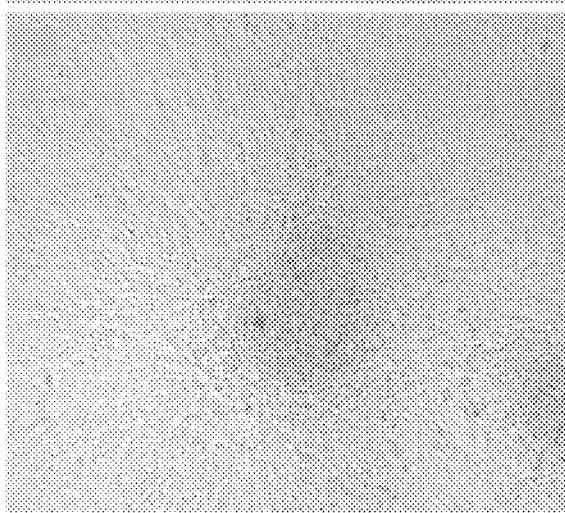
FIG. 7C: The culture medium was then switched to serum containing fibroblast proliferation medium for 1 week, causing cells from the spheres to spread out and populate the dish.
Figure 7D:
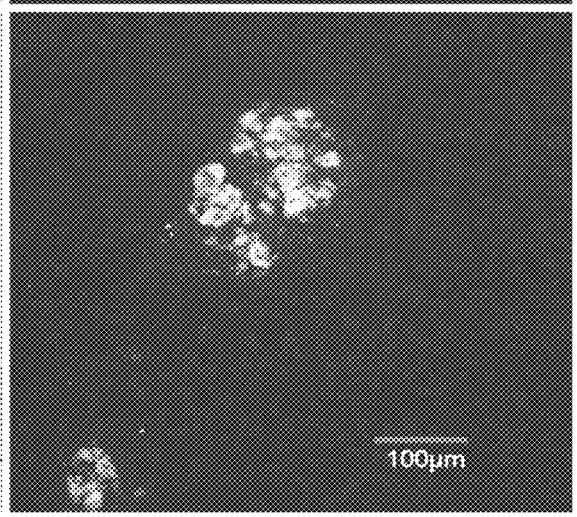
FIG. 7D: Cells in monolayer were negative for type II collagen whereas the cell clusters remained positive for collagen type II.

In the present experiments, corneal keratocytes from adult corneas were seeded in either the chondrogenic differentiation medium containing TGFβ3 and dexamethasone or a standard fibroblast proliferation medium. Within 2-3 days the keratocytes seeded in the chondrogenic differentiation media formed cell aggregations/spheres (FIG. 7A) approximately 50-100 μm in diameter. The spheres labelled for the chondrocyte specific collagen type II in the central portion and nestin around the periphery (FIG. 7B). Furthermore, once the spheres were placed in the fibroblast proliferation media cells from the spheres started spreading outwards (FIG. 7C) to populate the culture dish thereby forming a cell monolayer. The regions where the cells had once been aggregated labelled for collagen type II whereas the cells in monolayer did not (FIG. 7D).

Keratocytes seeded in the fibroblast proliferating medium formed an even monolayer of fibroblast-like cells (FIG. 8A) which did not label for either nestin or collagen type II (FIG. 8B). When the media was changed to chondrogenic differentiation medium there were no changes in the appearance of the culture and cells remained collagen type II negative. These results suggest that cell aggregation appears to be important for cartilage-like ECM production. Keratocytes seeded into fibroblast proliferation medium failed to form the necessary cell aggregations. Therefore, in order to form fibroblast clusters, the confluent fibroblasts were dissociated from the culture dish, pelleted, and grown as a pellet culture in chondrogenic differentiation medium for a further three weeks. Cell pellets labelled positive for the corneal stroma specific ECM protein keratocan but not the cartilage specific ECM protein type II collagen (FIG. 8F and FIG. 8G).

Example 9: Keratocytes in Adult Human Corneas and Adult Rat Corneas Secrete Collagen Type II Containing ECM when Treated with TGFβ3 and Dexamethasone Slices of adult human cornea were placed in organotypic slice culture in either control medium or chondrogenic differentiation medium for two weeks. The tissue slices were then labelled for the chondrocyte specific ECM protein collagen type II and the native corneal collagen type I. Positive labelling was seen only in the TGFβ3 and dexamethasone treated corneas (FIG. 9C and FIG. 10B). It was found that a treatment period of two weeks resulted in deposition of type II collagen within the stromal ECM of treated corneas (FIG. 9C). Treatment for 1 week did not result in any visible deposition of type II collagen in the stromal ECM (FIG. 9B).

The amount and pattern of the native collagen type I appeared to be slightly altered in the treated corneas. In general, the intensity of the labelling was similar but the distribution was more extensive and the amount of labelling was higher in the untreated corneas (FIG. 9D). Furthermore, the newly produced type II collagen was laid evenly and in an ordered fashion in the ECM without forming any large masses or aggregates. The labelling was clearly seen along the pre-existing collagen framework of the corneal stroma and was distributed across the entire thickness of the stromal layer.

The in vitro human corneal tissue experiment was then extended to an in vivo rodent study wherein the right corneas of male Wistar rats were treated for two weeks with a thrice daily administration of 15 µl of a gellan gum based eye drop formulation of TGFβ3 and dexamethasone. After two weeks the rats were euthanised and the corneas processed for immunohistochemistry. Only the treated corneas labelled positive for collagen type II with a higher degree of deposition observed in the anterior part of the cornea (FIG. 10D and FIG. 10E). Thus, only corneal slices cultured in the chondrogenic differentiation medium were positive for type II collagen. Furthermore, type II collagen was laid down in uniform layers along the pre-existing collagen framework of the stroma.

Example 10: Induction of Collagen Type II Deposition in Keratoconic Corneas

Figure 11A:
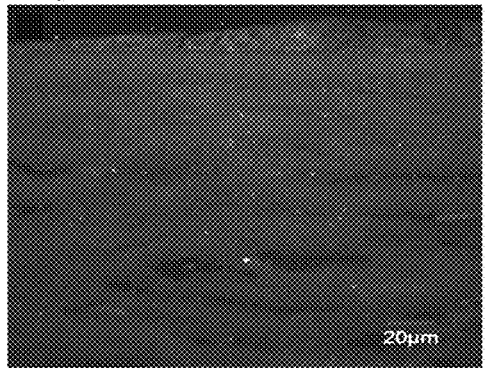
FIG. 11A: Keratoconic corneal button cultured in vitro in control medium for 2 weeks and labelled for collagen type II.
Figure 11B:
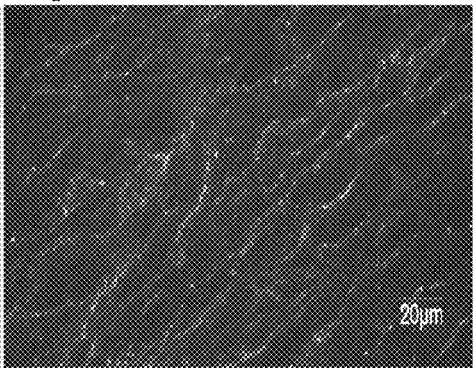
FIG. 11B: Keratoconic corneal button cultured in vitro chondrogenic differentiation medium for 2 weeks and labelled for collagen type II.

The inventors next looked to confirm that the in vivo reprogramming observed in their studies could be utilised in treatments for keratoconus. Experiments were carried out to affirm that keratocytes in keratoconic corneas were amenable to the induction of collagen type II deposition. Keratoconic corneal buttons obtained after corneal transplant surgery were placed into culture as soon as they were obtained. Half of each button was put into control medium and the other half placed in chondrogenic differentiation medium and maintained for 2 weeks. After 2 weeks the tissue was processed for either immunohistochemistry or mRNA extraction. The stromal ECM of only the treated half of the cornea was positive for type II collagen (FIG. 11B). Although the intensity of the labelling was lower in keratoconic tissue when compared to normal corneal tissue, the labelling pattern was similar and followed an ordered arrangement along the backbone of pre-existing collagen lamellae.

Figure 11C:
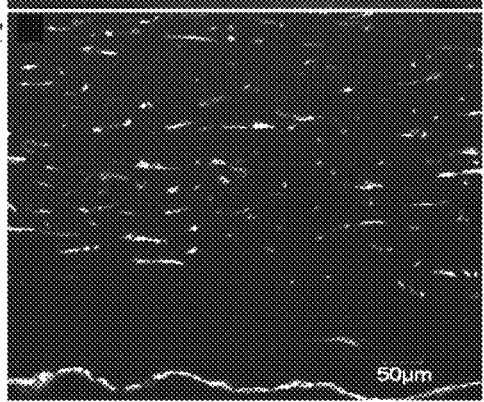
FIG. 11C: Keratoconic corneal button cultured in vitro in control medium for 2 weeks and labelled for vimentin.
Figure 11D:
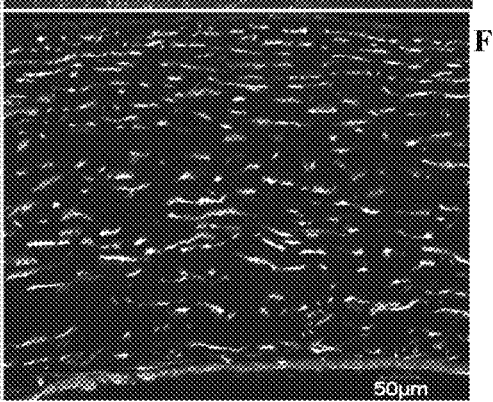
FIG. 11D: Keratoconic corneal button cultured in vitro chondrogenic differentiation medium for 2 weeks and labelled vimentin.
Figure 11E:
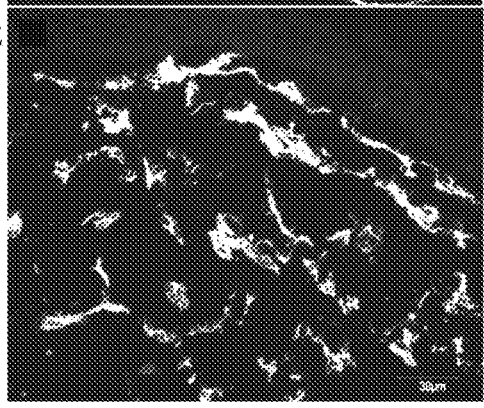
FIG. 11E: Keratoconic corneal button cultured in vitro in control medium for 2 weeks and labelled for vimentin.
Figure 11F:
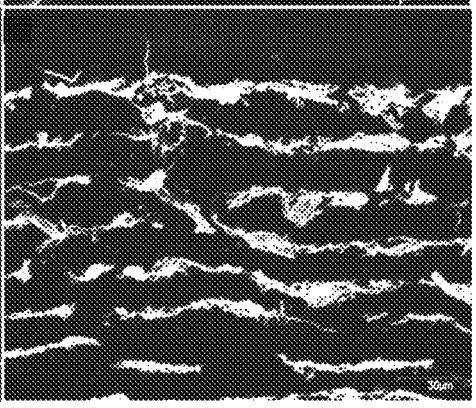
FIG. 11F: Keratoconic corneal button cultured in vitro in chondrogenic differentiation medium for 2 weeks and labelled for vimentin. Compared to the labelling in normal human corneas the labelling of type II collagen in treated keratoconic corneas (FIG. 11B) was weaker. However, the deposition of type II collagen had a similar pattern to that previously seen after in vitro and in vivo treatment of normal human and rat corneas. The fibroblast population in the treated half of the keratoconic button (FIG. 11D) and (FIG. 11F) increased in number and the keratocytes appeared healthier and intact with multiple, long cell processes (FIG. 11F), when compared to the untreated half of the keratoconic cornea, (FIG. 11C) and (FIG. 11E).
Figure 12A:
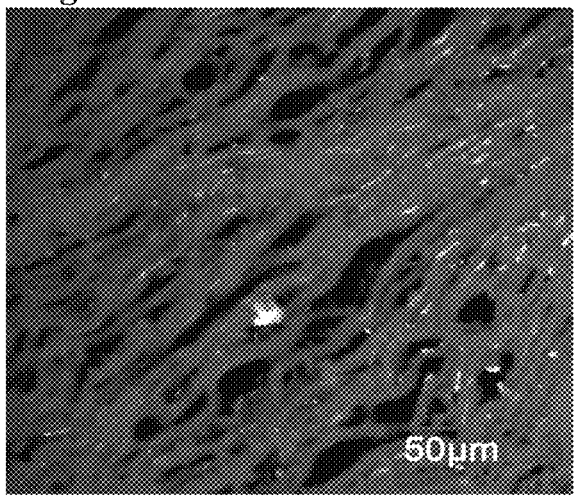
FIG. 12A: Ex vivo cultured human keratoconic cornea cultured for 3 weeks in control medium and labelled for alpha smooth muscle actin (αSMA).
Figure 12B:
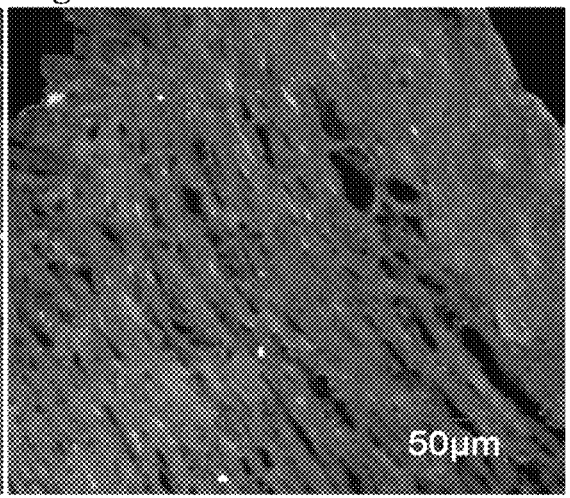
FIG. 12B: Ex vivo cultured human keratoconic cornea cultured for 3 weeks in chondrogenic differentiation media and labelled for alpha smooth muscle actin (αSMA).
Figure 12C:
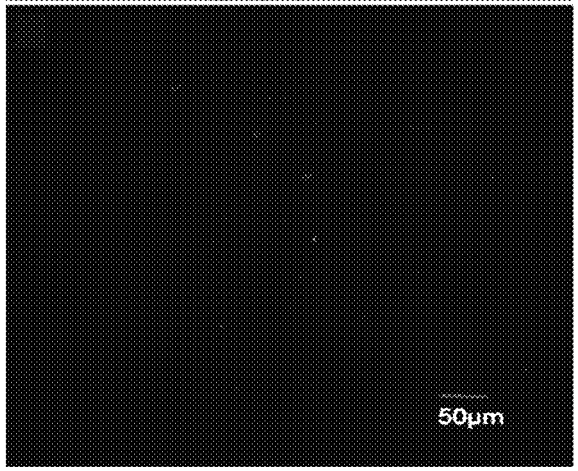
FIG. 12C: Ex vivo cultured human keratoconic cornea cultured for 3 weeks in control medium and labeled for type III collagen.
Figure 12D:
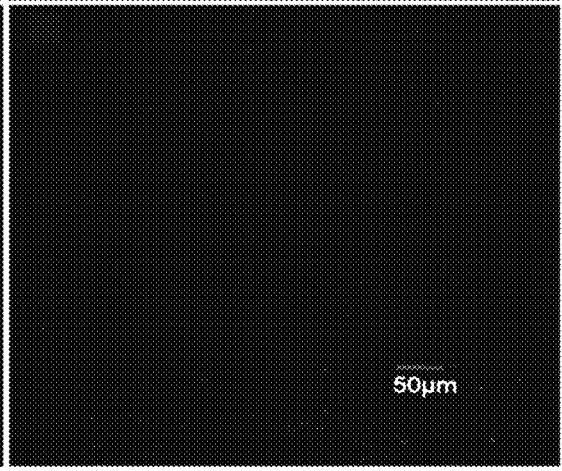
FIG. 12D: Ex vivo cultured human keratoconic cornea cultured for 3 weeks in chondrogenic differentiation media and labelled for type III collagen. There was stronger labelling for αSMA in stromal layer of corneas cultured in control medium (FIG. 12A), when compared to corneas cultured in chondrogenic differentiation medium. Corneas cultured in either of the two media did not label positively for type III collagen.

Vimentin labelling revealed stark differences between keratocytes in the untreated and treated keratoconic corneas. In general the keratocyte density was lower in the untreated corneas with a scarcity of cells in the posterior part of the cornea (FIG. 11C). Also, the keratocytes in treated corneas appeared more filamentous and complete in morphology when compared to keratocytes in untreated corneas (FIG. 11E and FIG. 11F). Keratocytes in treated corneas were longer and had a larger number of cell processes which labelled strongly for Vimentin when compared to the keratocytes in the untreated corneas.

Example 11: TGFβ3 and Dexamethasone Treatment does not Induce Deposition of Fibrotic Proteins or Cause Corneal Opacity Human corneas cultured in the chondrogenic differentiation medium for up to three weeks were labelled for collagen type III and αSMA which are associated with fibrosis and scarring (Gabbiani 2003; Karamichos et al. 2012). There was no evidence of any fibrotic matrix deposition, on the other hand there was a higher degree of αSMA labelling in the control tissue (FIG. 12). These results confirm previous findings that, unlike TGFβ1 and TGFβ2, TGFβ3 does not induce the differentiation of corneal keratocytes into myofibroblasts.

Figure 13A:
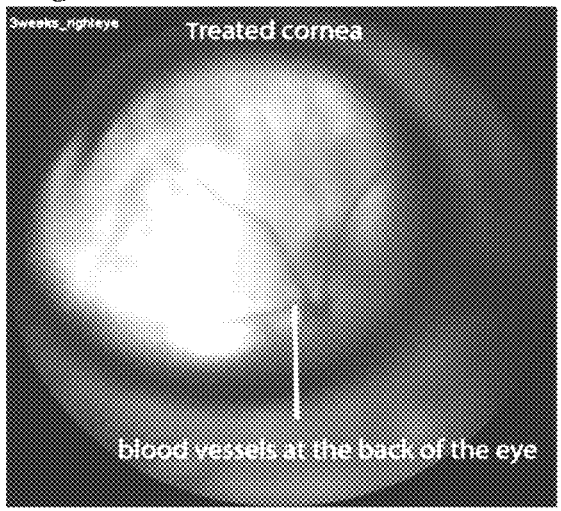
FIG. 13A and FIG. 13C: Corneal transparency of in vivo treated corneas.
Figure 13B:
FIG. 13B and FIG. 13D: Corneal transparency of in vivo untreated corneas. After 3 weeks the treated and untreated corneas were indistinguishable from each other. The front view of the corneas (FIG. 13A) and (FIG. 13B) reveal a clear cornea through which light easily passes to reveal the blood vessels of the back of the eye very clearly. At 8 weeks the in vivo imaging of the cross section of the cornea reveals a clear, transparent cornea through which light easily passes. There were no signs of corneal opacity or scarring.
Figure 13C:
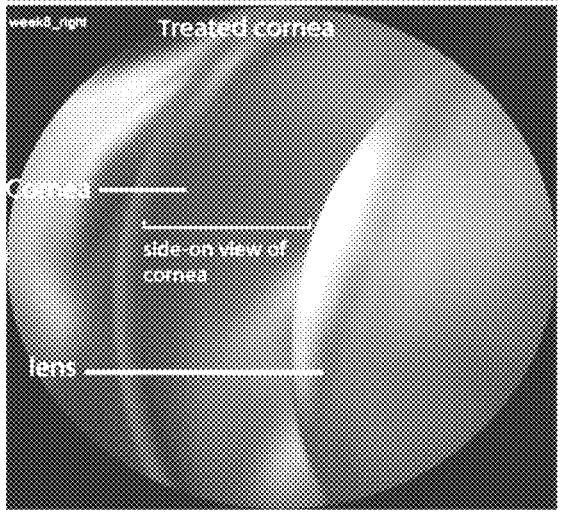
Figure 13D:
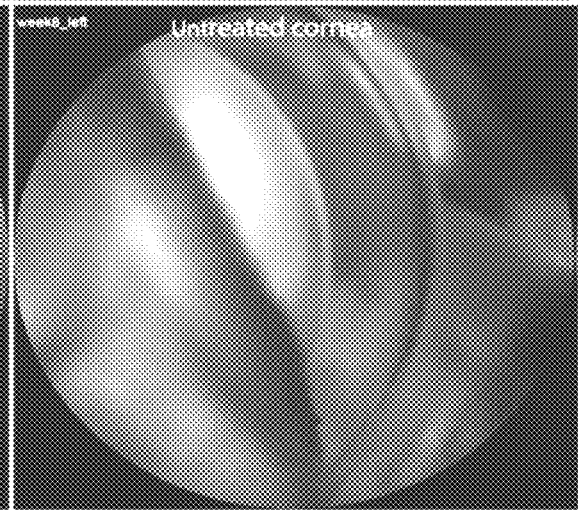

Slit lamp examination was performed on the live rats throughout the study period. Upon examination, treated and untreated corneas were indistinguishable with no signs of scarring or opacity. Back of the eye imaging to reveal the blood vessels showed clear corneas which did not obstruct the passage of light (FIG. 13A and FIG. 13B) and in vivo cross section imaging of the rat cornea using the Micron IV lens revealed transparent corneas through which light easily passed (FIG. 13C and FIG. 13D). There was no sign of any corneal opacity or cloudiness which would lead to the obstruction of light passing through the cornea.

Example 12: Change in mRNA Expression of Collagen Type II and Type I Upon Treatment In Vivo Rat corneas which were treated in vivo for 1 week, 7 weeks, and 3 weeks followed by a non-treatment period of 4 weeks were subjected to quantitative gene expression analysis. The aim was to determine whether type II collagen expression decreases again and/or permanently ceases after growth factor treatment is withdrawn. The effect of the treatment on native corneal collagen type II was also investigated.

When compared to the 7 weeks treated corneas, the 1 week treated corneas expressed very high levels of type II collagen. The expression levels dropped considerably upon withdrawal of the treatment as indicated by the graph in FIG. 14. For type I collagen expression, the 1 week and 7 week treated corneas were each compared to their untreated corneas. It was found that there was an initial spike in type I Collagen expression after 1 week treatment but by week 7 type I Collagen expression was significantly lower and comparable to its expression in the untreated cornea (FIG. 14B).

Example 13: Change in Biomechanical Properties of In Vitro and In Vivo Treated Corneas It was hypothesised that the laying down of type II collagen would affect the stiffness and elasticity of the corneas. In order to evaluate these changes, the in vivo rat corneas and ex vivo treated human corneas and their matching controls were subjected to nanoindentation testing.

Figure 15:
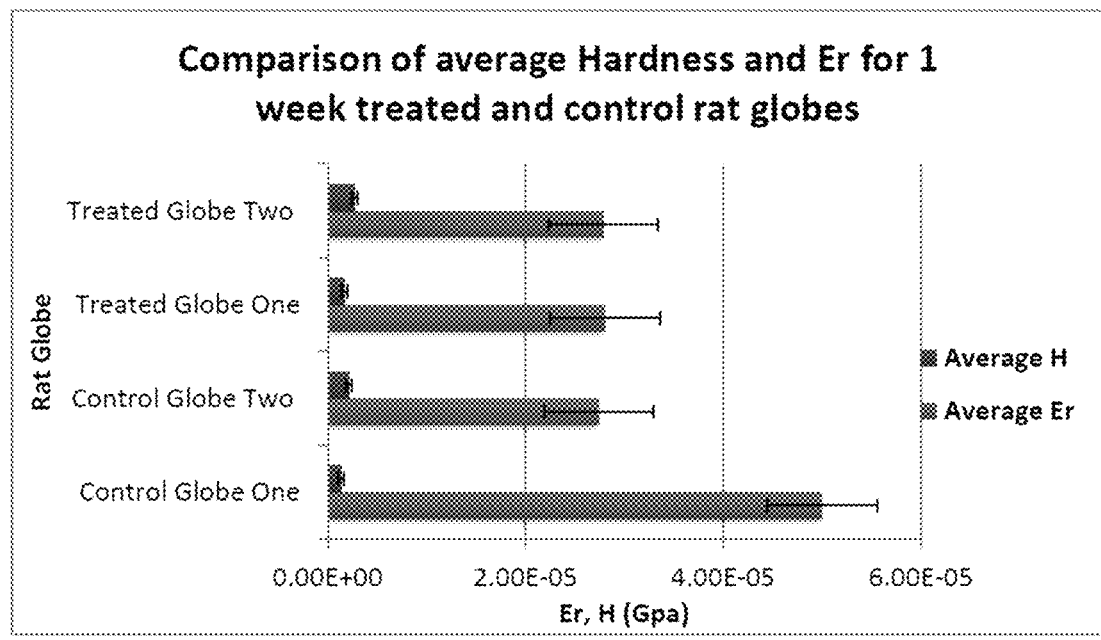
FIG. 15: Comparison of 1 week in vivo treated and untreated corneas does not reveal a significant difference in hardness (H) and reduced elastic modulus (Er).
Figure 16E:
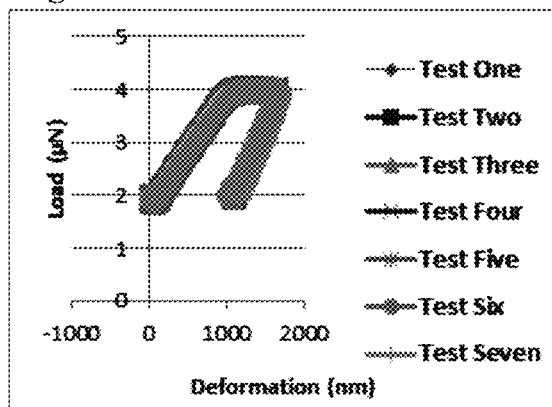
FIG. 16E and FIG. 16F: The corresponding graphs with the plotted values clearly show an increase in elastic modulus (Er) and hardness (H) in the treated corneas.
Figure 16E:
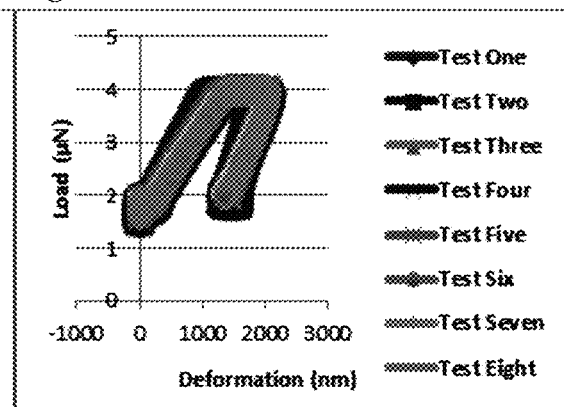
Figure 16E:
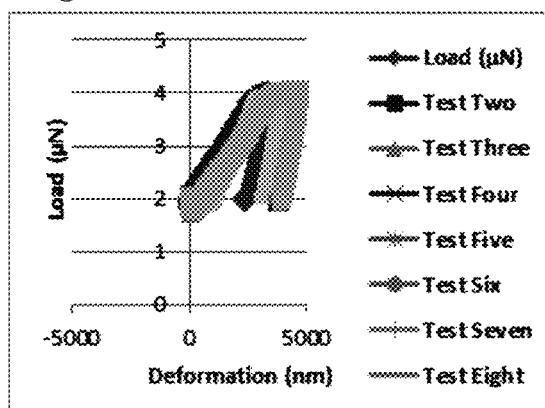
Figure 16E:
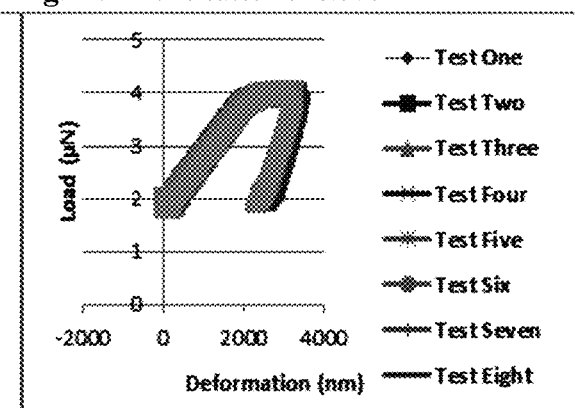
Figure 16E:
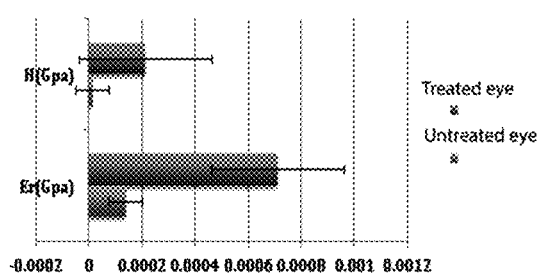
Figure 16F:
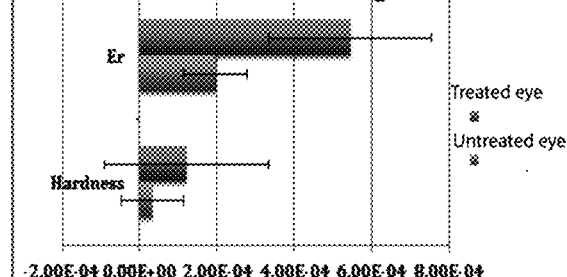

When compared to the untreated controls the 1 week in vivo treated rat corneas did not have a significant increase in either hardness or elasticity (FIG. 15). In the 3 week in vivo treated corneas, there was a clear difference between the treated and control eye. Each of the corneas was tested up to eight times and the resulting load deformation graphs obtained showed good reproducibility (FIG. 16). In the right eye exposed to the growth factor treatment, both the hardness and reduced elastic modulus were markedly higher. A matched pair of keratoglobus corneas that were cultured ex vivo in either the control medium or the chondrogenic differentiation medium for 6 weeks were also subjected to the same biomechanical testing. Once again, testing revealed a significant increase in hardness and elastic modulus in the treated cornea (FIG. 17).

Example 14: Comparative Combinations of Growth Factors and Steroids

An ex vivo study on sheep corneas was carried out in order to investigate the efficacy of other growth factor-steroid combinations in chondrogenic differentiation of corneal keratocytes.

Fresh sheep eyes were obtained from Auckland Meat Processors. The corneas were immediately excised and washed with povidone-iodine (PVP-I) and sodium thiosulphate solution. Then, 8 mm discs of sheep corneal tissue were cut using a trephine. One sheep corneal disc was placed in each of the culture conditions (outlined in Table 5) for 3 weeks. The corneal discs were then placed in an organotypic air-liquid interphase culture system.

Briefly, the explants of healthy tissue were cultured on 0.4 µm pore size cell culture inserts (Millicell, France) at the interface between culture medium and a $CO_2$ rich environment. Corneal sections were placed epithelium side up on cell culture plate inserts with 3 ml of culture medium. The culture media was changed every other day. The basal medium used was Dulbecco's Modified Eagle Medium (DMEM) supplemented with 1% Anti-Anti (antibiotic-antimycotic solution) and 1% GlutaMAX™ (GIBCO®). At the end of 3 weeks, each corneal disc was fixed in 4% paraformaldehyde (PFA) for 1 hour and treated with sucrose solution in order to cryoprotect the tissue before freezing and sectioning.

In brief, the corneas were immersed in 20% sucrose solution for 5 hours at 4° C. and then moved to a 30% sucrose solution and kept at 4° C. until the tissue sank (usually overnight). The corneas were then embedded in OCT (optimal cutting temperature) compound and immersed in liquid nitrogen to bring about rapid freezing. The frozen blocks of tissue were stored at −80° C. until further use. Approximately 4-6 40 µm thick cryostat sections were mounted on SuperFrost™ Plus slides and the slides were stored at −80° C. until needed. The corneal sections were then labelled for collagen type II.

For immunohistochemistry, the slides were kept at room temperature for 15-20 minutes. The OCT was washed off using PBS and the zone around the tissue was demarcated using a wax pen. The tissue slices were first incubated with a blocking solution of 10% normal goat serum for 1 hr followed by overnight incubation with mouse anti collagen II antibody (Millipore/MAB 8887) at 4° C. The slides were then rinsed three times in PBS before incubation with the appropriate dilution of goat anti mouse Alexa Fluor® 488 secondary antibody (Molecular Probes®/A-11001). The secondary antibody was left on for 2 hours at room temperature. Slices were counterstained with the nuclear marker 4′,6′-diamidino-2-phenylindol (DAPI) and mounted in Citifluor antifade agent (ProSciTech, Australia). An Olympus FluoView™ FV-1000 confocal laser scanning microscope (405 nm, 473 nm and 559 nm wavelength lasers) and Leica DMRA fluorescence microscope were used to visualise labelling.

Table 5 depicts the findings from this study. FIG. 20 shows representative images of collagen type II labelling in corneal sections, in each of the conditions.

TABLE 5

Tested combinations of growth factors and steroids

Figure 20A:
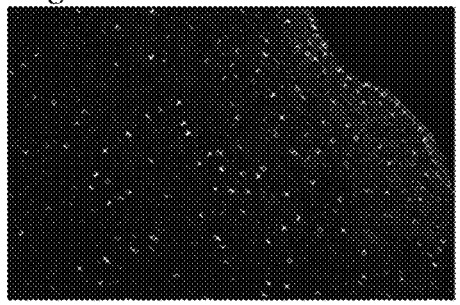
FIG. 20A: Sheep corneal tissue were cultured in BMP6, and labelled for cartilage specific collagen type II.
Figure 20B:
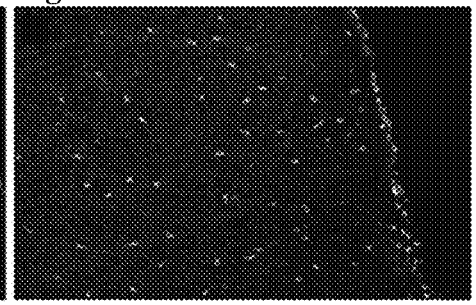
FIG. 20B: Sheep corneal tissue were cultured in BMP6+ hydrocortisone, and labelled for cartilage specific collagen type II.
Figure 20C:
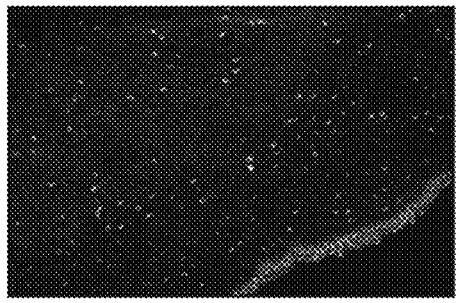
FIG. 20C: Sheep corneal tissue were cultured in TGFβ3+ hydrocortisone, and labelled for cartilage specific collagen type II.
Figure 20D:
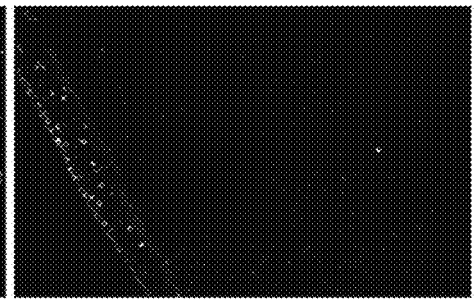
FIG. 20D: Sheep corneal tissue were cultured in BMP6+ dexamethasone, and labelled for cartilage specific collagen type II.
Figure 20E:
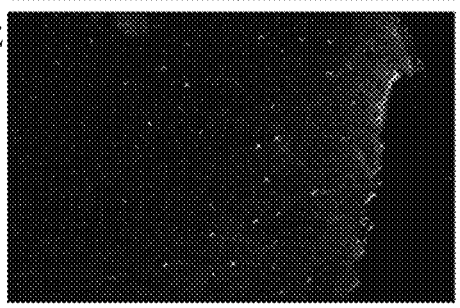
FIG. 20E: Sheep corneal tissue were cultured in TGFβ3+ prednisone, and labelled for cartilage specific collagen type II.
Figure 20F:
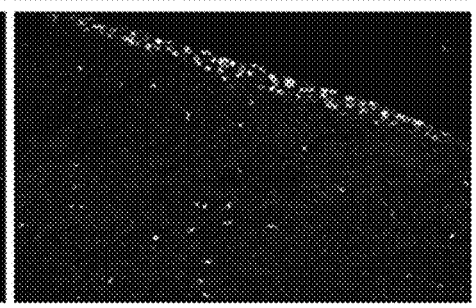
FIG. 20F: Sheep corneal tissue were cultured in TGFβ3+ Triesense® and labelled for cartilage specific collagen type II.
Figure 20G:
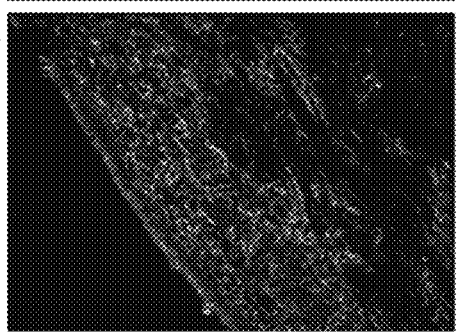
FIG. 20G: Sheep corneal tissue were cultured in TGFβ3+ dexamethasone at magnification, and labelled for cartilage specific collagen type II.
Figure 20H:
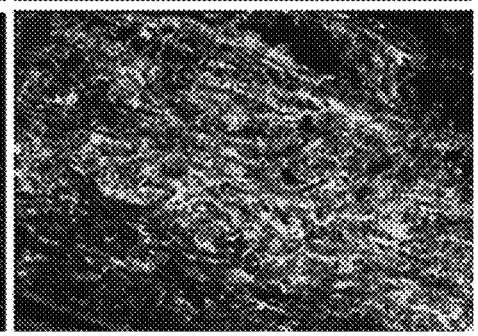
FIG. 20H: Sheep corneal tissue were cultured in TGFβ3+ dexamethasone at magnification, and labelled for cartilage specific collagen type II. Only TGFβ3 combined with dexamethasone produces collagen type II deposition

| Growth factor-steroid combination | Collagen type II deposition (Y/N) | Representative image |
|---|---|---|
| BMP6 | N | FIG. 20A |
| BMP6 + hydrocortisone | N | FIG. 20B |
| TGFβ$_3$ + hydrocortisone | N | FIG. 20C |
| BMP6 + dexamethasone | N | FIG. 20D |
| TGFβ$_3$ + prednisone | N | FIG. 20E |
| TGFβ$_3$ + Triesense ® | N | FIG. 20F |
| TGFβ$_3$ + dexamethasone | Y | FIG. 20G-FIG. 20H |

The results confirmed that the combination of TGFβ3 and dexamethasone is the only tested combination that elicited the desired response from the target cells (FIG. 20G and FIG. 20H). The other growth factor-steroid combinations failed to produce the desired changes in collagen type II in keratocytes (FIG. 20A-FIG. 20F. The results also confirmed the reprogramming of keratocytes in sheep corneas (FIG. 20G and FIG. 20H).

Previous studies have shown other growth factors and other steroid compounds to be unsuitable for corneal treatment and repair. TGFβ1 and TGFβ2 both produce fibrotic scarring (Carrington, Albon et al. 2006; Desmouliere, Chaponnier et al. 2005; Jester, Huang et al. 2002; Cowin et al. 2001; Shah et al. 1995). EGF negatively regulates chondrogenesis (Yoon 2000). Estrogen also negatively regulates chondrogenesis (Kato & Gospodarowicz 1985). Hydrocortisone has been shown to promote adipogenic rather than chondrogenic differentiation (Ghoniem et al. 2015; Lee, Kuo et al. 2004). These earlier studies show the significance of the present findings on TGFβ3 and dexamethasone, which act together to promote chondrogenic differentiation of corneal keratocytes and scar free corneal healing.

Example 15: Comparative Dosages for TGFβ3 and Dexamethasone

Prior to an in vivo study, experiments were performed to identify the various effective dosages for ex vivo treatments. A dose range study was carried out for TGFβ3 and dexamethasone by culturing sheep corneas in culture media containing these two factors in varying concentrations.

Figure 21:
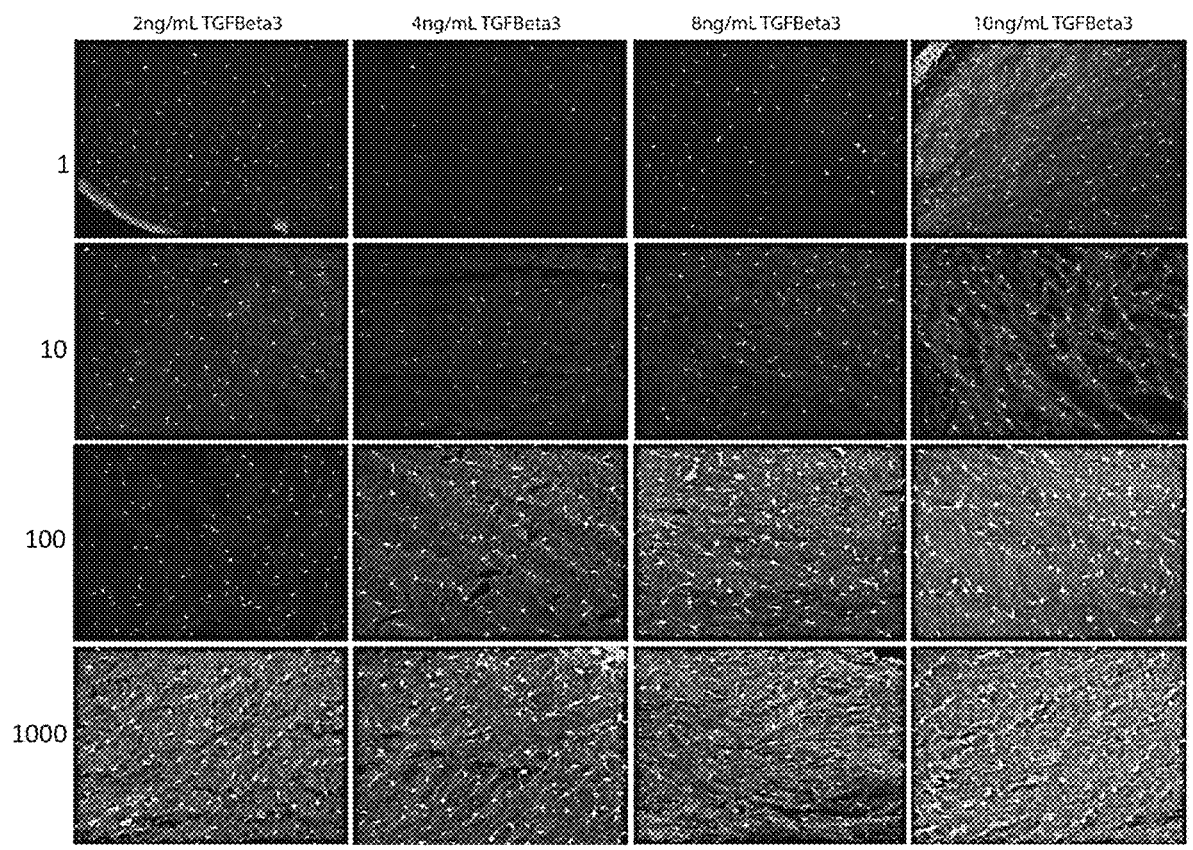
FIG. 21: Dose response study for combinations of TGFβ3 and dexamethasone. Sheep corneas were cultured for 3 weeks and labelled for collagen type II. (Row 1): 1 nM dexamethasone and 2, 4, 8, or 10 ng/ml TGFβ3; (Row 2): 10 nM dexamethasone and 2, 4, 8, or 10 ng/ml TGFβ3; (Row 3): 100 nM dexamethasone and 2, 4, 8, or 10 ng/ml TGFβ3; (Row 4): 1000 nM dexamethasone and 2, 4, 8, or 10 ng/ml TGFβ3.

Fresh sheep eyes were obtained and corneas were excised and treated as noted in Example 14. One sheep corneal disc was placed in each of the 16 culture conditions (FIG. 21) for 3 weeks. The corneal discs were cultured and then subjected to immunohistochemical and microscopic analysis as noted in Example 14. FIG. 21 shows representative images of collagen type II labelling in corneal sections in each of the conditions.

This study revealed that lower concentrations of TGFβ3 (2-4 ng/mL) and dexamethasone (1-10 nM) had lower efficacy ex vivo (FIG. 21, first and second rows). Higher doses, i.e., 8-10 ng/mL TGFβ3 and 100-1000 nM dexamethasone were efficient in inducing collagen type II deposition (FIG. 21, third and fourth rows).

These results confirmed the use of 100 nM dexamethasone and 10 ng/mL TGFβ3 as effective concentrations (FIG. 21, third row). Higher concentrations of dexamethasone (1000 nM, i.e., 400 ng/mL) were also shown to be effective (FIG. 21, fourth row). It was noted that the dexamethasone concentrations tested in this study were considerably lower than the concentrations used in commercially available eye drops (i.e., 1 mg/mL dexamethasone).

Example 16: Overview of Experimental Observations and Results

A combination of TGFβ1 and dexamethasone has been previously used to induce progenitor cells to differentiate into chondrocytes in vitro (Diekman et al. 2009; Johnstone et al. 1998; Kolambkar et al. 2007; Winter et al. 2003). In other studies, a side population of corneal stromal cells has been shown to produce a matrix made up of the cartilage specific collagen II under similar chondrogenic differentiation conditions (Du, Funderburgh, Mann, SundarRaj, & Funderburgh 2005). It has also been reported that scleral cells after four weeks in a chondrogenic differentiation medium containing TGFβ1 and BMP2 expressed cartilage specific markers including aggrecan, and collagen type II. Furthermore, human scleral cells have been shown to retain their chondrogenic potential in vivo after being transplanted into a rat cartilage defect (Seko et al. 2008). It is known that the fibroblastic cells of the sclera and the corneal stroma share a common embryological origin.

As shown herein, keratocytes seeded in culture medium containing TGFβ3 and dexamethasone and in the absence of serum spontaneously formed cell spheroids within 2-3 days by cell aggregation and by three weeks these cell clusters labelled positive for cartilage specific type II collagen. Initially upon treatment with TGFβ3 and dexamethasone, type I collagen expression was also increased. When the medium was changed to a control medium containing fetal calf serum the cell clusters dispersed into a monolayer of cells. Cells growing in the monolayer no longer expressed type II collagen. These results suggest that cell aggregation or environment might be important in collagen type II induction.

Notably, keratocytes which were first proliferated as fibroblasts in serum containing medium did not secrete collagen type II when the medium was changed to the TGFβ3 and dexamethasone containing chondrogenic differentiation medium. This suggests that once proliferated as fibroblasts the cells lose the ability to differentiate along a chondrogenic pathway. Further to this, fibroblasts grown in three-dimensional culture in chondrogenic differentiation medium as a pellet also failed to express cartilage specific collagen type II. These results suggest that the quiescent keratocyte phenotype and cell aggregation are important to chondrogenic differentiation.

It is shown herein that ex vivo culture of normal and keratoconic corneas in chondrogenic differentiation media revealed uniform deposition of type II collagen along the stromal lamellae. Every keratocyte within the corneal stroma was associated with the collagen type II labelling, once again suggesting that the reprogramming into a chondrogenic phenotype is stochastic and confirming that results obtained from the in vitro cell culture were not as a result of proliferation of a side population of progenitor cells. Furthermore, in vivo treatment of corneas in rats also caused the deposition of type II collagen in a manner similar to that seen in ex vivo culture. However, stronger immunolabelling of type II collagen was seen in the anterior part of the cornea when treated in vivo, most probably reflecting easier diffusion of growth factors into the anterior layers of the stroma from the ocular surface.

Studies looking at differences in keratocyte density in keratoconic corneas have reported an overall decrease in cell density. The results here also confirm this. However, unlike other studies which have reported a marked decrease in cell density in the anterior part of the stroma (Hollingsworth, Efron, & Tullo 2005; Ku et al. 2008; Mencucci et al. 2010; Niederer et al. 2008), the results here indicate a marked decrease in keratocyte density in the posterior part of the stroma of the untreated keratoconic cornea also. In keratoconus there is a general thinning of the cornea. It is not known, however, whether this is due to the apoptosis of keratocytes and subsequent decreased production of ECM or whether keratocyte apoptosis is secondary to the process of corneal thinning.

As shown herein, the treated half of the keratoconic cornea which was cultured in the chondrogenic medium containing TGFβ3 and dexamethasone had an increased keratocyte density when compared to the control. Furthermore, the posterior region of the stroma appeared to be repopulated by keratocytes. The keratocytes in the treated half also appeared to look healthier with large prominent nuclei and several cell processes. This indicates that the treatment with the two factors have possibly caused keratocytes to proliferate and repopulate the stroma, in particular the posterior part which was devoid of keratocytes.

Collagen crosslinking, one of the current treatments for keratoconus, results in an initial period of keratocyte apoptosis in the anterior part of the stroma. This is then followed by a period of repopulation of the stroma by the keratocytes. Keratocyte cell death is generally seen in response to an injury and in the case of crosslinking is understood to be as a result of UVA-induced cellular damage. This apoptotic response is thought to have evolved in order to protect the cornea from further inflammation (Wilson, Netto, & Ambrosio 2003).

Stromal haze which can last up to several months is also observed after the crosslinking treatment. It has been attributed to the increase in collagen diameter and spacing between the collagen fibrils which results in the modification of the corneal microstructure. Most studies have reported a decrease in corneal haze between 6-12 months after the treatment (Greenstein, Fry, Bhatt, & Hersh 2010; Mazzotta et al. 2008). Although there have been several clinical observations of the corneas carried out after the crosslinking treatment there is ambiguity regarding the cause of the corneal haze and other possible downstream effects of the treatment. The fact that it takes several months for corneas to be repopulated and become clear suggests that the crosslinking might be triggering a wound healing response within the stroma.

In this study, even upon long term (up to 8 weeks) in vitro and in vivo treatment there was no evidence of corneal opacity. This is probably due to the deposition of the collagen II in uniform layers along the pre-existing collagen lamellae. Deposition of collagen type III (associated with fibrosis) and alpha-smooth muscle actin (during myofibroblast formation) leads to opacity and scarring. Both these are seen during corneal wounding. Neither of these proteins was expressed in the treated corneas suggesting that wound healing cascades which could bring about scarring were not being triggered.

As described herein, quantitative measurement of type II collagen mRNA expression showed that its expression was significantly lowered upon withdrawal of TGFβ3 and dexamethasone. This suggests that the reprogramming of keratocytes is not irreversible and the subsequent deposition of type II collagen in the ECM can potentially be controlled. This is important for the development of therapeutic methods, as it would not be desirable to induce irrepressible ECM deposition.

Nanoindentation has been employed in the assessment of postoperative therapeutic methods such as crosslinking for keratoconus (a corneal dystrophy) and post-LASIK ectasia in the eye. In one study done on human cadaver corneas it was found that collagen crosslinking caused a two-fold increase in the elastic modulus in the anterior corneal stroma while the posterior stroma was unaffected by the treatment (Dias, Diakonis, Kankariya, Yoo, & Ziebarth 2013). In this study, anterior corneal elasticity was measured. In addition, the results in this study do indicate that posterior stroma keratocyte density was altered in the TGFβ3 and dexamethasone treated corneas.

While nanoindentation does not measure the properties of the individual collagen fibrils it can measure the changes in the inherent elastic property of the cornea which will be altered on collagen II deposition with a subsequent increase in collagen crosslinking. Structural differences within the stroma are reflected in the corresponding differences in biomechanical properties. The results here show that there was almost a three-fold increase in elastic modulus and hardness in the growth factor treated rat corneas. These results indicate that the treatment results in a stiffer cornea with higher elasticity. The elastic modulus is a measure of a substance's resistance to being deformed elastically and therefore a higher elastic modulus indicates that a material is more difficult to deform. In this study, a significant increase in hardness and elastic modulus in 3 week treated corneas when compared to 1 week treated corneas is consistent with the immunohistochemical labelling results that show at least 2-3 weeks of treatment is required for the laying down of detectable layers of type II collagen.

The immunohistochemical labelling results coupled with the gene expression studies and biomechanical testing show that keratocytes within an intact cornea are amenable to reprogramming along a chondrogenic pathway by treatment with TGFβ3 and dexamethasone. The reprogramming by combined TGFβ3 and dexamethasone treatment is stochastic and may be controlled via the modulation of the growth factor treatment period to result in stiffer, more elastic corneas. Notably, administration of both agents is required; when TGFβ3 and dexamethasone are tested separately, no collagen type II production in keratocytes is observed. A novel treatment is therefore proposed for keratoconus and other eye conditions using in vivo tissue engineering, by administration of TGFβ3 and dexamethasone, as described herein.

Example 17: Large Animal Model to Investigate Reshaping of the Cornea

Reshaping the Cornea Whilst Delivering the Optimal Regimen in a Sheep Model

Additional experiments are carried out to use a large animal model to demonstrate reshaping of the cornea. For these experiments, a large animal model is used to allow placement of prescription contact lenses. Sheep are used as a model animal, as their eyes are comparable in size and physiology to that of humans. In addition, housing facilities are available at Lincoln University, Christchurch. It is noted also that sheep have a mild temperament, and are amenable to handling.

Sheep are sedated in accordance with standard operating procedure in the housing facility. The eye drop formulation with optimal TGFβ3 and dexamethasone concentrations (volume scaled) based upon the rodent dose optimisation studies are instilled in the right eye followed by the placing of corneal INTACS® (or similar scleral rings) to hold the desired curvature of the cornea during collagen deposition (FIG. 18). Eye drops are continued to be administered either once or twice daily (as determined in rodent optimisation studies) for a period of three weeks. The INTACS® are then removed and the animals are continued to be housed for a further three weeks or six months.

Figure 19A:
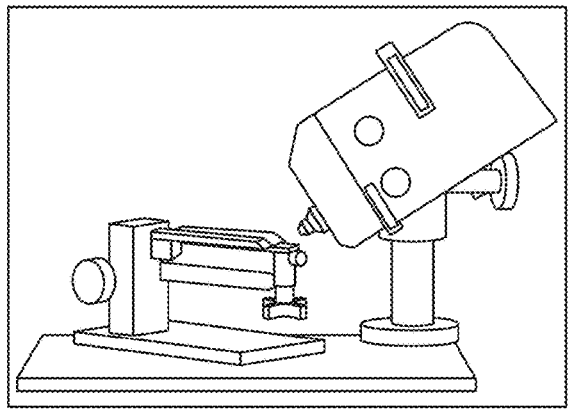
FIG. 19A: The Phoenix Micron IV in vivo eye imaging system. The imaging system enables measurement of corneal thickness, curvature, and transparency.
Figure 19C:
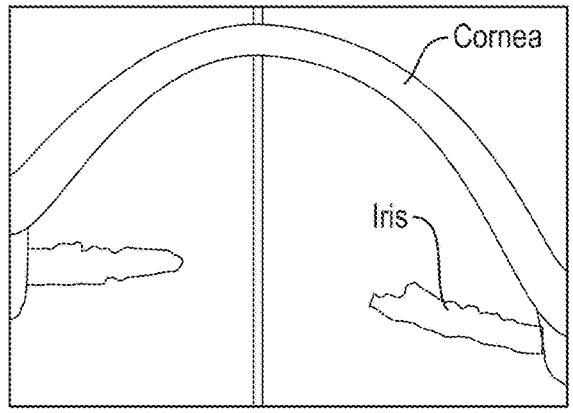
FIG. 19C: A nanoindenter.
Figure 19B:
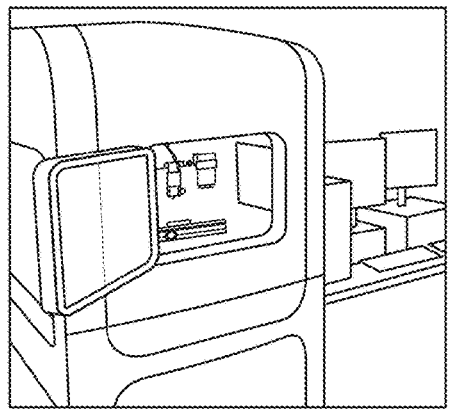
FIG. 19B: OCT attachment enables visualisation of the anterior eye and measurement of corneal thickness and integrity, similar to the image seen here.
Figure 19D:
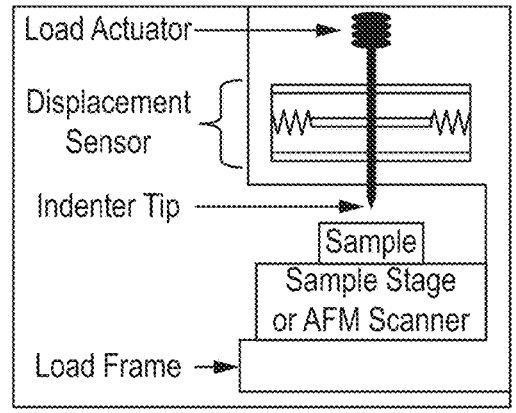
FIG. 19D: schematic representation of the set-up which will be used to assess corneal biomechanics ex vivo in sheep. Output is shown as a load-displacement curve which can be analysed to obtain Young's modulus of elasticity, and a measure of hardness.
Figure 19E:
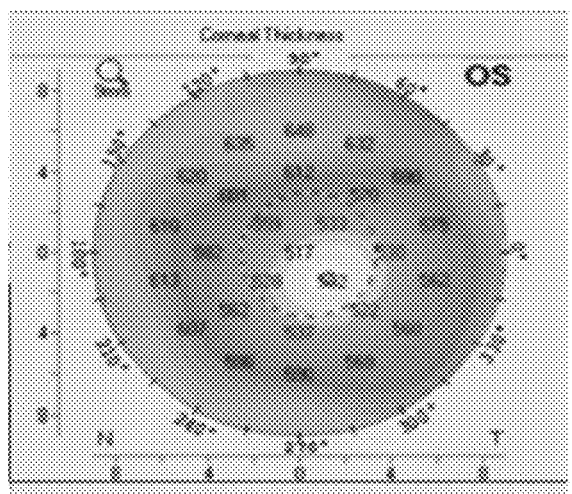
FIG. 19E: In large animals such as sheep, corneal thickness is indicated in microns.
Figure 19F:
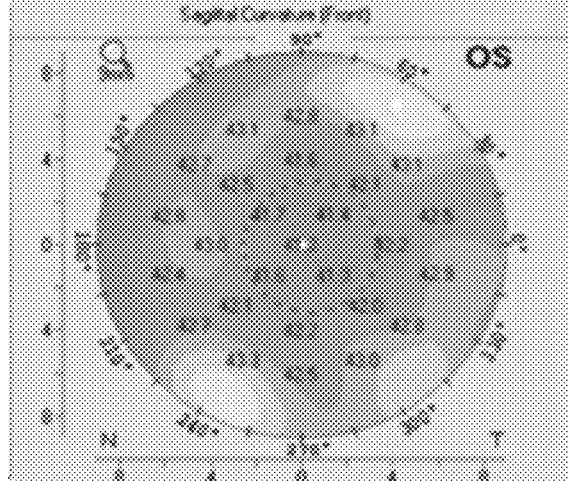
FIG. 19F: In large animals such as sheep, corneal curvature measurements are obtained using a portable Pentacam®. For corneal curvature, widely spaced colour contours indicate a large radius of curvature; narrower contours indicate areas of steeper curvature. Numbers indicate the radius of curvature at each point.

Before treatment and at the end of the treatment (when the INTACS® are removed), corneal thickness and curvature measurements are taken. The portable corneal pachymeter is used to detect changes in corneal thickness of treated versus control contralateral corneas in vivo. A portable Pentacam® is used to measure corneal curvature as well as corneal thickness of the sheep eyes before and after treatment (FIG. 19E and FIG. 19F). Corneal measurements are repeated again at three weeks after lenses removal with the final (most accurate) Pentacam® measurements. These are taken after killing the animal but prior to eye removal for immunohistological and biomechanical analysis as described above for rodent corneas. In the unlikely event that the sheep are unable to tolerate a hard contact lens (signs of infection, inflammation or irritability), the study is continued without lenses, which allows completion of key parameters such as type II collagen deposition and distribution, and biomechanical properties.

In view of the results, it is proposed to use in vivo tissue engineering as described in detail herein, in combination with of a rigid gas permeable OrthoK contact lenses (or similar) to permanently reshape and stabilise the cornea, providing treatment for common corneal defects, including myopia.

REFERENCES

Ashwin, P. T., & McDonnell, P. J. (2010). Collagen cross-linkage: a comprehensive review and directions for future research. British Journal of Ophthalmology, 94(8), 965-970.

Cosar, C. B. et al. (2002). Indications for penetrating keratoplasty and associated procedures, 1996-2000. Cornea, 21(2), 148-151.

Cowin, A. J., Holmes, T. M., Brosnan, P., & Ferguson, M. W. (2001). Expression of TGF-beta and its receptors in murine fetal and adult dermal wounds. European Journal of Dermatology, 11(5), 424-31.

Denniston A. K. O., Murray P. I. (2009) Oxford Handbook of Ophthalmology (OUP). Second edition. Oxford: New York. Oxford University Press.

Desmouliere, A., et al. (2005). Tissue repair, contraction, and the myofibroblast. Wound Repair and Regeneration, 13(1), 7-12.

Dias, J., Diakonis, V. F., Kankariya, V. P., Yoo, S. H., & Ziebarth, N. M. (2013). Anterior and posterior corneal stroma elasticity after corneal collagen crosslinking treatment. Experimental Eye Research, 116, 58-62.

Dias, J. M., & Ziebarth, N. M. (2013). Anterior and posterior corneal stroma elasticity assessed using nanoindentation. Experimental Eye Research, 115, 41-46.

Dickinson, M. E., & Schirer, J. P. (2009). Probing more than the surface. Materials Today, 12(7), 46-50.

Diekman, B. O., Rowland, C. R., Lennon, D. P., Caplan, A. I., & Guilak, F. (2009). Chondrogenesis of adult stem cells from adipose tissue and bone marrow: induction by growth factors and cartilage-derived matrix. Tissue engineering Part A, 16(2), 523-533.

Dobbins, K. R., F. W. Price Jr., W. E. Whitson. (2000). Trends in the indications for penetrating keratoplasty in the Midwestern United States. Cornea, 19(6), 813-816.

Ebenstein, D. M., & Pruitt, L. A. (2006). Nanoindentation of biological materials. Nano Today, 1(3), 26-33.

Edmund, C. (1988). Corneal elasticity and ocular rigidity in normal and keratoconic eyes. Acta Ophthalmologica, 66(2), 134-140.

Edwards, M. et al. (2002). Indications for corneal transplantation in New Zealand: 1991-1999. Cornea, 21(2), 152-155.

Farquharson, C., Berry, J. L., Barbara Mawer, E., Seawright, E., & Whitehead, C. C. (1998). Ascorbic acid-induced chondrocyte terminal differentiation: the role of the extracellular matrix and 1, 25-dihydroxyvitamin D. European Journal of Cell Biology, 76(2), 110-118.

Fredrick, D. R. (2002). Myopia. BMJ: British Medical Journal, 324(7347), 1195.

Fukuchi, T., Yue, B., Sugar, J., & Lam, S. (1994). Lysosomal enzyme activities in conjunctival tissues of patients with keratoconus. Archives of Ophthalmology, 112(10), 1368.

Funderburgh, J. L. (2000). Corneal proteoglycans. In: Proteoglycans: Structure, Biology and Molecular Interactions, R. V. Lozzo, Editor. Marcel Dekker.

Funderburgh, J. L., Mann, M. M., Funderburgh, M. L., Corpuz, L., & Roth, M. R. (2001). Proteoglycan expression during transforming growth factor-induced keratocyte-myofibroblast transdifferentiation. Journal of Biological Chemistry, 276(47), 44173.

Funderburgh, J. L., M. M. Mann, and M. L. Funderburgh (2003) Keratocyte phenotype mediates proteoglycan structure. Journal of Biological Chemistry, 278(46): 45629.

Gabbiani, G. (2003). The myofibroblast in wound healing and fibrocontractive diseases. The Journal of Pathology, 200(4), 500-503.

Ghoniem, A. A., Acil, Y., Wiltfang, J., & Gierloff, M. (2015). Improved adipogenic in vitro differentiation: comparison of different adipogenic cell culture media on human fat and bone stroma cells for fat tissue engineering. Anatomy & Cell Biology, 48(2), 85-94.

Greene, C. A. et al. (2013). Cells from the adult corneal stroma can be reprogrammed to a neuron-like cell using exogenous growth factors. Experimental Cell Research, 322(1), 122-132.

Greenstein, S. A., Fry, K. L., Bhatt, J., & Hersh, P. S. (2010). Natural history of corneal haze after collagen crosslinking for keratoconus and corneal ectasia: Scheimpflug and biomicroscopic analysis. Journal of Cataract & Refractive Surgery, 36(12), 2105-2114.

Gurdon, J. B., D. A. Melton. (2008). Nuclear reprogramming in cells. Science, 322, 1811-1815.

Gordon, M. K., R. A. Hahn (2010). Collagens. Cell and Tissue Research, 339(1), 247-257.

Høkelien, A. M., P. Collas. (2002). Novel approaches to transdifferentiation. Cloning & Stem Cells, 4(4), 379-387.

Heng, B. C., Cao, T., & Lee, E. H. (2004). Directing stem cell differentiation into the chondrogenic lineage in vitro. Stem Cells, 22(7), 1152-1167.

Hollingsworth, J. G., Efron, N., & Tullo, A. B. (2005). In vivo corneal confocal microscopy in keratoconus. Ophthalmic and Physiological Optics, 25(3), 254-260.

Ignotz, R. A. & Massague, J. (1986). Transforming growth factor-beta stimulates the expression of fibronectin and collagen and their incorporation into the extracellular matrix. Journal of Biological Chemistry, 261, 4337-4345.

Ignotz, R. A., Endo, T., & Massague, J. (1987). Regulation of fibronectin and type I collagen mRNA levels by transforming growth factor-beta. Journal of Biological Chemistry, 262(14), 6443-6446.

Jackson T. L. (2008) Moorfields Manual of Ophthalmology, Mosby, Elsevier.

Jester, J. V., Rodrigues, M. M., & Herman, I. M. (1987). Characterization of avascular corneal wound healing fibroblasts. New insights into the myofibroblast. The American Journal of Pathology, 127(1), 140.

Jester, J. V., et al. (2002). TGFβ induced myofibroblast differentiation of rabbit keratocytes requires synergistic TGFβ, PDGF and integrin signaling. Experimental Eye Research 75(6), 645-657.

Jhanji, V., Sharma, N., & Vajpayee, R. B. (2011). Management of keratoconus: current scenario. British Journal of Ophthalmology, 95(8), 1044-1050.

Jinabhai, A., H. Radhakrishnan, C. O'Donnell. (2010). Pellucid corneal marginal degeneration: a review. Contact Lens & Anterior Eye, 34(2), 56-63.

Johnstone, B., Hering, T. M., Caplan, A. I., Goldberg, V. M., & Yoo, J. U. (1998). In Vitro Chondrogenesis of Bone Marrow-Derived Mesenchymal Progenitor Cells. Experimental Cell Research, 238(1), 265-272.

Kadler, K. E., Baldock, C., Bella, J., & Boot-Handford, R. P. (2007). Collagens at a glance. Journal of Cell Science, 120(12), 1955-1958.

Karamichos, D., Hutcheon, A., & Zieske, J. (2011). Transforming growth factor-β3 regulates assembly of a non-fibrotic matrix in a 3D corneal model. Journal of Tissue Engineering and Regenerative Medicine, 5(8), e228-e238.

Karamichos, D., Zareian, R., Guo, X., Hutcheon, A. E. K., Ruberti, J. W., & Zieske, J. D. (2012). Novel in vitro model for keratoconus disease. Journal of Functional Biomaterials, 3(4), 760-775.

Kato, Y. and D. Gospodarowicz (1985). Stimulation by glucocorticoid of the synthesis of cartilage-matrix proteoglycans produced by rabbit costal chondrocytes in vitro. Journal of Biological Chemistry, 260(4), 2364-2373.

C. Kenney, M., & Brown, D. J. (2003). The cascade hypothesis of keratoconus. Contact Lens and Anterior Eye, 26(3), 139-146.

Klintworth, G. K. (1999). Advances in the molecular genetics of corneal dystrophies. American Journal of Ophthalmology, 128(6), 747-754.

Klintworth, G. K., & Damms, T. (1995). Corneal dystrophies and keratoconus. Current Opinion in Ophthalmology, 6(4), 44-56.

Kolambkar, Y. M., Peister, A., Soker, S., Atala, A., & Guldberg, R. E. (2007). Chondrogenic differentiation of amniotic fluid-derived stem cells. Journal of Molecular Histology, 38(5), 405-413.

Krachmer, J. H., Feder, R. S., & Belin, M. W. (1984). Keratoconus and related noninflammatory corneal thinning disorders. Survey of Ophthalmology, 28(4), 293-322.

Ku, J. Y., Niederer, R. L., Patel, D. V., Sherwin, T., & McGhee, C. N. (2008). Laser scanning in vivo confocal analysis of keratocyte density in keratoconus. Ophthalmology, 115(5), 845-850.

Kulyk, W. M., & Hoffman, L. M. (1996). Ethanol exposure stimulates cartilage differentiation by embryonic limb mesenchyme cells. Experimental Cell Research, 223(2), 290-300.

Lee, K. D., et al. (2004). In vitro hepatic differentiation of human mesenchymal cells. Hepatology, 40(6), 1275-1284.

Legeais, J.-M., et al. (2001). Nineteen years of penetrating keratoplasty in the Hotel-Dieu Hospital in Paris. Cornea, 20(6), 603-606.

Linsenmayer, T. F., Fitch, J. M., & Birk, D. E. (1990). Heterotypic collagen fibrils and stabilizing collagens. Annals of the New York Academy of Sciences, 580(1), 143-160.

Ludwig, A. (2005). The use of mucoadhesive polymers in ocular drug delivery. Advanced Drug Delivery Reviews, 57(11), 1595-1639.

Marshall, G. E., Konstas, A. G., & Lee, W. R. (1993). Collagens in ocular tissues. The British Journal of Ophthalmology, 77(8), 515.

Mazzotta, C., Traversi, C., Baiocchi, S., Caporossi, O., Bovone, C., Sparano, M. C., Caporossi, A. (2008). Corneal healing after riboflavin ultraviolet-A collagen crosslinking determined by confocal laser scanning microscopy in vivo: early and late modifications. American Journal of Ophthalmology, 146(4), 527-533. e521.

Meek, K. M., Tuft, S. J., Huang, Y., Gill, P. S., Hayes, S., Newton, R. H., & Bron, A. J. (2005). Changes in collagen orientation and distribution in keratoconus corneas. Investigative Ophthalmology & Visual Science, 46(6), 1948-1956.

Mencucci, R., Marini, M., Paladini, I., Sarchielli, E., Sgambati, E., Menchini, U., & Vannelli, G. B. (2010). Effects of riboflavin/UVA corneal cross-linking on keratocytes and collagen fibres in human cornea. Clinical & Experimental Ophthalmology, 38(1), 49-56.

Mendler, M., Eich-Bender, S. G., Vaughan, L., Winterhalter, K. H., & Bruckner, P. (1989). Cartilage contains mixed fibrils of collagen types II, IX, and XI. The Journal of Cell Biology, 108(1), 191-197.

Menetrey, J., et al. (2000). Growth factors improve muscle healing in vivo. Journal of Bone & Joint Surgery, British Volume, 82(1), 131-137.

Niederer, R. L., Perumal, D., Sherwin, T., & McGhee, C. N. J. (2008). Laser scanning in vivo confocal microscopy reveals reduced innervation and reduction in cell density in all layers of the keratoconic cornea. Investigative Ophthalmology & Visual Science, 49(7), 2964-2970.

Nirmal, H. B., S. R. Bakliwal, S. P. Pawar (2010). In-situ gel: New trends in controlled and sustained drug delivery system. International Journal of PharmTech Research, 2(2), 1398-1408.

Patel, H. Y. et al. (2005). The New Zealand National Eye Bank study 1991-2003: a review of the source and management of corneal tissue. Cornea, 24(5), 576-582.

Patel, D., C. McGhee (2013). Understanding keratoconus: what have we learned from the New Zealand perspective? Clinical and Experimental Optometry, 96(2), 183-187.

Peran, M., et al. (2011). Transdifferentiation: why and how? Cell Biology International, 35(4), 373-379.

Pramanik, S., Musch, D. C., Sutphin, J. E., & Farjo, A. A. (2006). Extended long-term outcomes of penetrating keratoplasty for keratoconus. Ophthalmology, 113(9), 1633-1638.

Premaraj et al. (2006). Sustained delivery of bioactive cytokine using a dense collagen gel vehicle collagen gel delivery of bioactive cytokine. Arch Oral Biol. 51(4), 325-33.

Rabinowitz, Y. S. (1998). Keratoconus. Survey of Ophthalmology, 42(4), 297-319.

Rabonitz, Y. S. (2004). Ectatic Disorders of the Cornea. In: The Cornea, 4th edition. Lippincott Williams & Wilkins.

Romero-Jimenez, M., Santodomingo-Rubido, J., & Wolffsohn, J. S. (2010). Keratoconus: a review. Contact Lens and Anterior Eye, 33(4), 157-166.

Rupenthal, I. D., Green, C. R., & Alany, R. G. (2011). Comparison of ion-activated in situ gelling systems for ocular drug delivery. Part 2: Precorneal retention and in vivo pharmacodynamic study. International Journal of Pharmaceutics.

Schuldiner, M., Yanuka, O., Itskovitz-Eldor, J., Melton, D. A., & Benvenisty, N. (2000). Effects of eight growth factors on the differentiation of cells derived from human embryonic stem cells. Proceedings of the National Academy of Sciences, 97(21), 11307-11312.

Shah, M., Foreman, D. M., & Ferguson, M. W. (1995). Neutralisation of TGF-beta 1 and TGF-beta 2 or exogenous addition of TGF-beta 3 to cutaneous rat wounds reduces scarring. Journal of Cell Science, 108(3), 985-1002.

Sherwin, T., & Brookes, N. H. (2004). Morphological changes in keratoconus: pathology or pathogenesis. Clinical & Experimental Ophthalmology, 32(2), 211-217.

Spoerl, E., Huhle, M., & Seiler, T. (1998). Induction of cross-links in corneal tissue. Experimental Eye Research, 66(1), 97-103.

Takahashi, K., S. Yamanaka. (2006). Induction of pluripotent stem cells from mouse embryonic and adult fibroblast cultures by defined factors. Cell, 126(4), 663-676.

Tsang et al. (1995). Characterization of recombinant soluble human transforming growth factor-beta receptor type II (rhTGF-beta sRII). Cytokine, 7(5), 389-97.

Wells, S. M. (2003). Mechanical design of elastic biopolymers. Physics in Canada, 59(2), 67-74.

Wernig, M. et al. (2007). In vitro reprogramming of fibroblasts into a pluripotent ES-cell-like state. Nature, 448 (7151), 318-324.

Willshaw H. et al. (2000). A Handbook of Paediatric Ophthalmology. Pensord Press: United Kingdom.

Wilson, S. E., Netto, M., & Ambrosio, R. (2003). Corneal cells: chatty in development, homeostasis, wound healing, and disease. American Journal of Ophthalmology, 136(3), 530-536.

Winter, A., Breit, S., Parsch, D., Benz, K., Steck, E., Hauner, H., Richter, W. (2003). Cartilage-like gene expression in differentiated human stem cell spheroids: A comparison of bone marrow-derived and adipose tissu-ederived stromal cells. Arthritis & Rheumatism, 48(2), 418-429.

Wollensak, G., Spoerl, E., & Seiler, T. (2003). Riboflavin/ultraviolet-A—induced collagen crosslinking for the treatment of keratoconus. American Journal of Ophthalmology, 135(5), 620-627.

Wollensak, J., & Buddecke, E. (1990). Biochemical studies on human corneal proteoglycans—a comparison of normal and keratoconic eyes. Graefe's Archive for Clinical and Experimental Ophthalmology, 228(6), 517-523.

Worster, A. A., Nixon, A. J., Brower-Toland, B. D., & Williams, J. (2000). Effect of transforming growth factor 01 on chondrogenic differentiation of cultured equine mesenchymal stem cells. American Journal of Veterinary Research, 61(9), 1003-1010.

Yamanaka, S., H. M. Blau. (2010). Nuclear reprogramming to a pluripotent state by three approaches. Nature, 465 (7299), 704-712.

Yoon Y. M., Oh C. D., Kim D. Y., Lee Y S, Park J. W., Huh T. L., Kang S. S., Chun J. S. (2000). Epidermal growth factor negatively regulates chondrogenesis of mesenchymal cells by modulating the protein kinase C-alpha, Erk-1, and p38 MAPK signaling pathways. Biol Chem. 275(16):12353-9.

A person of ordinary skill in the art will readily appreciate from the disclosure that later modifications, substitutions, and/or variations performing substantially the same function or achieving substantially the same result as embodiments or aspects described herein may be utilised according to such related embodiments or aspects of the present invention. Thus, the invention is intended to encompass, within its scope, the modifications, substitutions, and variations to processes, manufactures, compositions of matter, compounds, means, methods, and/or steps disclosed herein.

All references, including patents and patent applications, cited in this specification are hereby incorporated by reference. No admission is made that any reference constitutes prior art. Nor does discussion of any reference constitute an admission that such reference forms part of the common general knowledge in the art, in New Zealand or in any other country

What is claimed is:

1. A kit comprising:
   (i) a composition comprising a TGFβ3 polypeptide which comprises the amino acid sequence of SEQ ID NO:1 or which is at least 90% identical to the amino acid sequence of SEQ ID NO:1, and dexamethasone or derivative thereof or a related steroidal agent; and
   (ii) one or more contact lenses, corneal inserts, corneal implants, or intrastromal rings;
   wherein the kit is adapted to be used in:
   (a) treating or preventing progression of a refractive error of an eye;
   (b) treating or preventing progression of a condition associated with thinning or irregularity of a cornea; or
   (c) treating or preventing progression of a corneal condition selected from the group consisting of: keratoconus, myopia, hyperopia, astigmatism, presbyopia, and stromal dystrophies;
   and wherein use of the kit in any of (a), (b), or (c) does not result in scarring in the cornea or in the eye.

2. The kit of claim 1, wherein:
   (a) the one or more contact lenses, corneal inserts, corneal implants, or intrastromal rings is/are adapted for moulding or holding corneal shape during and/or following treatment with the composition; and/or
   (b) the one or more contact lenses, corneal inserts, corneal implants, or intrastromal rings acts/act as a carrier for the composition or as a composition eluting device.

3. The kit of claim 1, wherein:
   (a) the TGFβ3 polypeptide consists of the amino acid sequence of SEQ ID NO:1; and/or
   (b) the dexamethasone is dexamethasone phosphate.

4. The kit of claim 1, wherein the composition comprises one or more of:
   (a) 10 to 100 ng/ml of the TGFβ3 polypeptide;
   (b) 40 to 4000 ng/ml dexamethasone;
   (c) a formulation for administration once daily or twice daily; or
   (d) a co-formulation with one or more additional agents for the eye.

5. The kit of claim 4, wherein the one or more additional agents for the eye are selected from the group consisting of: anaesthetic agents, anti-inflammatory agents, anti-microbial agents, and lubricants.

6. The kit of claim 1, wherein:
   (a) the kit includes one or more additional agents for the eye;
   (b) the kit includes a contact lens solution; and/or
   (c) the kit includes instructions for use.

7. The kit of claim 6, wherein the one or more additional agents for the eye are selected from the group consisting of: anaesthetic agents, anti-inflammatory agents, anti-microbial agents, and lubricants.

8. A kit comprising:
   (i) a first composition comprising a TGFβ3 polypeptide which comprises the amino acid sequence of SEQ ID NO:1 or which is at least 90% identical to the amino acid sequence of SEQ ID NO:1;
   (ii) a second composition comprising dexamethasone or derivative thereof or a related steroidal agent; and
   (iii) one or more contact lenses, corneal inserts, corneal implants, or intrastromal rings: wherein the kit is adapted to be used in:
   (a) treating or preventing progression of a refractive error of an eye;
   (b) treating or preventing progression of a condition associated with thinning or irregularity of a cornea; or
   (c) treating or preventing progression of a corneal condition selected from the group consisting of: keratoconus, myopia, hyperopia, astigmatism, presbyopia, and stromal dystrophies;

and wherein use of the kit in any of (a), (b), or (c) does not result in scarring in the cornea or in the eye.

9. The kit of claim 8, wherein:
(a) the one or more contact lenses, corneal inserts, corneal implants, or intrastromal rings is/are adapted for moulding or holding corneal shape during and/or following treatment with the first composition and the second composition; and/or
(b) the one or more contact lenses, corneal inserts, corneal implants, or intrastromal rings acts/act as a carrier for the first composition or the second composition, or acts/act as a composition eluting device.

10. The kit of claim 8, wherein:
(a) the TGFβ3 polypeptide consists of the amino acid sequence of SEQ ID NO:1; and/or
(b) the dexamethasone is dexamethasone phosphate.

11. The kit of claim 8, wherein the first composition comprises one or more of:
(a) 10 to 100 ng/ml of the TGFβ3 polypeptide;
(b) a formulation for administration once daily or twice daily; or
(c) a co-formulation with one or more additional agents for the eye.

12. The kit of claim 11, wherein the one or more additional agents for the eye are selected from the group consisting of: anaesthetic agents, anti-inflammatory agents, anti-microbial agents, and lubricants.

13. The kit of claim 8, wherein the second composition comprises one or more of:
(a) 40 to 4000 ng/ml dexamethasone;
(b) a formulation for administration once daily or twice daily; or
(c) a co-formulation with one or more additional agents for the eye.

14. The kit of claim 13, wherein the one or more additional agents for the eye are selected from the group consisting of: anaesthetic agents, anti-inflammatory agents, anti-microbial agents, and lubricants.

15. The kit of claim 8, wherein:
(a) the kit includes one or more additional agents for the eye;
(b) the kit includes a contact lens solution; and/or
(c) the kit includes instructions for use.

16. The kit of claim 15, wherein the one or more additional agents for the eye are selected from the group consisting of: anaesthetic agents, anti-inflammatory agents, anti-microbial agents, and lubricants.

\* \* \* \* \*

SEQUENCE LISTING

```
<160> NUMBER OF SEQ ID NOS: 1

<210> SEQ ID NO 1
<211> LENGTH: 112
<212> TYPE: PRT
<213> ORGANISM: Artificial
<220> FEATURE:
<223> OTHER INFORMATION: Synthetic polypeptide construct

<400> SEQUENCE: 1

Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Trp Lys Trp
                20                  25                  30

Val His Glu Pro Lys Gly Tyr Tyr Ala Asn Phe Cys Ser Gly Pro Cys
             35                  40                  45

Pro Tyr Leu Arg Ser Ala Asp Thr Thr His Ser Thr Val Leu Gly Leu
         50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
                 85                  90                  95

Lys Val Glu Gln Leu Ser Asn Met Val Val Lys Ser Cys Lys Cys Ser
                100                 105                 110
```